(12) United States Patent
Lurie

(10) Patent No.: US 7,204,251 B2
(45) Date of Patent: *Apr. 17, 2007

(54) DIABETES TREATMENT SYSTEMS AND METHODS

(75) Inventor: Keith G. Lurie, Minneapolis, MN (US)

(73) Assignee: Advanced Circulatory Systems, Inc., Eden Prairie, MN (US)

( * ) Notice: Subject to any disclaimer, the term of this patent is extended or adjusted under 35 U.S.C. 154(b) by 454 days.

This patent is subject to a terminal disclaimer.

(21) Appl. No.: 10/401,493

(22) Filed: Mar. 28, 2003

(65) Prior Publication Data

US 2005/0199237 A1 Sep. 15, 2005

Related U.S. Application Data

(63) Continuation-in-part of application No. 10/224,263, filed on Aug. 19, 2002, now Pat. No. 6,986,349, which is a continuation-in-part of application No. 10/119,203, filed on Apr. 8, 2002, which is a continuation-in-part of application No. 09/854,238, filed on May 11, 2001, now Pat. No. 6,604,523, which is a continuation-in-part of application No. 09/546,252, filed on Apr. 10, 2000, now Pat. No. 6,526,973, which is a continuation of application No. 08/950,702, filed on Oct. 15, 1997, now Pat. No. 6,062,219, which is a continuation-in-part of application No. 08/403,009, filed on Mar. 10, 1995, now Pat. No. 5,692,498, which is a continuation-in-part of application No. 08/149,204, filed on Nov. 9, 1993, now Pat. No. 5,551,420.

(51) Int. Cl.
*A61H 31/00* (2006.01)
*A61M 16/04* (2006.01)

(52) U.S. Cl. .............................. 128/205.24; 128/204.18

(58) Field of Classification Search ........... 128/200.24, 128/202.28, 202.29, 203.11, 205.13, 205.14–205.17, 128/205.24–205.25, 206.21, 207.12, 207.14, 128/207.16; 137/906–909; 600/484, 485, 600/500, 529, 533–83
See application file for complete search history.

(56) References Cited

U.S. PATENT DOCUMENTS 2,774,346 A 12/1956 Halliburton .................. 128/29

(Continued)

FOREIGN PATENT DOCUMENTS

CA 668771 8/1963

(Continued)

OTHER PUBLICATIONS

"Ventilators—Theory and Clinical Application," Dupuis, C.V. Mosby Co., St. Louis, MO @ 1986, pp. 447-448, 481, 496, ISBN 081614201.

(Continued)

*Primary Examiner*—Teena Mitchell
*Assistant Examiner*—Shumaya Ali
(74) *Attorney, Agent, or Firm*—Townsend and Townsend and Crew LLP

(57) ABSTRACT

A method for treating a breathing person suffering from diabetes utilizes a valve system that is interfaced to the person's airway and is configured to decrease or prevent respiratory gas flow to the person's lungs during at least a portion of an inhalation event. The person is permitted to inhale and exhale through the valve system. During inhalation, the valve system functions to produce a vacuum within the thorax to increase blood flow back to the right heart of the person, thereby increasing cardiac output and blood circulation in order to treat the person suffering from diabetes.

8 Claims, 34 Drawing Sheets

U.S. PATENT DOCUMENTS

| | | | |
|---|---|---|---|
| 3,191,596 A | 6/1965 | Bird et al. | 128/29 |
| 3,307,541 A | 3/1967 | Hewson | |
| 3,662,751 A | 5/1972 | Barkalow et al. | 128/145.8 |
| 3,669,108 A | 6/1972 | Sundblom et al. | 128/145.8 |
| 3,794,043 A | 2/1974 | McGinnis | 128/349 |
| 3,815,606 A | 6/1974 | Mazal | 128/351 |
| 3,834,383 A | 9/1974 | Weigl et al. | 128/145.8 |
| 3,933,171 A | 1/1976 | Hay | 137/493.7 |
| 4,041,943 A | 8/1977 | Miller | 128/145.8 |
| 4,077,404 A | 3/1978 | Elam | 128/145.8 |
| 4,166,458 A | 9/1979 | Harrigan | 128/24 |
| 4,226,233 A | 10/1980 | Kritzer | 128/205.13 |
| 4,259,951 A | 4/1981 | Chernack et al. | 128/200.14 |
| 4,298,023 A | 11/1981 | McGinnis | 137/529 |
| 4,316,458 A | 2/1982 | Hammerton-Fraser | 128/205.24 |
| 4,320,754 A | 3/1982 | Watson et al. | |
| 4,349,015 A * | 9/1982 | Alferness | 601/41 |
| 4,397,306 A | 8/1983 | Weisfeldt et al. | |
| 4,446,864 A | 5/1984 | Watson et al. | 128/207.14 |
| 4,449,526 A | 5/1984 | Elam | 128/206.21 |
| 4,481,938 A | 11/1984 | Lindley | |
| 4,533,137 A | 8/1985 | Sonne | 272/99 |
| 4,601,465 A | 7/1986 | Roy | 272/99 |
| 4,881,527 A | 11/1989 | Lerman | 128/30.2 |
| 4,898,166 A | 2/1990 | Rose et al. | |
| 5,050,593 A | 9/1991 | Poon | 128/204.23 |
| 5,056,505 A | 10/1991 | Warwick et al. | |
| 5,109,840 A | 5/1992 | Daleiden | 128/205.13 |
| 5,163,424 A | 11/1992 | Kohnke | 128/205.13 |
| 5,193,544 A | 3/1993 | Jaffe | 128/634 |
| 5,217,006 A | 6/1993 | McCulloch | |
| 5,235,970 A | 8/1993 | Augustine | 128/200.26 |
| 5,295,481 A | 3/1994 | Geeham | 601/63 |
| 5,301,667 A | 4/1994 | McGrail et al. | 128/205.14 |
| 5,305,743 A | 4/1994 | Brain | 128/207.15 |
| 5,355,879 A | 10/1994 | Brain | 128/207.15 |
| 5,359,998 A | 11/1994 | Lloyd | 128/203.11 |
| 5,392,774 A | 2/1995 | Sato | 128/207.15 |
| 5,454,779 A | 10/1995 | Lurie et al. | 601/43 |
| 5,551,420 A | 9/1996 | Lurie et al. | 128/205.13 |
| 5,628,305 A | 5/1997 | Melker | |
| 5,645,522 A | 7/1997 | Lurie et al. | 601/34 |
| 5,692,498 A | 12/1997 | Lurie et al. | 128/205.24 |
| 5,704,346 A | 1/1998 | Inoue | |
| 5,730,122 A | 3/1998 | Lurie | 128/207.12 |
| 6,029,667 A | 2/2000 | Lurie | |
| 6,062,219 A | 5/2000 | Lurie et al. | 128/205.24 |
| 6,155,257 A | 12/2000 | Lurie et al. | |
| 6,224,562 B1 | 5/2001 | Lurie et al. | |
| 6,234,985 B1 | 5/2001 | Lurie et al. | |
| 6,312,399 B1 | 11/2001 | Lurie et al. | |
| 6,425,393 B1 | 7/2002 | Lurie et al. | |
| 6,459,933 B1 | 10/2002 | Lurie et al. | |
| 6,463,327 B1 | 10/2002 | Lurie et al. | |
| 6,526,973 B1 | 3/2003 | Lurie et al. | |
| 6,587,726 B2 | 7/2003 | Lurie et al. | |
| 6,604,523 B2 * | 8/2003 | Lurie et al. | 128/205.24 |
| 6,776,156 B2 | 8/2004 | Lurie et al. | |
| 6,863,656 B2 | 3/2005 | Lurie | |
| 6,935,336 B2 | 8/2005 | Lurie et al. | |
| 6,938,618 B2 | 9/2005 | Lurie et al. | |
| 6,986,349 B2 | 1/2006 | Lurie | |
| 2002/0069878 A1 | 6/2002 | Lurie et al. | |
| 2002/0170562 A1 | 11/2002 | Lurie et al. | |
| 2003/0037784 A1 | 2/2003 | Lurie | |
| 2003/0062041 A1 | 4/2003 | Keith et al. | |

FOREIGN PATENT DOCUMENTS

| | | | |
|---|---|---|---|
| CA | 2077608 | 3/1993 | |
| DE | 24 53 490 | 5/1975 | |
| EP | 29352 | 5/1981 | 128/207.16 |
| EP | 0 139 363 | 5/1985 | |
| EP | 0 245 142 | 11/1987 | |
| EP | 0 367 285 | 5/1990 | |
| EP | 0 411 714 A1 | 2/1991 | |
| EP | 0 509 773 A1 | 4/1992 | |
| GB | 1465127 | 2/1977 | |
| GB | 2139099 | 11/1984 | |
| WO | WO90/05518 | 5/1990 | |
| WO | WO93/21982 | 11/1993 | |
| WO | WO95/13108 | 5/1995 | |
| WO | WO95/28193 | 10/1995 | |
| WO | WO96/28215 | 9/1996 | |

OTHER PUBLICATIONS

Directions for use Ambu® CardioPump™, pp. 1-8.
Cohen et al. (1992) "Active compression-decompression resuscitation: A novel method of cardiopulmonary resuscitation." *American Heart Journal* 124 (5):1145-1150.
Cohen et al. (1992) "Active Compression-Decompression A New Method of Cardiopulmonary Resuscitation." *JAMA* 267 (21):2916-2923.
Lindner et al (1993) "Effects of Active Compression-Decompression Resuscitation on Myocardial and Cerebral Resuscitation Blood Flow in Pigs." *Circulation* 88 (3):1254-1263.
Lurie et al. (1995) "Regulated to Death: The Matter of Informed Consent for Human Experimentation in Emergency Resuscitation Research." *PACE* 18:1443-1447.
Mushin W.W. et al., "Automatic Ventilation of the Lungs—The Lewis-Leigh Inflating Valve," *Blackwell Scientific*, Oxford, GB, p. 838.
U.S. Appl. No. 11/127,993, filed May 11, 2005, Lurie et al.
U.S. Appl. No. 10/426,161, filed Apr. 28, 2003, Lurie.
U.S. Appl. No. 10/410,229, filed Apr. 8, 2003, Lurie et al.
U.S. Appl. No. 11/051,345, filed Feb. 4, 2005, Lurie.
U.S. Appl. No. 10/396,007, filed Mar. 24, 2003, Lurie et al.
U.S. Appl. No. 10/119,204, filed Apr. 8, 2002, Lurie et al.
U.S. Appl. No. 10/401,493, filed Mar. 28, 2003, Lurie.

* cited by examiner

Fig. 30
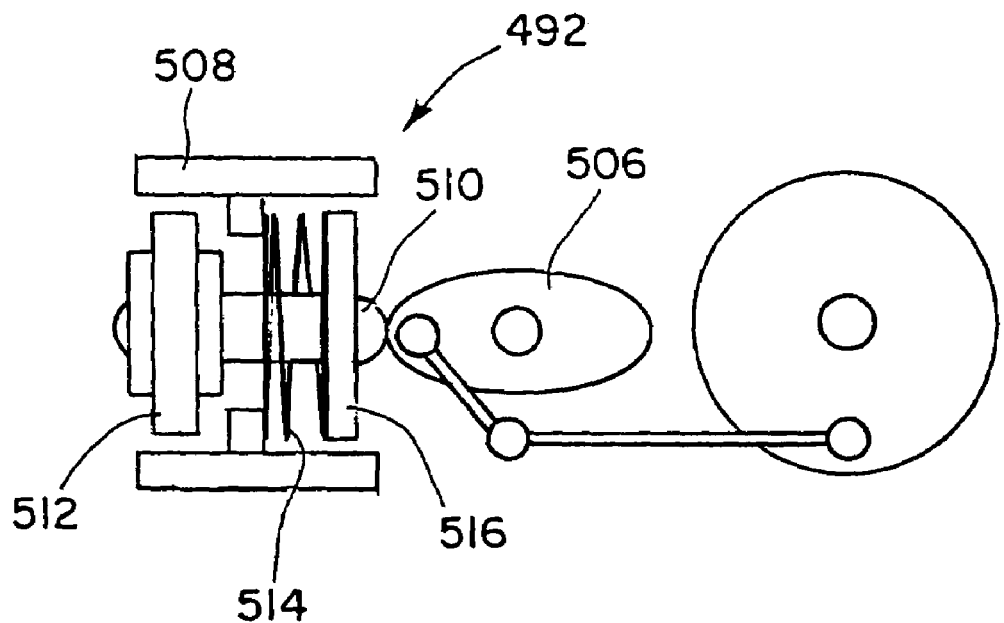
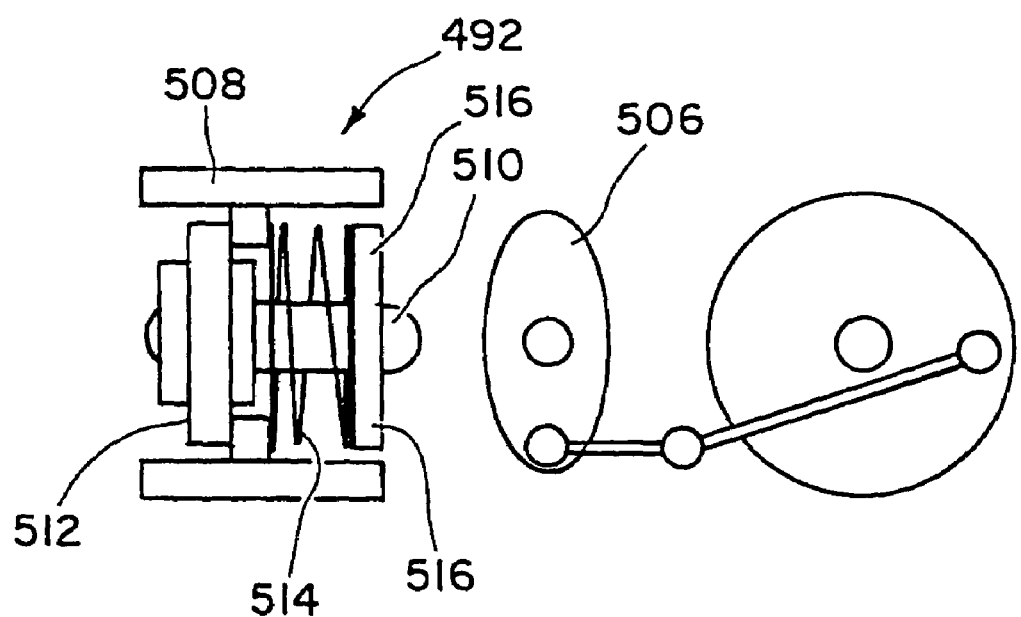
Fig. 31

DIABETES TREATMENT SYSTEMS AND METHODS

CROSS-REFERENCES TO RELATED APPLICATIONS

This application is a continuation in part application of U.S. patent application Ser. No. 10/224,263, filed Aug. 19, 2002 now U.S. Pat. No. 6,986,349, which is a continuation in part application of U.S. patent application Ser. No. 10/119,203, filed Apr. 8, 2002, which is a continuation in part application of U.S. patent application Ser. No. 09/854,238, filed May 11, 2001 now U.S. Pat. No. 6,604,523, which is a continuation in part application of U.S. patent application Ser. No. 09/546,252, filed Apr. 10, 2000 now U.S. Pat. No. 6,526,973, which is a continuation of U.S. patent application Ser. No. 08/950,702, filed Oct. 15, 1997 (now U.S. Pat. No. 6,062,219), which is a continuation-in-part application of U.S. patent application Ser. No. 08/403,009, filed Mar. 10, 1995 (now U.S. Pat. No. 5,692,498), which is a continuation-in-part application of U.S. patent application Ser. No. 08/149,204, filed Nov. 9, 1993 (now U.S. Pat. No. 5,551,420), the disclosures of which are herein incorporated by reference.

This application is also related to U.S. application Ser. No. 09/967,029, filed Sep. 28, 2001, the complete disclosure of which is herein incorporated by reference.

BACKGROUND OF THE INVENTION

The present invention relates generally to devices and methods used in conjunction with increasing blood circulation. In particular, the present invention relates to devices and methods for increasing blood circulation in spontaneously breathing individuals.

Many individuals have a need to increase their blood circulation. This can be the case even if the person is considered to have normal blood circulation. One obvious way to increase blood circulation is to participate in physical activity, such as running, walking, swimming and the like. However, participation in such activities may be inconvenient, and in some cases unpractical or altogether impossible.

Another condition that can affect a person's cardio vascular system is diabetes. With diabetes, a person's vital organ perfusion may be diminished. Over time, this may contribute to organ failure, among other ailments.

Hence, this invention is related to alternative techniques for increasing blood circulation. The invention is also related to the treatment of diabetes where a person's vital organ perfusion may be diminished.

BRIEF SUMMARY OF THE INVENTION

In one embodiment, the invention provides a method for increasing circulation in a breathing person. According to the method, a valve system is interfaced to the person's airway and is configured to decrease or prevent respiratory gas flow to the person's lungs during at least a portion of an inhalation event. The person is permitted to inhale and exhale through the valve system. During inhalation, the valve system functions to produce a vacuum within the thorax to increase blood flow back to the right heart of the person, thereby increasing cardiac output and blood circulation. More specifically, coupling of the valve system to a breathing person increases the magnitude and prolongs the duration of negative intrathoracic pressure in the person's chest, i.e., increases the duration and degree that the intrathoracic pressure is below or negative with respect to the pressure in the peripheral venous vasculature to increase venous return. By enhancing the amount of venous blood flow into the heart and lungs (since equilibration of intrathoracic pressure during inhalation occurs to a greater extent from enhanced venous return rather than rapid inflow of gases into the chest via the patient's airway) cardiopulmonary circulation is increased.

In one aspect, the valve system is incorporated into a facial mask that is coupled to the person's face. In another aspect, the valve system includes a pressure responsive inflow valve that may have an actuating pressure in the range from about 0 cm $H_2O$ to about −40 cm $H_2O$. Conveniently, the actuating pressure of the valve may be varied over time.

In one particular aspect, the valve system may also be configured to prevent or decrease exhaled gases from exiting the person's lungs during at least a portion of an exhalation event to further increase blood circulation. To increase the circulation, the valve system may be interfaced for a time period in the range from about 30 seconds to about 24 hours. In a further aspect, a supply of oxygen may be added through the valve system to supplement oxygen delivery to the person. The valve system also functions to deliver this oxygen into the blood by increasing circulation through the lungs, and also increasing tidal volume (the amount of gas that enters the lungs with each breath).

Such a method may also be used to treat various diseases, such as diseases that are related to impaired venous blood flow or from poor blood circulation. Examples of such conditions that may be treated using such techniques include venous stasis ulcers, deep vein thrombosis, wound healing, and lymphedema. The invention may also be used to treat renal failure.

In a specific embodiment, impeding the airflow into the patient's lungs is accomplished by the use of a flow restrictive or limiting member, such as a flow restrictive orifice disposed within or connected in series with a lumen of a ventilation tube, or a pressure-responsive valve within a lumen of the tube to impede the inflow of air. The pressure-responsive valve is biased to open to permit the inflow of air when the intrathoracic pressure falls below a threshold level. In order to properly ventilate patients who are not able to breath completely independently, the method may permit the injection of respiratory gases. When periodic ventilation is performed, gases can be delivered either through the impeding step or in another embodiment they can bypass the impeding step. In some cases, an oxygen enriched gas may be supplied to the patient through the pressure-responsive valve once this valve opens.

A specific embodiment further provides means for impeding air from leaving the lungs during exhalation to further enhance cardiopulmonary circulation by enhancing positive intrathoracic pressure.

An apparatus for enhancing cardiopulmonary circulation according to one embodiment may comprise a tube, face mask, or moth piece having a flow restrictive element for impeding airflow from the patient's lungs during chest inhalation. A second apparatus according to the invention provides for an improved air-delivery system comprising a compressible structure having a flow restrictive element included in or attached to an opening of the compressible structure to impede the flow of gases to the patient's lungs. Also, a connector is provided for interfacing the compressible structure to the patient, preferably by attaching a facial mask or endotracheal tube to the structure. Alternatively, a mouth piece may be coupled to the valving system.

In another aspect of the invention, a valving system is provided for regulating airflow into a patient's lungs when breathing. The system includes a housing having an upstream region and a downstream region. A means is provided between the upstream region and the downstream region for inhibiting air from flowing from the upstream region to the downstream region when the pressure in the downstream region is less than the pressure in the upstream region. In this manner, air is inhibited from flowing into the patient's lungs during an inhalation attempt thereby forcing more venous blood into the chest and enhancing vital organ perfusion. A means is further provided for allowing air to flow into the downstream region when ventilating the patient. In this way, adequate ventilation can be provided to the patient during the procedure.

In one particular aspect, the inhibiting means comprises a valve which inhibits airflow from the upstream region to the downstream region when the pressure in the downstream region is less than the pressure in the upstream region. The valve preferably includes a diaphragm which is closed when the pressure in the downstream region is less than or equal to the pressure in the upstream region. Such a configuration prevents air from flowing into the patient's lungs during an attempted inhalation while allowing air to be exhausted from the patient's lungs during exhalation. Preferably, the diaphragm is constructed of a flexible membrane. Alternatively, the diaphragm can be constructed using a ball.

In another particular aspect, the diaphragm is biased to open when the pressure in the downstream region is about 2 cm $H_2O$ or greater, and more preferably at about 2 cm $H_2O$ to 15 cm $H_2O$. Biasing of the diaphragm in this manner increases intrathoracic pressure during exhalation to further enhance vital organ perfusion.

In still a further aspect, the means for allowing air into the downstream region includes a means for opening the diaphragm when air is injected into the upstream region to ventilate the patient. The means for opening the diaphragm preferably includes an ambient pressure region that is adjacent the diaphragm. When air is injected into the upstream region, the pressure within the upstream region increases thereby drawing the diaphragm into the ambient pressure region and allowing the air to flow to the patient's lungs.

In an alternative aspect, the means for allowing air into the downstream region comprises a pressure-responsive valve at the downstream region. The pressure-responsive valve allows air into the downstream region when the pressure in the downstream region falls below a threshold level, usually in the range from 0 cm $H_2O$ to $-40$ cm $H_2O$. The pressure-responsive valve is advantageous in allowing ventilation to be provided to the patient while still employing the diaphragm to enhance the extent and duration of negative intrathoracic pressure. Examples of pressure-responsive valves that may be used include, for example, a spring biased valve, an electromagnetically driven valve, or a valve constructed of any deflectable material that will deflect when the threshold pressure is exceeded. As one specific example, the valve may be constructed of a magnetically charged piece of material with a narrow tolerance that is attracted to a gate. This valve will open when the magnetically charged gate pressure is exceeded. In this way, when the negative intrathoracic pressure is exceeded, the valve will be pulled away from the gate to permit gases to flow to the lungs. Such a valve could also be used in place of the diaphragm valve discussed above.

In one option, a source of oxygen-enriched gas may be coupled to the pressure-responsive valve to supply an oxygen-enriched gas to the patient when the pressure-responsive valve is opened. A regulator may be employed to regulate the pressure and/or flow rate of the gas. For example, the pressure may be regulated to be less than the actuating pressure of the valve so that the pressurized gas will not flow to the patient's lungs until the valve is opened when the negative intrathoracic pressure is exceeded.

The system of the invention in another aspect is provided with an air exhaust opening in the housing at the upstream region for exhausting air from the housing. A valve is provided in the exhaust opening which inhibits air from flowing into the housing through the exhaust opening. In this manner, air exhausted from the patient is in turn exhausted from the housing through the exhaust opening. In a further aspect, means are provided for preventing air from exiting the housing through the exhaust opening during injection of air into the housing when ventilating the patient. Preferably air is injected into the housing from a respiratory device, such as a respiratory bag, a ventilator, or the like.

In still a further aspect of the invention, an endotracheal tube, a sealed facial mask, a laryngeal mask, or other airway tube, mouthpiece, or the like is provided and is connected to the housing at the downstream region for attachment to the patient. The endotracheal tube or like device is for insertion into the patient's airway and provides a convenient attachment for the valving system to the patient.

In one embodiment, the invention provides a mechanism to vary the actuating pressure of the inflow valve. In this way, a person is able to operate the mechanism to vary the impedance. In some cases, the valve systems of the invention may include a pressure gauge to display the intrathoracic pressures. By having this information readily available, the user has more information to assist in setting the desired actuating pressure of the inflow valve.

In one aspect, the varying mechanism is configured to vary the actuating pressure to a pressure within the range from about 0 cm $H_2O$ to about $-40$ cm $H_2O$. In another aspect, the inflow valve comprises a shaft having a seal that is configured to block an opening in the housing, and a spring that biases the seal against the housing. With such a configuration, the mechanism may comprise a knob that is movable to vary the biasing force of the spring. For example, the knob may be rotatably coupled to the shaft so that the user may simply turn the knob to vary the actuating pressure.

In another embodiment, the valve systems of the invention may be provided with a safety ventilation passage. If the valve system is inappropriately applied to a patient who is spontaneously breathing, the patient may breathe through this passage while the valve system is coupled to the patient's airway. A safety mechanism is used to maintain the safety ventilation passageway open to permit respiratory gases to freely flow to the patient's lungs until actuated by a rescuer to close the safety ventilation passageway. With such an arrangement, the patient is able to freely breathe if they are capable of so doing.

In one aspect, the safety ventilation passageway is provided through the inflow valve when the inflow valve is in an open position. With this configuration, the safety mechanism is configured to maintain the inflow valve in the open position until actuated by the user to move the inflow valve to a closed position. A variety of ways may be used to actuate the safety mechanism. For example, the housing may include a ventilation port to permit respiratory gases to be injected into the housing, and the safety mechanism may comprise a sensor to sense when the rescuer injects respiratory gases into the housing. In one embodiment, a signal from the sensor is used by a control system to move the inflow valve from the open position to the closed position.

As an example, the sensor may be movable upon injection of respiratory gases into the housing, and the control system may comprise a set of gears that are coupled to the sensor and a cam that is movable by the gears to close the inflow valve. Alternatively, the control system may comprise an electronic controller, a solenoid and a cam. This mechanism may be configured to take electrical signals from the sensor and to operate the solenoid to move the cam and thereby close the inflow valve. As another example, a flap may be moved upon injection of the gases. The flap may cause the movement of a variety of mechanical components that physically reset the inflow valve to the closed position.

A variety of sensors may be used to sense injection of the respiratory gases. For example, sensors that may be used include electronic switches that move in a gas stream, thermistors to sense temperature changes, $CO_2$ detectors, materials that experience a change of resistance when flexed, mechanical flaps that move in a gas stream, and the like.

The invention also provides methods for increasing cardiac output and the blood pressure in a spontaneously breathing person. According to the method, an inflow valve is coupled to the person's airway and the person inhales and exhales. During inhalation, the inflow valve inhibits or completely prevents respiratory gases from entering the lungs for at least some time to augment the person's negative intrathoracic pressure and thereby assist in increasing blood flow back to the right heart of the person. In so doing, the person's blood flow back to the heart and blood pressure is enhanced. The resistance or actuating pressure of the inflow valve may be based on one or more sensed physiological parameters. For example, one parameter may be the negative intrathoracic pressure. For instance, the inflow valve may be used to achieve a negative intrathoracic pressure in the range from about 0 cm $H_2O$ to $-30$ cm $H_2O$ for flow rates in the range from about zero flow to about 70 liters per minute. Other parameters that may be sensed include respiratory rate, end tidal $CO_2$, tissue $CO_2$ content, work of breathing, positive end expiratory pressure, air flow, blood pressure and oxygen saturation. These parameters may be used individually or in combination when adjusting the resistance of the inflow valve. For example, even if the sensed negative intrathoracic pressure is within a desired range, the end tidal $CO_2$ may be outside of a desired range. As such, the resistance of the valve may be adjusted until the end tidal $CO_2$ is acceptable. Conveniently, the inflow valve may be manually operated or operated in an automated fashion. For example, a controller may be used to receive the sensed parameters and then to send signals to an adjustment mechanism that operates the valve to vary the resistance or actuating pressure.

Such a process may be used to treat a variety of conditions where the person's blood pressure is low. For example, such a procedure may be used where the person has low blood pressure due to blood loss, due to the administration of a drug, due to a high gravitational state, due to vasodepressor syncope, due to drowning, due to heat stroke, due to heart attack, due to hypothermia, due to right heart failure, after a return to earth from space, due to sepsis, pericardial effusion, cardiac tamponade, or the like.

In other embodiments, the invention provides systems and methods for treating patients suffering from diabetes. The systems and methods may utilize any of the valve systems described herein to decrease or prevent respiratory gas from flowing to the person's lungs during at least a portion of an inhalation event. As the person spontaneously breathes through the valve system, blood flow is increased to the heart, brain, pancreas, kidneys and the like. In turn, this results in improved vital organ perfusion and function and may lead to better control of hyperglycemia.

The valve systems may be set to open when the negative intrathoracic pressure is in the range from about $-3$ cm $H_2O$ to about $-15$ cm $H_2O$ for patients suffering from diabetes. In some cases, exhaled gases may be prevented from existing the lungs until the intrathoracic reaches about 0 cm $H_2O$ to about 10 cm $H_2O$, and in some cases from about 0 cm $H_2O$ to about 7.5 cm $H_2O$, to further increase vital organ perfusion and function for those suffering from diabetes.

Also, one or more physiological sensors may be used to monitor the patient's condition while breathing through the valve system. These parameters may be used to determine whether the patient is being over exerted.

In another embodiment, a continuous positive airway pressure (CPAP) may be supplied to a patient in combination with any of the valve systems described herein. This continuous positive pressure may be in the range from about 0 cm $H_2O$ to about 20 cm $H_2O$ and may be introduced directly into the valve system. In this way, a continuous amount of positive pressure may be supplied to the patient's respiratory system while the valve system is coupled to the patient's airway. As such, any of the treatments described herein may be performed in combination with the application of CPAP. Although not limiting, the application of CPAP may be used to treat those suffering from sepsis, heart disease, lung disease and the like.

A further understanding of the nature and advantages of the invention will become apparent by reference to the remaining portions of the specification and drawings.

BRIEF DESCRIPTION OF THE DRAWINGS

FIG. 30 is a more detailed view of the inflow valve of FIG. 25 when in the open position.

FIG. 31 illustrates the inflow valve of FIG. 30 when in the closed position.

DETAILED DESCRIPTION OF THE INVENTION

Figure 1:
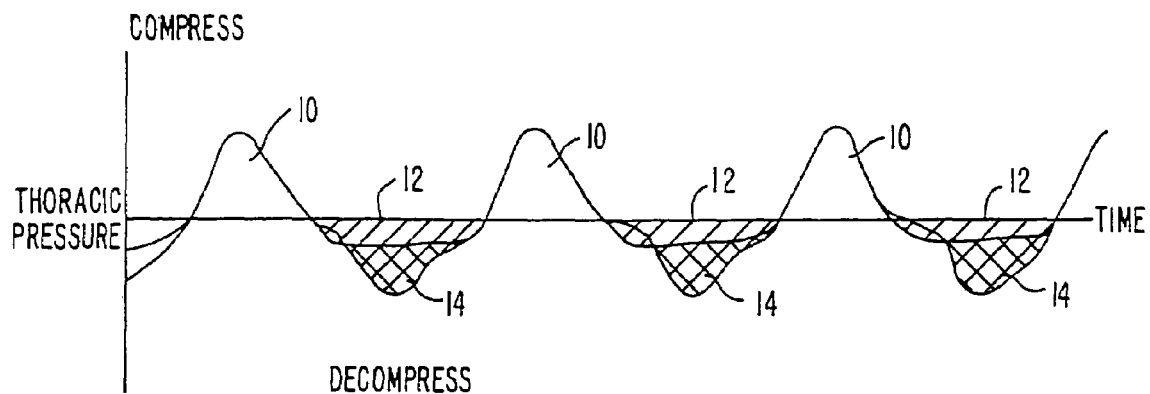
FIG. 1 is a graph illustrating thoracic pressure changes over time when compressing and decompressing a patient's chest according to the present invention.

According to the present invention, methods and devices for increasing cardiopulmonary circulation induced by spontaneous breathing are provided. In particular, the invention improves blood circulation by providing methods and devices which impede airflow into a patient's lungs to enhance negative intrathoracic pressure during attempted inhalations, thus increasing the degree and duration of a pressure differential between the thorax (including the heart and lungs) and the peripheral venous vasculature. Enhancing negative intrathoracic pressure with simultaneous impedance of movement of gases into the airway thus enhances venous blood flow into the heart and lungs and increases cardiopulmonary circulation.

In a broad sense, the present invention provides for temporarily occluding a patient's airway to prevent foreign (outside) air from flowing to a patient's lungs during attempted inhalations to enhance and sustain the duration of negative intrathoracic pressure and enhance blood oxygenation and cardiopulmonary circulation. The patient's airway may be occluded or inflow of gases impeded by any suitable device or mechanism such as by an endotracheal tube, a device attached to an endotracheal tube, a facial mask, a mouth piece used in mouth-to-mouth resuscitation, oropharyngeal airway, laryngeal mask airway, and the like.

A further aspect of the present invention provides for allowing impeded air to flow into the patient's lungs during at least a portion of the inhalation attempt in order to provide some ventilation to the patient while still enhancing the extent and duration of negative intrathoracic pressure to enhance blood oxygenation. Impeding airflow to the patient's lungs may be accomplished by any flow restrictive element such as an orifice, a one-way valve, a spring biased or other valve which is set to open when the negative intrathoracic pressure is in the range from about 0 cm $H_2O$ to $-100$ cm $H_2O$, and more preferably from about $-3$ cm $H_2O$ to about $-40$ cm $H_2O$. A valve designed to open at a threshold pressure value may be either fixed or variable, i.e., the pressure at which the valve opens may be adjusted or may be permanently fixed. Further, examples of pressure-responsive valves that may be used include, for example, an electromagnetically driven valve or a valve constructed of any deflectable material that will deflect when the threshold pressure is exceeded. As one specific example, the valve may be constructed of a magnetically charged piece of material with a narrow tolerance that is attracted to a gate. This valve will open, i.e. separate from the gate, when the magnetically charged gate pressure is exceeded. In this way, when the negative intrathoracic pressure is exceeded, the valve will be pulled away from the gate to permit gases to flow to the lungs.

In some cases, a safety mechanism may be provided to permit respiratory gases to freely flow to the patient's lungs until the safety mechanism is actuated by the user. In this way, the valving system may be coupled to the patient but will only impede patient inspiration until actuated by the user.

Another aspect of the invention provides for air to be impeded from leaving the patient's lungs during exhalation to further enhance cardiopulmonary circulation by enhancing intrathoracic pressure. Typically, air is impeded from leaving the lungs during the exhalation when the positive intrathoracic pressure is in the range from about 2 cm $H_2O$ to 50 cm $H_2O$, and more preferably from about 2 cm $H_2O$ to about 20 cm $H_2O$. Valves that may be used to accomplish such a feature include, for example, a spring valve, a diaphragm valve, include diaphragms constructed of silicone, and a magnetically charged plate that is coupled to a gate. In this manner, when the positive pressure exceeds the magnetic force, the plate is forced away from the gate to permit the gases to exit the lungs.

Another aspect of the present invention provides for ventilating or supplying a gas to the patient. The invention provides for the patient to be able to breathe spontaneously or with assisted ventilation. Ventilation of the patient in one embodiment is performed at about every two to 20 inhalation and exhalation cycles, preferably twice every fifteen cycles, thus providing sufficient fresh air or other gases for adequate gas exchange with the blood in the lungs to the patient. Ventilating the patient may be accomplished by any device or method suitable such as by a compressible or collapsible structure, by a ventilatory bag such as the AMBU bag available from AMBU, Copenhagen, Denmark, or the like. Ventilation could also be superimposed on the exhalation phase to further augment positive intrathoracic pressure. Furthermore, periodic ventilation could be performed either through the impeding step or by bypassing the impeding step altogether. Ventilation can be assisted by continuous positive airway pressure (CPAP) or by an automatic ventilator designed to deliver a given tidal volume followed immediately thereafter by active suction to a given pressure. In other words, as soon as the peak inspiratory volume or pressure has been delivered, the ventilator actively withdraws respiratory gases to reduce the airway and pulmonary pressure to zero or below atmospheric pressure, in a range of $-5$ cm $H_2O$ to about $-30$ cm $H_2O$. As such, the patient's intrathoracic pressure is lowered when the patient begins to take the next breath. Alternatively, high frequency ventilation may be used to minimize positive intrathoracic pressure in patients requiring partial or complete assistance. Negative intrathoracic pressure could be further achieved by an active compression/decompression device.

In an alternative embodiment, ventilation may be provided by introducing oxygen-enriched respiratory gases through the pressure-responsive valve that permits gases into the lungs during the inhalation step once a certain threshold negative intrathoracic pressure is exceeded. This could be introduced under pressure or at atmospheric pressure In this way, during each inhalation, respiratory gases may be supplied to the lungs to ventilate the patient. Use of a pressurized gas is advantageous in that more respiratory gases may be supplied to the lungs once the pressure responsive valve opens. The pressurized gas may be supplied by connecting a pressurized gas source, such as a pressurized tank or bag of $O_2$, to the back side of the pressure-responsive valve using a length of tubing. Conveniently, a regulator may be positioned between the pressure source and the valve to regulate the pressure and/or flow rate of the gas supplied from the pressure source. The pressure may be regulated such that it is less than the actuating pressure of the valve, e.g. by about 1 to 3 cm $H_2O$, so that the valve will not prematurely open. For example, if respiratory gases are to be supplied to the patient when the negative intrathoracic pressure exceeds −14 cm $H_2O$, the pressure of the gas from the gas source must be set to less than 14 cm $H_2O$.

One advantage of supplying supplemental oxygen through the valve and into the respiratory circuit is that addition of the supplemental oxygen may more efficiently be placed into the blood stream. This is because the valve helps to increase blood circulation through the lungs to facilitate the incorporation of additional oxygen into the lungs. Moreover, by injecting oxygen into the lungs, the tidal volume is increased so that additional oxygen may be fed into the blood stream. In one particular embodiment, such a configuration may be incorporated into a diving mask so that a diver may incorporate more oxygen into the blood with a limited amount of oxygen (i.e., a tank of oxygen). Hence, the available oxygen may be better utilized, with less waste with each breath.

When ventilating a patient, the valves of the invention may be modified to regulate the flow rate of air into the lungs. This may be accomplished for example, by including a flow regulator, valve, restriction, reduced size orifice or the like within or associated with the valve so that as respiratory gases are injected into the valve, their flow rate is limited below a threshold amount as the gases enter the patient's airway. By regulating the flow rate of injected respiratory gases, the pressure on the esophagus may be kept within certain limits to prevent gastronomic distention. For example, a reduced size orifice may be provided at or near the exit opening of the valve system housing to regulate the gas flow rate before the gases enter the patient's airway. In this way, a technique is provided to ensure that substantially all of the injected respiratory gases enter the patient's lungs.

In another aspect of the invention, positive pressure may be supplied to a patient's respiratory system using continuous positive airway pressure or CPAP. Such continuous positive pressure may be supplied through any of the valve systems described herein, and may be used with patients who are spontaneously breathing or who have stopped breathing. Hence, the application of CPAP through the valve systems of the invention may be used to treat those suffering from cardiac arrest (where CPR is being formed), heart failure, and the like, as well as with those having sepsis, heart disease, lung disease, and the like.

When supplying CPAP, the positive pressure supplied may be in the range from about 0 cm $H_2O$ to about 20 cm $H_2O$, and may be supplied through the valve systems using any of the techniques described herein. The source of the positive gas may be any of those known within the art, such as with a ventilator that is coupled to the valve system. For example, the ventilator may be coupled to the ventilation or inlet port of the valve systems described herein.

When applying CPAP to the valve systems described herein, the other functions of the valve system may remain operational as well. For example, such valve systems may still be used to regulate the negative intrathoracic pressure within the patient as described herein. As one specific example, the valve systems may be configured to open permit respiratory gases to freely flow to the person's lungs when the negative intrathoracic pressure reaches a pressure in the range from about −2 cm $H_2O$ to about −15 cm $H_2O$.

One significant advantage of the invention is the ability to increase a person's cardiac output and/or blood pressure. By interfacing the valving systems of the invention with spontaneously breathing patients, the valving systems are able to increase the negative intrathoracic pressure when the person inhales. By so doing, more blood is returned to the right heart, thereby increasing the person's cardiac stroke volume and consequently blood pressure. The valving systems used to increase the person's blood pressure may initially completely prevent gas flow to the lungs during an inspiratory effort, or provide some measure of resistance. The complete prevention or initial resistance may be adjusted sometime during the breathing maneuver so that gas flow may proceed to the person's lungs for at least a portion of the inspiratory cycle. For example, if using a pressure responsive valve, the valve may be set to open when reaching a pressure in the range from about 0 cm $H_2O$ to about −50 cm $H_2O$, more preferably from about 0 cm $H_2O$ to about −20 cm $H_2O$, and most preferably from about −3 cm $H_2O$ to about −10 cm $H_2O$ for flow rates of about zero flow to about 70 liters per minute. For valves that simply provide resistance, the valve may be configured to provide similar resistances during the inspiratory effort. Further, one or more sensors may be used to sense various physiological parameters and may be used to manually or automatically vary the cracking pressure of the valve or the amount of resistance produced by the valve.

Examples of situations where the valving systems of the invention may be used to increase blood pressure include those where a spontaneously breathing patient has experienced blood loss, or after receiving a drug (including an anesthetic agent) that causes a decrease in blood pressure. Patients with low blood pressure often suffer from insufficient blood returning to the heart after each beat. This results in a decrease in forward blood flow out of the heart and eventually to low blood pressure. By interfacing the valving systems to the airway, the amount of venous return to the right heart is increased to increase blood pressure. Another example is where a spontaneously breathing patient is in shock secondary to profound blood loss and needs increased blood flow to the right heart. As a further example, such techniques may be used with pilots or astronauts to increase blood flow back to the right heart in high gravitational states or when returning to earth after space flight, and in patients who suffer from a rapid decrease in blood pressure due to vasovagal or vasodepressor syncope. Further examples include low blood pressure due to heat stroke, drowning, heart attack, right heart failure, sepsis, pericardial effusion, tamponade, or the like.

The valving systems of the invention may also incorporate or be associated with sensors that are used to detect changes in intrathoracic pressures or other physiological parameters. Any of the sensors described herein may be configured to wirelessly transmit their measured signals to a remote receiver that is in communication with a controller. In turn the controller may use the measured signals to vary operation of the valve systems described herein. For example, sensors may be used to sense blood pressure, pressures within the heart, or the like and to wirelessly transmit this information to a receiver. This information may then be used by a controller to control the actuating pressure or the resistance of an inflow valve, to control the actuating pressure or resistance of an expiratory valve, to control the injection of oxygen or other gases, to control the administration of drugs or medications, or the like.

The valve systems and/or facial masks of the invention may also include one or more ports for the administration of drugs or other medicaments to the patient's respiratory system. For example, ports may be provided for injecting medicaments by a syringe or pressurized canister. As another example, a nebulized liquid medicament may be supplied through such a port. As a further example, a powdered medicament may be supplied through such a port.

Referring now to FIG. 1, a graph illustrating thoracic pressure changes over time when compressing and decompressing the patient's chest is shown. Area 10 represents the amount of thoracic pressure during the compression phase of active compression-decompression CPR (ACD-CPR). Cross-hatched area 12 represents the negative thoracic pressure during the decompression step of ACD-CPR without a flow restrictive means to restrict the flow of air into the patient's lungs. Double cross-hatched area 14 represents the increase in negative thoracic pressure when the patient's airway is occluded according to the present invention during the decompression step of ACD-CPR. The significance of the increase in negative intrathoracic pressure during the decompression step is that more venous blood is forced into the chest from the peripheral venous vasculature. Consequently, more blood is allowed to be oxygenated and more blood is forced out of the chest during the next compression. A similar scenario is provided when the person is spontaneously breathing and the airway is occluded.

In the embodiments that follow, various devices, systems and methods are described for enhancing the negative intrathoracic pressure in order to increase circulation. Although primarily described in the context of CPR, it will be appreciated that such devices, systems and techniques may also be used for individuals that are spontaneously breathing and do not require the performance of CPR. Such individuals may or may not be suffering from any specific type of disease or ailment, but simply have a need for increased blood circulation (even with individuals having normal blood circulation). However, such techniques may be used for various diseases or ailments associated with blood circulation. For example, the invention may be used in cases related to impaired venous blood flow, such as venous stasis ulcers, deep vein thrombosis, wound healing, and lymphedema. Another example is mild/moderate renal failure.

Hence, the invention may function as a patent powered pump that is capable of enhancing venous return and increasing cardiac output in normal patents and well as those suffering from diseases. In embodiments described in connection with CPR (such as when the chest is compressed and decompressed), it will be appreciated that exhalation and inhalation (respectively) are analogous steps for spontaneously breathing individuals. For convenience of discussion, some embodiments will only be described in connection with CPR, with the understanding that such embodiments may also be used in connection with spontaneously breathing subjects as well. Further, other types of valve systems may also be used to increase blood circulation in breathing subjects, such as those described in copending U.S. application Ser. No. 09/966,945, filed Sep. 28, 2001; and Ser. No. 09/967,029, filed Sep. 28, 2001, the complete disclosures of which are herein incorporated by reference.

In an exemplary embodiment, airflow may be impeded to the patient's lungs during inhalation by placing a ventilatory mask over the patient's mouth and nose. The ventilatory mask also has a pressure-responsive valve attached to prevent airflow to the patient's lungs until the negative intrathoracic pressure of the patient reaches a threshold amount. Also attached to the mask and the pressure-responsive valve is a ventilatory source to provide ventilation to the patient if needed. An oxygen source can also be connected to the system. The ventilatory source may be any device or apparatus suitable for properly ventilating the patient. Preferably, the ventilation source will be an AMBU bag. When ventilation is needed, the AMBU bag may be squeezed to force air into the patient's lungs. The AMBU bag is described in U.S. Pat. No. 5,163,424 which is incorporated herein by reference.

In an alternative embodiment, a ventilation source, preferably an AMBU bag, is used in connection with an improved endotracheal tube. A pressure-responsive valve or other flow restrictive element is placed between the AMBU bag and the endotracheal tube. Preferably, the valve will be positioned within a tube that connects the AMBU bag to the endotracheal tube. The combination of the endotracheal tube with the AMBU bag with adapter can be included in the definition of a "ventilation tube." Before ACD-CPR is performed on the patient, the endotracheal tube is placed in the patient's trachea. During decompression of the patient's chest, the valve prevents airflow to the patient's lungs until the intrathoracic pressure reaches a threshold amount. Additionally, the AMBU bag may be used to ventilate the patient at a desired time. Also included in this embodiment is a one-way expiration valve. This valve allows for expiration of air from the patient during the compression step.

In a modification of either of the first two embodiments, a pressure-responsive expiration valve may also be inserted between the AMBU bag (or comparable ventilation source) and the mask or endotracheal tube. This valve works in a similar manner to the pressure-responsive valve which restricts airflow into the patient's lungs. However, the pressure-responsive expiration valve restricts airflow from the patient's lungs during the compression step of ACD-CPR. An equivalent valve is a positive end-expiratory pressure (PEEP) valve available from AMBU International, Copenhagen, Denmark. Use of such an pressure-responsive expiration valve during inhalation may further increase intrathoracic pressure and thereby force more blood out of the thorax.

In another alternative embodiment, an improved endotracheal tube is used to restrict airflow into the patient's lungs during the active decompression step. Included in the endotracheal tube is a flow restrictive element which operates to impede air from flowing into the patient's lungs. When the endotracheal tube is inserted into the patient's trachea and the patient's chest is actively decompressed, the flow restrictive element impedes air from flowing to the patient's lungs slowing the rise in intrathoracic pressure and thus enhancing blood oxygenation.

When using the improved endotracheal tube during ACD-CPR, periodic ventilation of the patient will usually still be performed to enhance gas exchange to the patient. With the improved endotracheal tube, such manual ventilation may be accomplished by placing a ventilation source at the opening of the endotracheal tube to force oxygen through the endotracheal tube and into the patient's lungs.

Figure 2A:
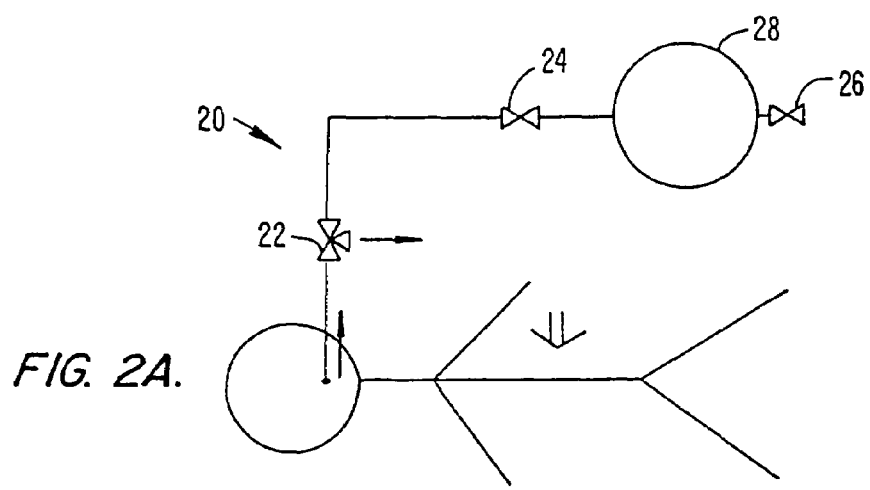
FIG. 2A is a schematic view illustrating airflow through a ventilation circuit when compressing a patient's chest according to the present invention.

Referring now to FIG. 2A, a schematic view illustrating airflow through a ventilation circuit 20 when compressing a patient's chest according to the present invention is shown. During ACD-CPR, the chest is actively compressed forcing air out of the lungs. This air is allowed to expire through a one-way expiration valve 22 within a ventilation circuit 20.

Figure 2B:
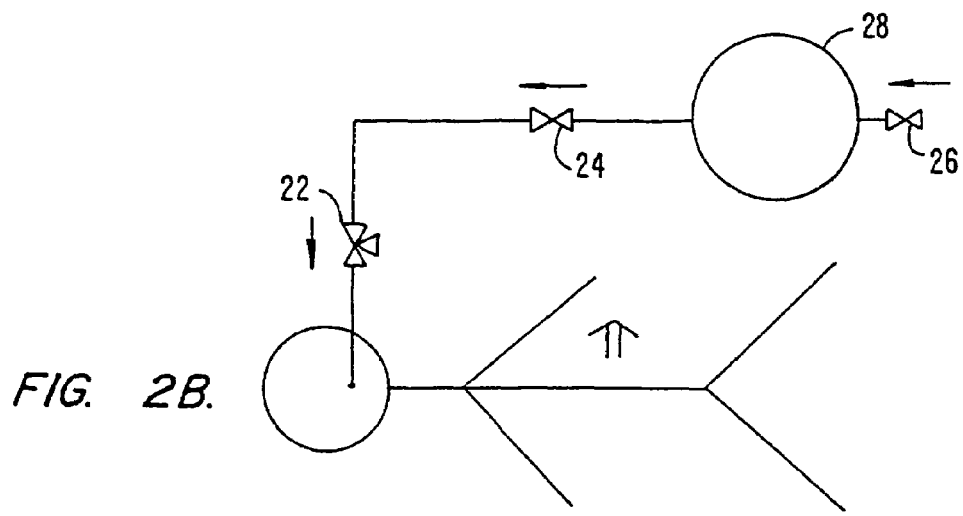
FIG. 2B is a schematic view illustrating airflow through a ventilation circuit when decompressing a patient's chest according to the present invention.

Referring now to FIG. 2B, the same schematic is shown illustrating airflow through the ventilation circuit 20 when decompressing the patient's chest. When the patient's chest is actively decompressed, a negative intrathoracic pressure is created. When this pressure reaches a threshold amount, the inflow valve 24 will open causing air to flow through the ventilation circuit 20 into the patient's lungs. Air is allowed into the ventilation circuit 20 through a ventilation valve 26 and into a ventilation bag 28. From the ventilation bag 28, the air passes through the inflow valve 24 when the negative intrathoracic pressure reaches the threshold amount. The ventilation bag 28 is also used to manually ventilate the patient during ACD-CPR as required.

The method as discussed in connection with FIGS. 2A and 2B requires the chest to be compressed in the range from about 3.5 cm to 5 cm per compression and at a rate from about 60 to 100 compressions per minute for adults.

Figure 3:
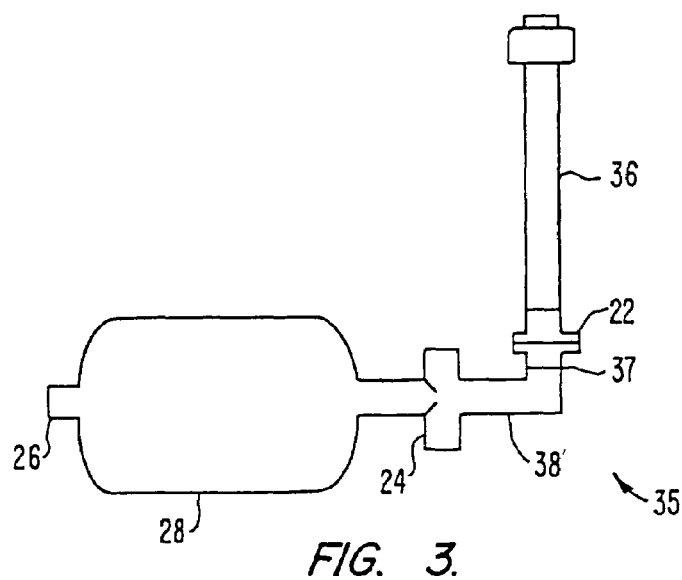
FIG. 3 is a schematic illustration of a first alternative embodiment of a device for impeding airflow into a patient's lungs according to the present invention.

Referring now to FIG. 3, a schematic illustration of a first alternative embodiment of a device 35 for impeding airflow into a patient's lungs according to the present invention is shown. The device 35 comprises an endotracheal tube 36 which is placed into the patient's trachea and provides a ventilation passageway. Connected to the endotracheal tube 36 is a transition tube 38 which connects the endotracheal tube 36 to the ventilation bag 28. Although the endotracheal tube 36 is shown connected to the ventilation bag 28, the endotracheal tube 36 can be used alone or in connection with the ventilation bag 28. The ventilation bag 28 can comprise any type of ventilation source capable of ventilating the patient such as a compressible or collapsible structure. Preferably, the ventilation bag 28 consists of an AMBU bag. Attached or connected to the end of the ventilation bag 28 is a one-way ventilation valve 26. The ventilation valve 26 serves to introduce air into the device 35. Attached or connected to the transition tube 38 is an inflow pressure-responsive valve 24. The inflow valve 24 is biased so that it opens when the negative intrathoracic pressure in the patient's chest reaches a threshold amount. As shown, only one inflow valve 24 is included in the device 35. However, the invention is not limited to only one inflow valve 24. Alternatively, a plurality of inflow valves 24 could be connected in series along the ventilation tube 38. The inflow valve 24 is also not limited to being connected in the center of the transition tube 38, but may be positioned anywhere along the transition tube 38. The inflow valve 24 could be permanently attached to the ventilation bag 28 or transition tube 38 or could be detachable. Alternatively, the inflow valve 24 could be connected to the ventilation bag 28 itself or to the endotracheal tube 36.

The device 35 also contains a one-way expiration valve 22 which allows for air to be expired from the patient's lungs. This generally occurs during the compression phase of ACD-CPR. To insure that the air expired from the patient's lungs will exit through the expiration valve 22, a one-way fish mouth valve 37 (the preferred valve) or any other type of one-way valve can be placed between the inflow valve 24 and the expiration valve 22. Alternatively, the inflow valve 24 itself may be configured as a one-way valve. In either case, air flowing from the endotracheal tube 36 toward the ventilation bag 28 will be forced to expire through the expiration valve 22.

The device 35 may be further modified to include a pressure-responsive expiration valve 39 (not shown) located between the endotracheal tube 36 and the transition tube 38. The pressure-responsive expiration valve works in a reverse manner to that of the inflow valve 24. Specifically, the pressure-responsive expiration valve is biased so that during the compression step of ACD-CPR, air will be allowed to expire from the patient's lungs only when the intrathoracic pressure reaches a threshold amount. The increase in intrathoracic pressure caused by the pressure-responsive expiration valve 39 during compression may assist in forcing more blood out of the thorax and reduce atelectasis of the lungs.

The purpose of the ventilation bag 28 is to provide ventilation to the patient during ACD-CPR. When the ventilation bag 28 comprises an AMBU bag or similar bag used for ventilation, ventilation of the patient may be performed by merely squeezing the AMBU bag with a human hand. This forces air to the patient's lungs as desired.

Figure 4A:
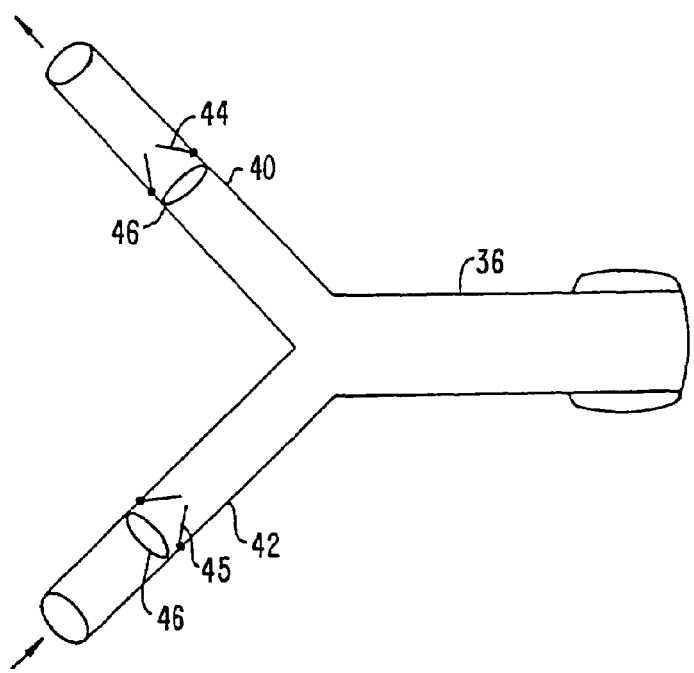
FIG. 4A is a schematic illustration of a second alternative embodiment of the device for impeding airflow into a patient's lungs according to the present invention.

Referring to FIG. 4A, a second alternative embodiment of the device for impeding airflow into a patient's lungs according to the present invention is shown. This particular embodiment is a modified and improved endotracheal tube. Hence, the second alternative embodiment comprises an endotracheal tube 36 having two lumens at its proximal end. The first lumen is an outflow lumen 40, and the second lumen is an inflow lumen 42. Located within outflow lumen 40 is a one-way pressure-responsive expiration valve 44 which operates in a manner similar to that discussed in connection with FIG. 3, except that the expiration valve 44 is specifically designed as a one-way valve. Located within inflow lumen 42 is a one-way pressure-responsive inflow valve 45 which operates to impede airflow to the lungs as discussed in connection with FIG. 3, except that the inflow valve 45 is also specifically designed as a one-way valve. Also shown in inflow lumen 42 and outflow lumen 40 is an O-ring 46 which will be discussed subsequently. Inflow valve 45 and expiration valve 44 are designed as one-way valves so that during the compression phase, air can only be expired from the patient through the endotracheal tube 36 when the intrathoracic pressure reaches a threshold amount. At that moment, expiration valve 44 opens and air expires from the patient through the outflow lumen 40. During decompression, air cannot flow through the endotracheal tube 36 to the patient's lungs until the negative intrathoracic pressure reaches a threshold amount. At that moment, inflow valve 45 opens allowing air to flow through inflow lumen 42 to the patient's lungs. Air is prevented from entering through the outflow lumen 40 because of the one-way expiration valve 44.

Figure 4B:
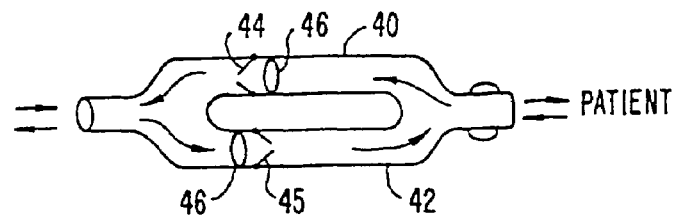
FIG. 4B is a schematic illustration of the device in FIG. 4A with a common inhalation/exhalation port.

Ventilation is possible with the embodiment disclosed in FIGS. 4A and 4B if the inflow lumen 42 is connected to a ventilation source such as a ventilation bag. When the ventilation bag is squeezed, air is allowed to flow through the inflow lumen 42, through the endotracheal tube 36, and to the patient's lungs. In this embodiment, expiration valve 44 is designed so that during ventilation, expiration valve 44 will remain temporarily closed preventing air flowing through inflow lumen 42 escape through outflow lumen 40.

Figure 5A:
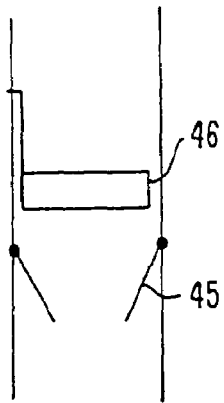
FIG. 5A is a schematic view of a one-way valve used in the device for impeding airflow according to the present invention.
Figure 5B:
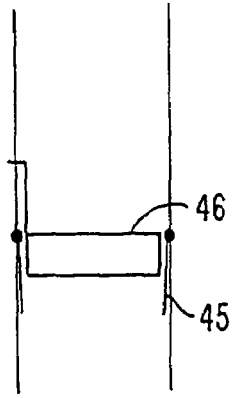
FIG. 5B is a schematic view of the one-way valve in FIG. 5A that is held open.
Figure 5C:
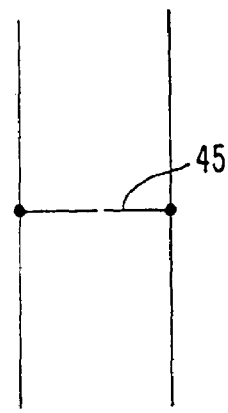
FIG. 5C is a schematic view of a one-way valve that is closed until a threshold pressure is present in the tube according to the present invention.

FIG. 5A is a schematic view of a one-way inflow valve 45 used in a device for impeding airflow according to the present invention. The inflow valve 45 operates so as to allow air only to flow in one direction. As shown, the spring biased inflow valve 45 is completely open. However, the invention also functions properly if the spring biased inflow valve 45 or the spring biased expiration valve 44 are not fully open. Upon successful completion of ACD-CPR, the O-ring 46 that is positioned above the inflow valve 45 is repositioned so that inflow valve 45 is held open as shown in FIG. 5B. Such a positioning of O-ring 46 allows for unimpeded airflow to the patient once there is a return of spontaneous circulation and the inflow valve 45 is no longer needed. An O-ring 46 is also used in a similar manner to lock the one-way expiration valve 44 in an open position upon return of spontaneous circulation. FIG. 5C illustrates the one-way inflow valve 45 in a closed position. When closed, the inflow of air through the inflow valve 45 is occluded.

Figure 6A:
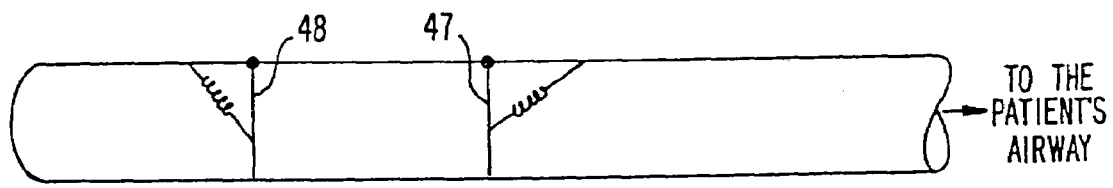
FIG. 6A is a schematic view of a spring biased inflow valve and a spring biased expiration valve to be used in accordance with the present invention.
Figure 6B:
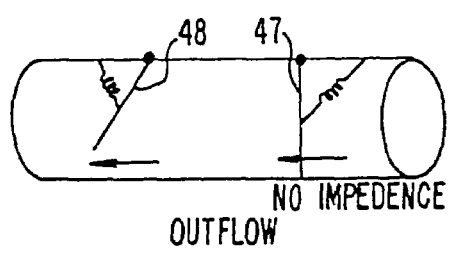
FIG. 6B is a schematic view of FIG. 6A showing the operation of the valves during outflow of air.
Figure 6C:
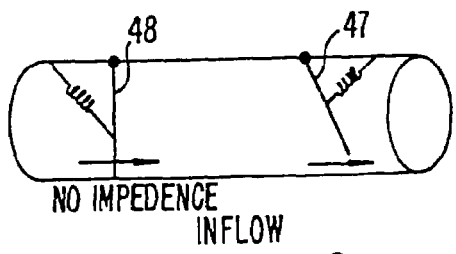
FIG. 6C is a schematic view of FIG. 6A showing the operation of the valves during inflow of air.

FIG. 6A illustrates an inflow valve 47 that is spring biased and an expiration valve 48 that is also spring biased. The inflow valve 47 and the expiration valve 48 are connected in series and may be used in the first alternative embodiment as discussed in connection with FIG. 3, or with the preferred embodiment discussed following in connection with FIG. 9. As shown in FIG. 6C, during the active decompression step, the inflow valve 47 is biased such that it will open when the negative intrathoracic pressure reaches a threshold amount. During the compression phase of ACD-CPR the expiration valve 48 will open to allow air to expire from the patient's lungs when the intrathoracic pressure within the patient's chest reaches a threshold amount as shown in FIG. 6B. Since neither inflow valve 47 nor expiration valve 48 are one-way valves, a fish mouth valve 37 used in connection with a one-way expiration valve 22 as discussed in connection with FIG. 3 must be used. Other valves designed upon a similar principle as the fish mouth valve combination with a one-way expiration valve could also be used. Only one inflow valve 24 and one positive end pressure valve 44 are shown in FIGS. 6A–6C. However, a plurality of inflow valves 47 and/or expiration valves 48 may be connected in a permanent or detachable manner in series to impede the inflow and outflow of air.

Although the valves in FIGS. 6A–6C are shown as being spring-biased, any other valves designed upon a similar principle would work equally as well. The use of such valves as disclosed in FIGS. 6A–6C is only one embodiment and valves constructed according to various other methods and materials is also within the scope of the invention.

Figure 7:
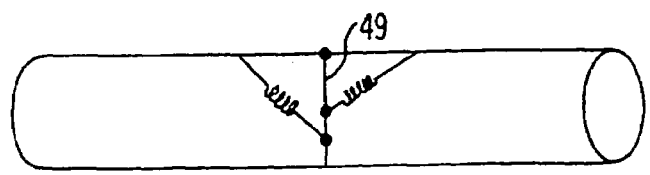
FIG. 7 is a schematic view of a single valve that is spring biased from both sides to be used as an inflow valve and an expiration valve according to the present invention.

As shown in FIG. 7, the inflow valve 47 and the expiration valve 48 may be combined into one joint valve 49 as shown. The joint valve 49 will operate in a manner similar to the two valves 47 and 48 as described in connection with FIG. 6.

Figure 8:
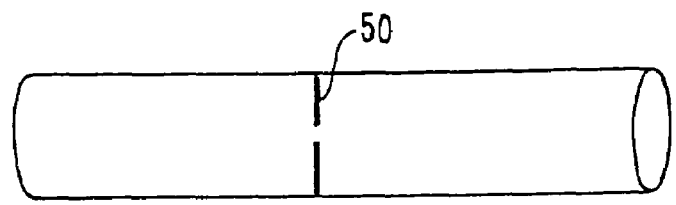
FIG. 8 is a schematic view of a flow restricting orifice to be used with a flow restrictive device according to the present invention.

FIG. 8 illustrates a flow restricting orifice 50 to be used to either impede the airflow into or out of a patient's lungs. The flow restricting orifice 50 operates so that during the decompression step of ACD-CPR airflow is impeded from entering into the patient's lungs, thus increasing the negative intrathoracic pressure. During the compression step, the flow restricting orifice 50 operates to increase the thoracic pressure in the patient's chest by restricting air from existing from the patient's lungs.

Figure 9:
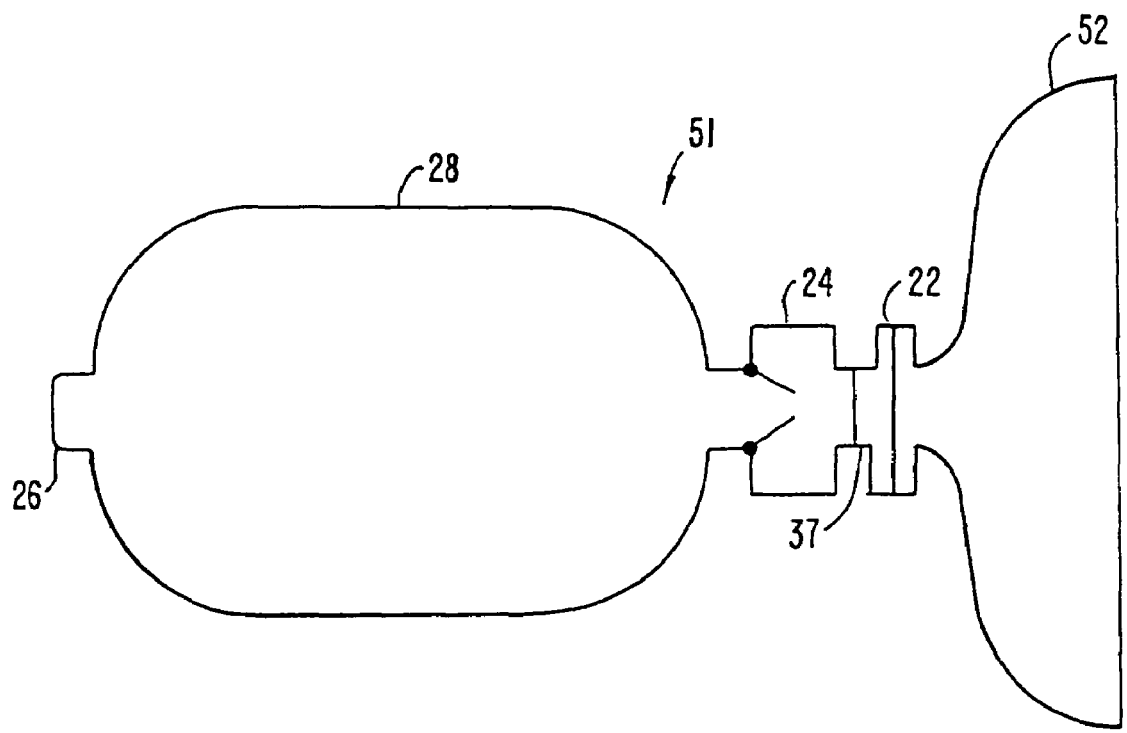
FIG. 9 is a schematic view of an exemplary embodiment of the device for impeding airflow into a patient's lungs according to the present invention.

FIG. 9 illustrates an exemplary embodiment for impeding airflow into a patient's lungs according to the present invention. As shown, the device 51 comprises a ventilation bag 28 that is connected to a facial mask 52 by an inflow valve 24 and an expiration valve 22. Although the facial mask 52 is shown connected to the ventilation bag 28, the facial mask 52 can be used alone or in connection with the ventilation bag. Between the inflow valve 24 and the expiration valve 22 is a one-way fish mouth valve 37 or any other type of one-way valve to prevent air from exiting the patient's lungs and flowing to the ventilation bag 28. The ventilation bag 28 also contains a one-way ventilation valve 26 for allowing air to inflow into the device 51. The exemplary embodiment operates in a manner similar to that of the first alternative embodiment as discussed in connection with FIG. 3. However, instead of inserting an endotracheal tube 36 into the patient's airway, the facial mask 52 is placed over the patient's mouth and nose. A facial strap 54 (not shown) may also be wrapped around the head of the patient to secure the ventilation mask 52 to the patient's face.

Device 51 is preferably used in connection with an oral airway device (not shown) to prevent the patient's airway from becoming occluded, e.g. by the patient's tongue. The oral airway device can be any device that is used to keep the patient's tongue from slipping backward and occluding the airway. Preferably, the oral airway device will be curved and constructed of a plastic material and may or may not be attached to the device 51.

During the decompression phase of ACD-CPR, air is prevented from entering into the patient's lungs through the threshold inflow valve 24 thus increasing the negative intrathoracic pressure. During the compression phase, air is allowed to expire from the patient's lungs through the expiration valve 22. Also, the patient can be ventilated during ACD-CPR by manually squeezing the ventilation bag 28. Consequently, the preferred embodiment serves to enhance cardiopulmonary circulation by increasing the negative intrathoracic pressure to force more blood into the chest from the peripheral venous vasculature.

Figures 10A, 10B, 10C:
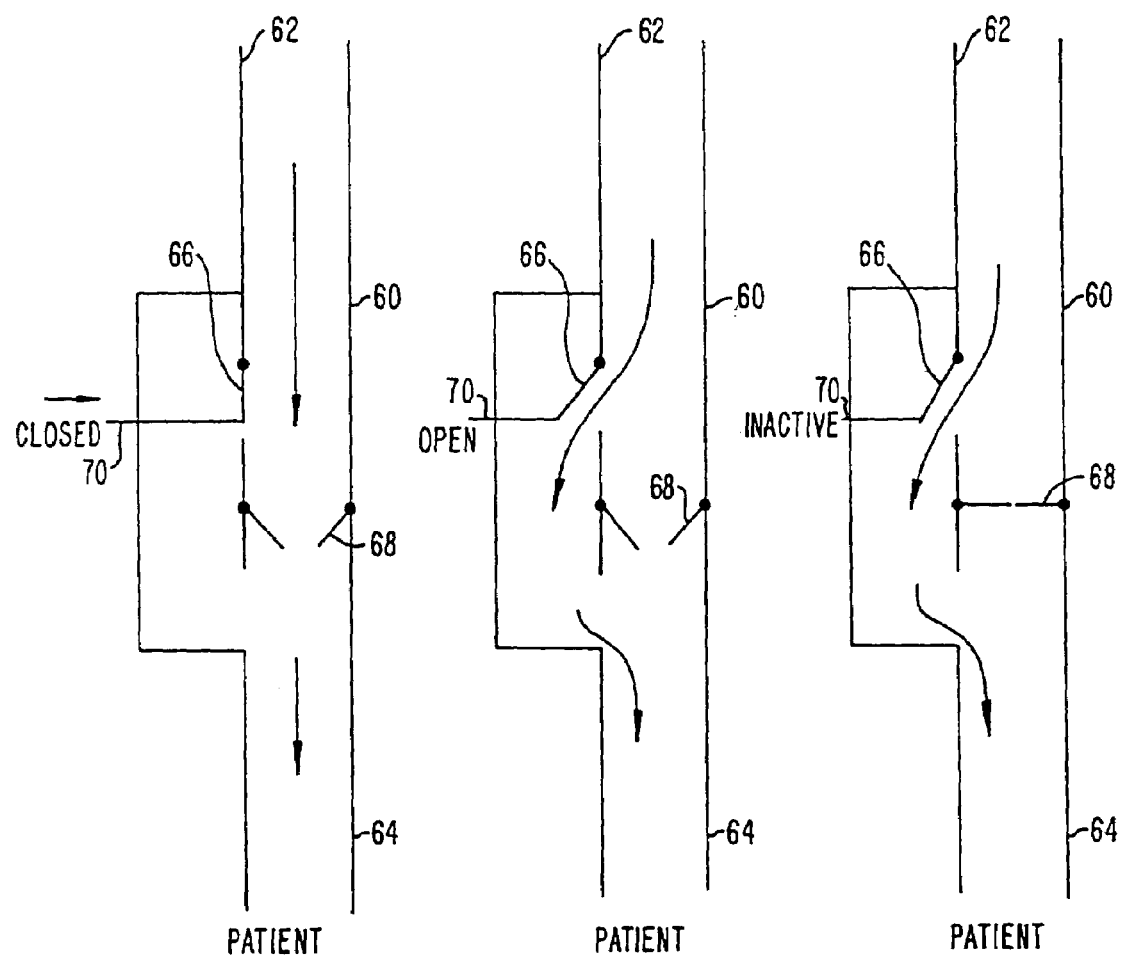
FIGS. 10A–10C are schematic views illustrating another embodiment of the present invention allowing for periodic patient ventilation through a bypassing valve.

FIGS. 10A–10C show another embodiment of the present invention which allows the patient to be ventilated by bypassing the impeding step. The embodiment comprises a ventilation tube 60 with a proximal end 62 and a distal end 64 that is connected to the patient. The ventilation tube 60 has a one-way bypass valve 66 and a one-way pressure responsive valve 68. The ventilation tube 60 may also have a manual switch 70 attached to the bypass valve 66 and extending through a side of the ventilation tube 60. As shown in FIG. 10A, the switch 70 may be set in a closed position so that the one-way pressure responsive valve 68 opens when the threshold pressure of the valve 68 has been exceeded. At this point, the valve 68 opens allowing for ventilation of the patient. As shown in FIG. 10B, the one-way pressure responsive valve 68 may be bypassed altogether by manually placing the switch 70 in the open position so that the bypass valve 66 is opened allowing air to flow to the patient. FIG. 10C illustrates the operation of the bypass valve 66 with the switch 70 in an inactive mode. Here, the rescuer performing ventilation may do so without added resistance from the impedance step as in FIG. 10A. Instead, bypass valve 66 opens only when the pressure at the proximal end of the tube 62 is greater than atmospheric pressure (0 mmHg), preferably in a range from about 0 mmHg to 5 mmHg. During decompression of the patient's chest, the one-way bypass valve 66 remains closed unless atmospheric pressure is exceeded. Thus, the patient is ventilated only when the rescuer performing ventilation causes the pressure at the proximal end of the tube 62 to exceed atmospheric pressure. The function of the one-way bypass valve 66 may be performed by many different threshold valve designs which are known in the art.

In another aspect of the invention, an exemplary valving system is provided for enhancing the duration and extent of negative intrathoracic pressure during the decompression phase of CPR while still providing adequate ventilation to the patient. The valving system is employed to slow the rapid equilibrium of intrathoracic pressure in the chest during decompression by impeding or inhibiting the flow of air into the patient's chest. Lowering of the intrathoracic pressure in this manner provides a greater coronary perfusion pressure and hence forces more venous blood into the thorax. The valving system can be employed in a variety of CPR methods where intrathoracic pressures are intentionally manipulated to improve cardiopulmonary circulation, including "vest" CPR, CPR incorporating a Heimlich ventilatory system, intraposed abdominal compression-decompression CPR, standard manual CPR, and the like, and will find its greatest use with ACD-CPR.

Referring to FIGS. 11–15, an exemplary embodiment of a valving system 100 is shown schematically. The valving system 100 includes a housing 101 having an upstream region 102 and a downstream region 104. Held between the upstream region 102 and downstream region 104 is a diaphragm 106. The diaphragm 106 is preferably a flexible or elastomeric membrane that is held over the downstream region 104 to inhibit air from flowing from the upstream region 102 to the downstream region 104 when the pressure in the downstream region 104 is less than the pressure in the upstream region 102, except when positive pressure, i.e. greater than atmospheric, is developed in the upstream region 102 when ventilating the patient. The valving system 100 further includes a valve 108 having a plug 110. As described in greater detail hereinafter, the valve 108 is included to provide ventilation to the patient when opened. The valve 108 can be manually opened by axial translation or it can be automatically opened when the pressure in the downstream region 104 reaches or exceeds a threshold amount, or both. Included at the upstream region 102 is an air intake opening 112 and an air exhaust opening 114. Air is delivered into the housing 101 through the air intake opening 112, while air is exhausted from the housing 101 through the air exhaust opening 114. An accordion valve 116, fish mouth valve, or the like is provided between the air intake opening 112 and the air exhaust opening 114. As described in greater detail hereinafter, the accordion valve 116 is used to prevent air that is injected into the air intake opening 112 from exiting the air exhaust opening 114 when ventilating the patient. A filter 117 is provided for filtering air injected into the housing 101. Optionally, a filter 119 can be provided in the downstream region 104 for preventing excess body fluids and air-borne pathogens from entering into the system 100.

Figure 11:
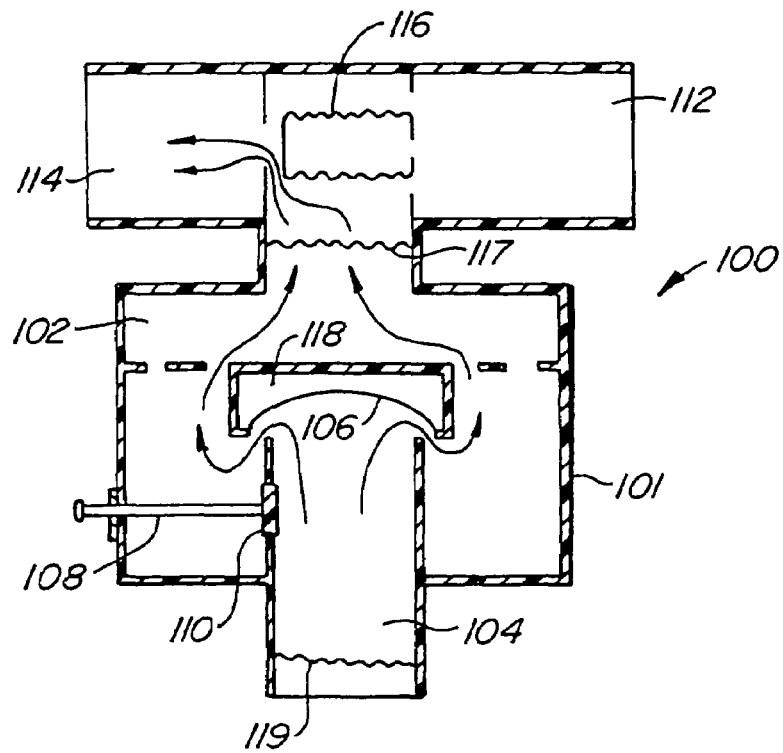
FIG. 11 is a schematic view of an exemplary valving system for regulating airflow into a patient's lungs according to the present invention. The valving system is shown with air being exhausted from a patient's lungs.

Operation of the valving system 100 during compression of a patient's chest is illustrated in FIG. 11. As the patient's chest is compressed, air is forced from the patient's lungs and into the downstream region 104. The air forced into the downstream region 104 is directed against the diaphragm 106 forcing the diaphragm into an ambient pressure region 118. Air in the downstream region 104 is then allowed to escape into the upstream region 102 where it is exhausted through the air exhaust opening 114. Optionally, the diaphragm 106 can be biased so that it will not be forced into the ambient pressure region 118 until the pressure within the downstream region 104 is about 2 cm $H_2O$ or greater, and more preferably at about 2 cm $H_2O$ to 4 cm $H_2O$.

Figure 12:
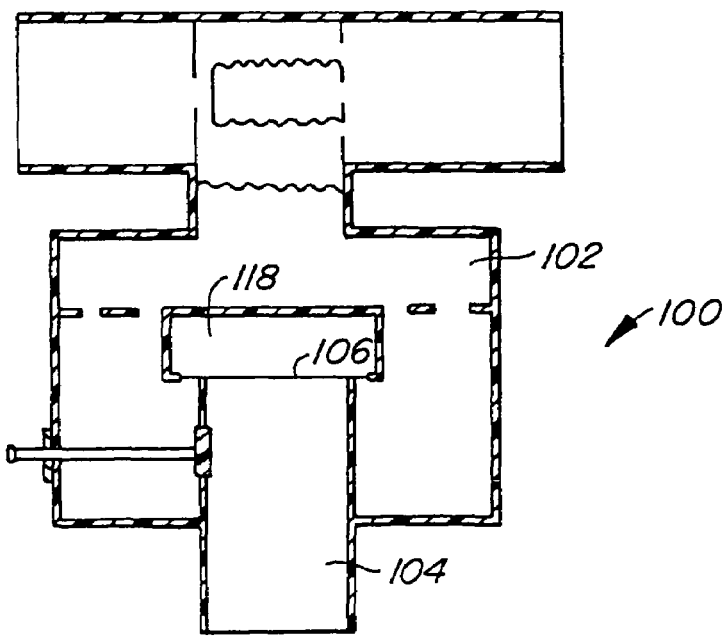
FIG. 12 illustrates the valving system of FIG. 11 during decompression or resting of the patient's chest.

Operation of the valving system 100 during decompression (or resting) of the patient's chest is illustrated in FIG. 12. As the patient's chest is actively lifted (or allowed to expand on its own), air is drawn from the downstream region 104 and into the patient's lungs, thereby reducing the pressure in the downstream region 104. The resulting pressure differential between the regions 102, 104 holds the diaphragm 106 over the downstream region 104 to prevent air from the upstream region 102 from flowing to the downstream region 104. In this way, air is inhibited from flowing into the patient's lungs during decompression of the patient's chest, thereby lowering the intrathoracic pressure to increase the coronary perfusion pressure and to force more venous blood into the thorax.

Figure 13:
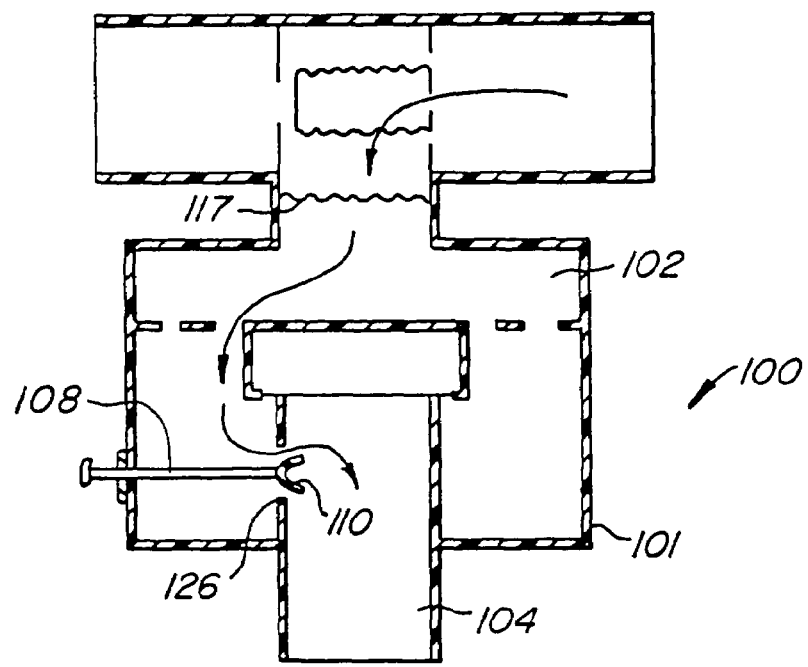
FIG. 13 illustrates the valving system of FIG. 11 with a pressure-responsive valve being opened when the negative intrathoracic pressure in the patient's chest exceeds a threshold amount during decompression of the patient's chest.
Figure 14:
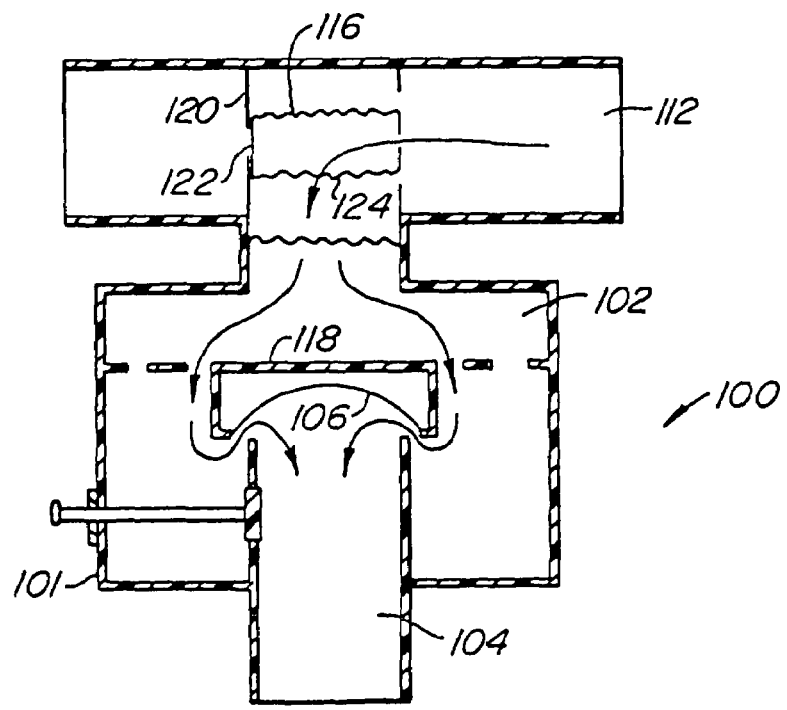
FIG. 14 illustrates the valving system of FIG. 11 with a diaphragm being opened during injection of air into the housing when ventilating the patient.
Figure 15:
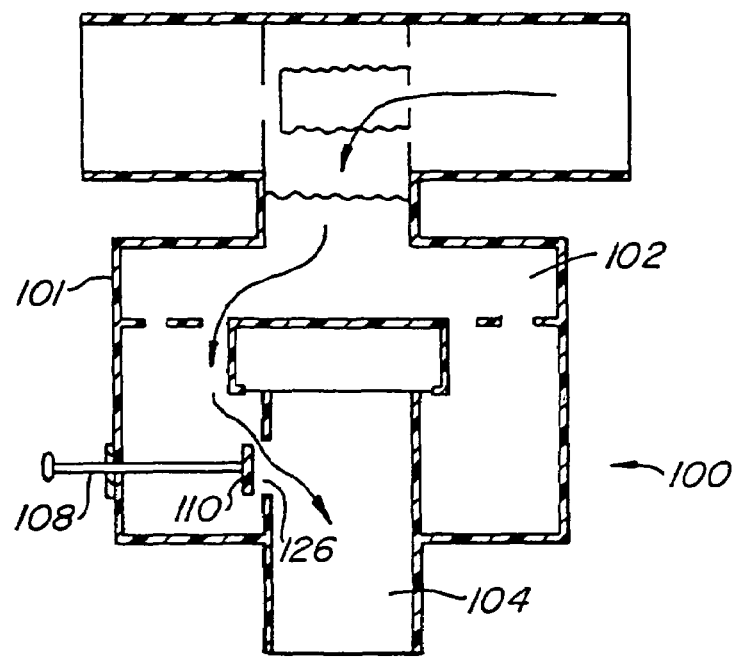
FIG. 15 illustrates the valving system of FIG. 11 with a manually operable valve being opened to allow air into the patient's lungs upon return of spontaneous circulation.

Various ways of providing ventilation to the patient using the valving system 100 are described in FIGS. 13–15. FIG. 13 illustrates airflow into the downstream region 104 and to the patient's lungs during decompression of the patient's chest after a threshold amount of negative intrathoracic pressure has been reached. Ventilation in this manner is advantageous in that the valving system 100 can be employed to produce at least a threshold amount of intrathoracic pressure to enhance blood flow into the heart and lungs. Once such as pressure is reached, some air is allowed to flow to the patient's lungs to ventilate the patient.

Air is allowed to enter the downstream region 104 when the threshold amount of intrathoracic pressure is reached by configuring the valve 108 to be a threshold valve. The valve 108 can be configured in a variety of ways, with a primary function being that the valve 108 allows air to flow into the downstream region 104 when a threshold amount of intrathoracic pressure is reached. This is preferably accomplished by configuring the plug 110 to be flexible in one direction so that when the pressure in the downstream region 104 reaches or exceeds the threshold amount, the plug 110 is flexed to provide an opening 126 between the upstream region 102 and downstream region 104. When the plug 110 is flexed, air flows from the lower pressure upstream region 102 into the downstream region 104 and to the patient's lungs. The plug 110 therefore acts as a one-way valve allowing air to flow from the upstream region 102 into the downstream region 104 when the threshold amount is reached, but does not allow airflow from the downstream region 104 to the upstream region 102. Preferably, the plug 110 will flex to open when the pressure within the downstream region 104 is in the range from about 0 mm $H_2O$ to 50 cm $H_2O$, more preferably at about 10 cm $H_2O$ to 40 cm $H_2O$, and more preferably at 15 cm $H_2O$ to about 20 cm $H_2O$. Alternatively, the valve 108 can be placed in the downstream region 104 so that air flows into the downstream region 104 directly from the atmosphere when the valve 108 is open. Although shown as a flexible plug, it will be appreciated that other types of valve arrangements may be used. For example, plug 110 could be replaced with a spring biased valve that closes opening 126 until the negative intrathoracic pressure overcomes the force of the spring to open the valve in a manner similar to that described in connection with FIG. 16A.

Ventilating the patient by injecting air into the upstream region 102 is illustrated in FIG. 14. As air is injected through the intake opening 112, it passes into the accordion valve 116 and forces the valve 116 against a wall 120 and covers a hole 122 in the wall 120 to prevent airflow through the exhaust opening 114. When the accordion valve 116 is closed, air flows through a wall 124 of the valve 116 and into the upstream region 102. Alternatively, a fish mouth valve can be used in place of the accordion valve 116. Upon injection of the air into the upstream region 102, the pressure within the upstream region 102 becomes greater than the pressure in the ambient pressure region 118 and causes the diaphragm 106 to be drawn into the ambient pressure region 118. An opening between the upstream region 102 and the downstream region 104 is created allowing air to flow into the downstream region 104 and into the patient's lungs. Preferably, the patient will be manually ventilated by injecting air into the intake opening 112 one time every five compressions of the chest, and more preferably about two times every 15 compressions of the chest using two rescuers. Similarly, ventilating the patient can occur through the same port where the spring-biased valve is located, such as through valve 160 of FIG. 16A.

Configuration of the valving system 100 upon return of spontaneous circulation is illustrated in FIG. 15. When the patient's circulation is restored, the valve 108 is manually opened by translating the valve 108 to remove the plug 110 from aperture 126. The upstream region 102 and downstream region 104 are then placed in communication to allow air to be freely exchanged between each of the regions 102, 104. Although shown extending through the upstream region 102, the valve 108 can alternatively be placed anywhere along the downstream region 104.

The valve 108 can be configured as a pressure-responsive valve (see FIG. 13), as a manually operable valve (see FIG. 15), or both. Further, the valving system 100 can alternatively be provided with two or more valves that are similar to the valve 108. For example, one valve could be non-translatably held in the housing 101 and provided with a pressure-responsive plug 110, with the other valve being translatably mounted. In this manner, the valve with the flexible plug functions as a pressure-responsive valve and opens when the threshold pressure is reached, while the translatable valve functions to place the regions 102, 104 in communication upon manual operation after spontaneous circulation is achieved.

Figure 16A:
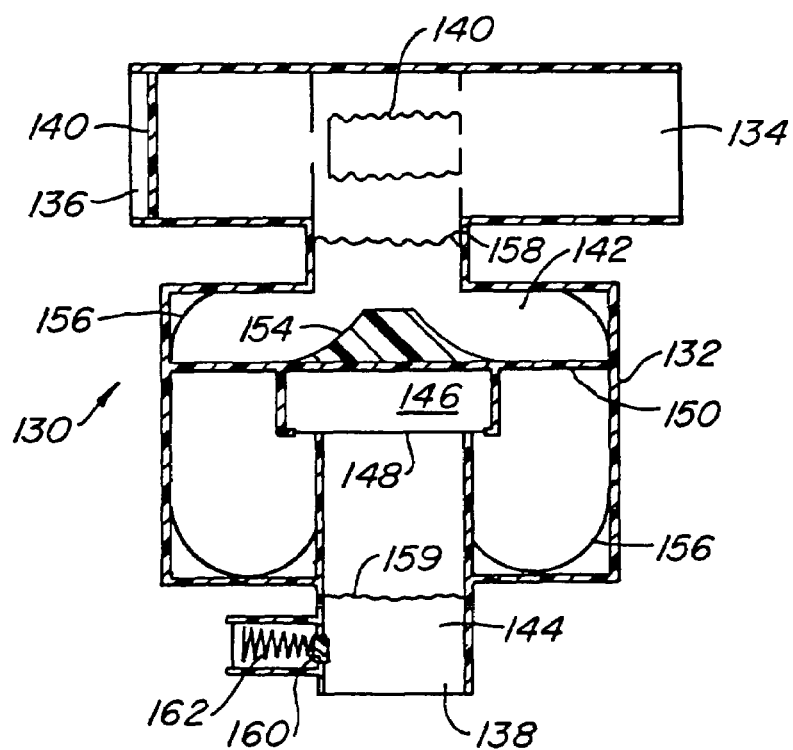
FIG. 16A is a cutaway side view of exemplary valving system according to the present invention.
Figure 16B:
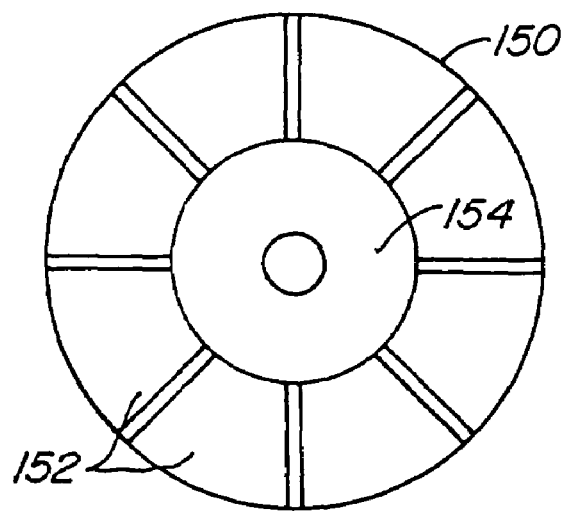
FIG. 16B is a top view of a deflector and a fenestrated mount of the valving system of FIG. 16A.

Referring to FIGS. 16A and 16B, an exemplary embodiment of a valving system 130 will be described. The valving system 130 is constructed of a housing 132 having an intake opening 134, an exhaust opening 136, and a delivery opening 138. Included in the exhaust opening 136 is a one-way valve 140 which allows air to flow from the housing 132 and out the exhaust opening 136. An accordion valve 140 is provided between the intake opening 134 and an exhaust opening 136 to prevent air injected into the intake opening 134 from exiting through the exhaust opening 136. Preferably, the intake opening 134 is configured to be attachable to a respiratory device, such as a respiratory bag (including an AMBU bag), a ventilator, a mouthpiece or port for mouth-to-mouth breathing through the system 130, or the like. The delivery opening 138 is preferably configured for connection to an endotracheal tube or other airway tube, a sealed facial mask, a laryngeal mask, or the like.

Within the housing 132 is an upstream region 142, a downstream region 144, and an ambient pressure region 146. Separating the upstream region 142 from the downstream region 144 is a diaphragm 148. The diaphragm 148 is preferably constructed of an elastomeric material. The housing 132 is preferably cylindrical in geometry at the downstream region 144, with the diaphragm 148 resting on the cylinder during ambient conditions. During decompression of the patient's chest, the reduction in pressure in the downstream region 144 draws the diaphragm 148 against the end of the cylinder to prevent exchange of air between the upstream region 142 and downstream region 144. During compression of the patient's chest, air is forced into the downstream region 144 to force the diaphragm 148 into the ambient pressure region 146 so that the air exhausted from the patient's chest can be exhausted through the exhaust opening 136.

As shown best in FIG. 16B, the valving system 130 is further provided with a fenestrated mount 150. In one aspect, the fenestrated mount 150 serves as a mount for holding the diaphragm 148 over the downstream region 144. The fenestrated mount 150 further provides the ambient pressure region 146. Fenestrations 152 are provided in the mount 150 to allow air to be exchanged through the mount 150. Included on the mount 150 is a deflector 154 for deflecting air around the fenestrated mount 150. Various other deflectors 156 are provided in the housing 132 for directing airflows between the regions 142 and 144. A filter 158 is provided in the housing 132 to filter air injected into the housing 132. Optionally, a filter 159 can be provided to prevent excess body fluids from entering into the system 130.

Figure 16C:
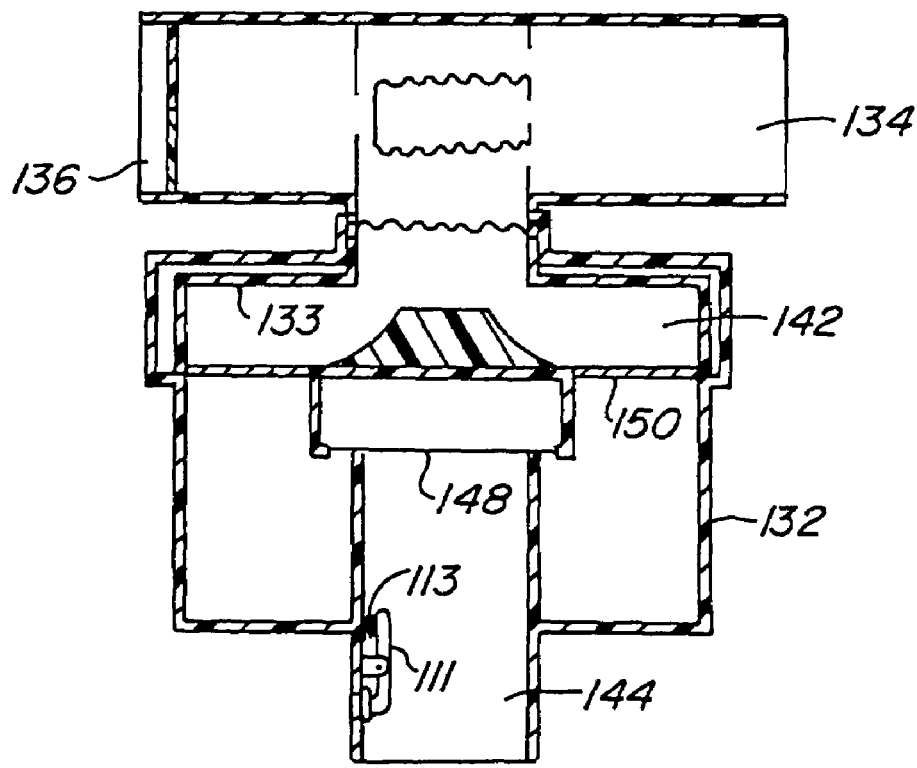
FIG. 16C is an alternative embodiment of the valving system of FIG. 16A.

The valving system 130 further includes a threshold valve 160 at the downstream region 144. When the pressure within the downstream region 144 is less than the threshold amount, the threshold valve 160 is opened to allow air to flow into the downstream region 144. The threshold valve 160 includes a spring 162 which is configured to extend when the threshold amount is reached. Alternatively, the threshold valve 160 can be configured similar to the valve 110. Other configurations which allow the for air to enter the downstream region 144 when the desired intrathoracic pressure is reached or exceeded can also be provided. For example, in a further alternative, the diaphragm 148 can be constructed to function as a threshold valve to allow air to flow into the patient's lungs when a threshold amount of intrathoracic pressure is reached. The diaphragm 148 can be fashioned as a threshold valve by constructing the diaphragm 148 of an elastomeric material and by providing at least one hole near the periphery. When the diaphragm rests on the cylinder forming the downstream region 144, the hole is positioned beyond the periphery of the cylinder and in the upstream region 142. As a vacuum is created in the downstream region 144, the diaphragm is drawn into the downstream region 144 until the hole is stretched over the cylinder and overlaps with both the upstream region 142 and the downstream region 144. In this way, a fluid path is provided between the regions 142 and 144 when the threshold pressure is reached in the downstream region 144. Another alternative of a threshold valve 111 is illustrated in FIG. 16C. The valve 111 is pivot mounted within the downstream region 144 and is biased closed by a spring 113. When the threshold pressure within the downstream region 144 is reached, the spring 113 is compressed and air is drawn into the downstream region 144.

Referring back to FIG. 16A, the threshold valve 160 can optionally be provided within the housing 132 at the upstream region 142. The threshold valve 160 can further optionally be provided with an on/off switch for opening the valve 160 when spontaneous circulation is achieved. In this manner, a rescuer can open the valve 160 to allow for free exchange of air to the patient's lungs when needed. In one alternative as shown in FIG. 16C, the mount 150 can be slidably mounted within the housing 132 so that the mount 150 can be vertically raised to lift the diaphragm 148 from the downstream region 144 upon successful resuscitation of the patient, thereby providing a free flow of air to the patient. The mount 150 can be slidably mounted within the housing 132 by attaching the mount 150 to an extension member 133 that is slidable within the housing 132. The member 133 preferably includes the intake and exhaust openings 134 and 136. In this way, an easy grasping surface is provided when translating the member 133 to open or close the diaphragm 148. If the diaphragm 148 were also fashioned as a threshold valve as previously described, the need for the valves 108 or 111 could be eliminated.

The housing 132 can conveniently be constructed in several parts which are connected together at various connection points. In this manner, the housing can be taken apart for connection to other devices, for repair, for cleaning, and the like. For example, one connection point can be conveniently provided near the filter 158 for removably connecting the portion of the housing having the intake opening 134, the valve 140, and the exhaust opening 136. Alternatively, a connection point can be provided near the mount 150 to provide easy access to the mount 150 for cleaning.

The valving system 130 can conveniently be incorporated with a variety of devices useful in CPR procedures. For example, the valving system 130 can be incorporated within a respiratory bag, such as an AMBU bag. Alternatively, the valving system 130 can be included as part of a respiratory circuit having both a respiratory bag and an endotracheal tube or other airway tube, with the valving system 130 positioned between the bag and the tube. In further alternative, the valving system 130 can be added to an endotracheal tube alone. Alternatively, the valving system can be incorporated into a mask, an oralpharyngeal airway, a laryngeal mask or other ventilatory devices.

Figure 16D:
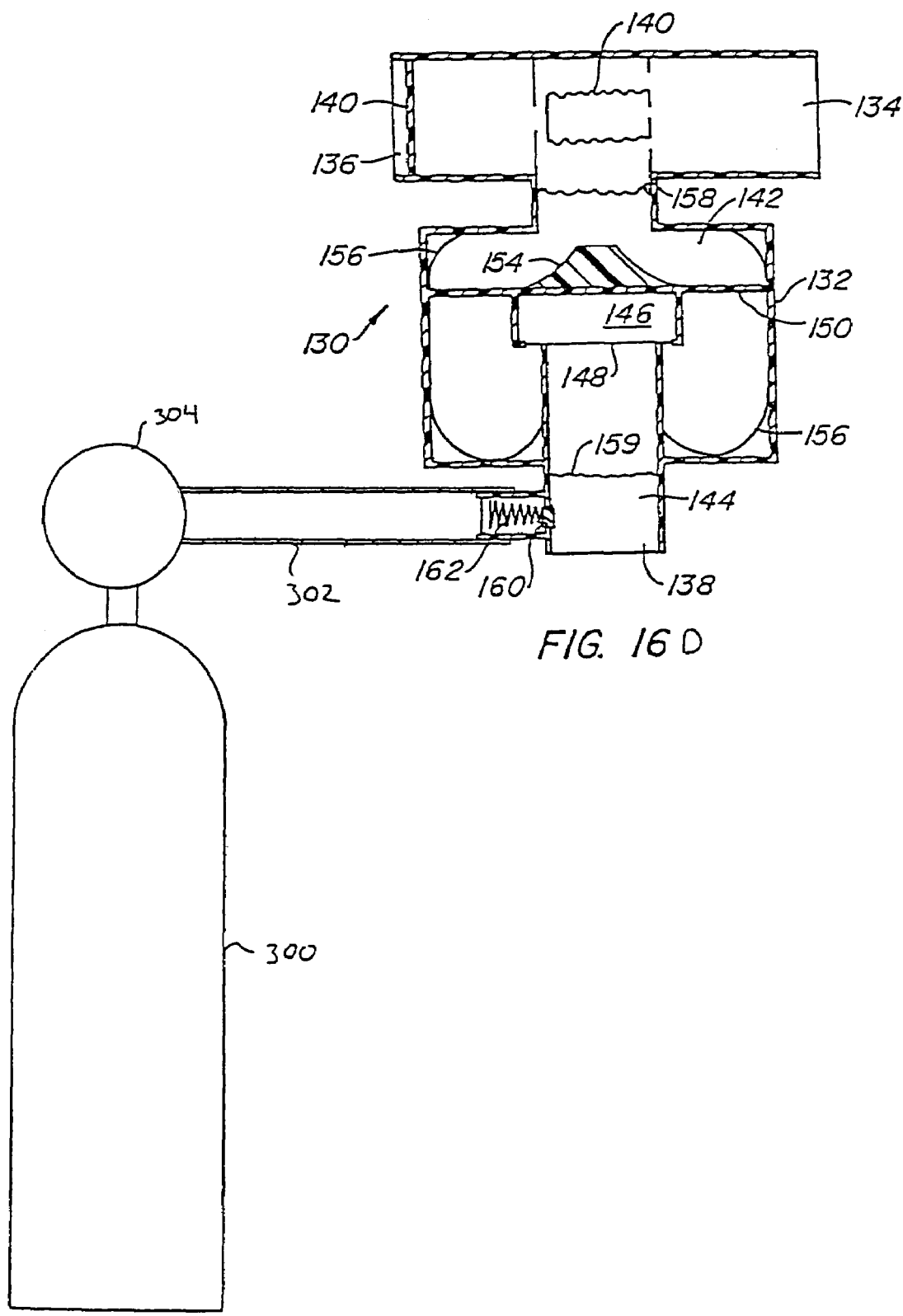
FIG. 16D illustrates the valving system of FIG. 16A with a source of pressurized gas coupled to a pressure-responsive valve according to the invention.

In some cases, patient ventilation may be provided through threshold valve 160 as shown in FIG. 16D. In such a case, intake opening and valve 140 are optional since all ventilation may occur through threshold valve 160. Of course, ventilation could be provided through both avenues. Further, although shown in the context of valving system 130, it will be appreciated that the other embodiments described herein may be modified to include a pressure source that is coupled to the threshold valve.

As shown in FIG. 16D, a tank 300 of pressurized gas, such as $O_2$ is coupled to housing 132 by a length of tubing 302. In this way, a pressurized gas may be supplied to the back side of threshold valve 160. A regulator 304 is coupled to tank 300 to regulate the pressure supplied to threshold valve 160 so that it is less than the pressure required to open valve 160. For example, if respiratory gases are to be supplied to the patient when the negative intrathoracic pressure exceeds −14 cm $H_2O$, then the actuating valve pressure may be set at −14 cm $H_2O$, and the pressure of the gas from tank 300 may be set less than −14 cm $H_2O$. In this way, valve 160 will not prematurely open. In some cases, regulator 304 may also be used to regulate the flow rate of the gas through valve 160.

By coupling tank 300 to valve 160, respiratory gases are pulled into downstream region 144 when valve 160 opens due to the decrease in negative intrathoracic pressure as previously described. In this way, more respiratory gases are supplied to the patient each time the patient's chest is decompressed. This approach allows for negative pressure ventilation, unlike positive pressure ventilation which impedes venous return to the chest with each active rescuer ventilation. The negative pressure ventilation with this approach allows for adequate oxygenation and maximum venous blood return during CPR. Tank 300 may also function to provide oxygen once the trigger pressure has been achieved.

Figure 17:
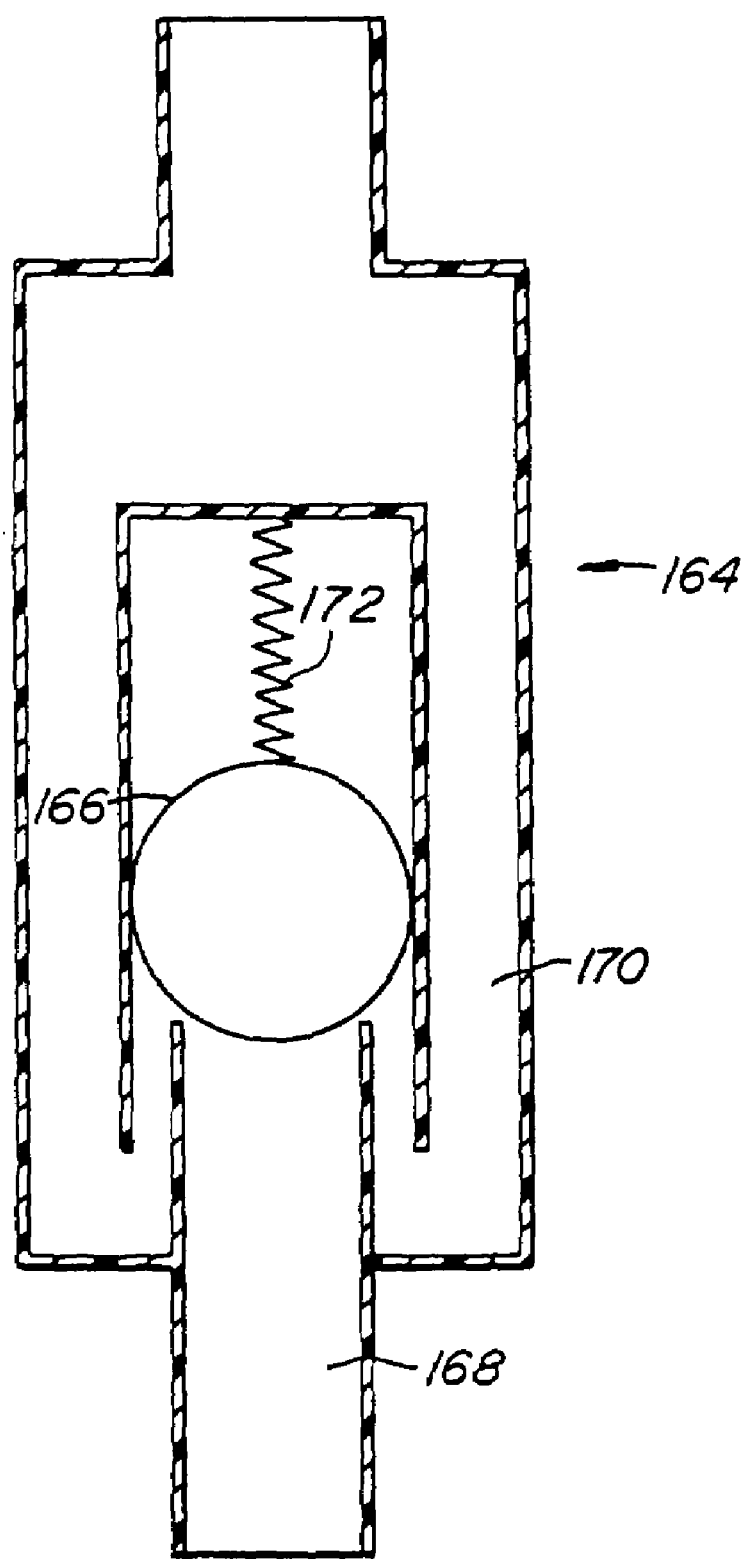
FIG. 17 is a schematic view of an alternative embodiment of a valving system having a ball as a diaphragm.

Referring to FIG. 17, an alternative valving system 164 will be described. The valving system 164 is shown schematically and operates essentially identical to the valving system 100, the difference being that the valving system 164 includes a ball or spherical member 166 as the diaphragm. During decompression of the patient's chest, the pressure in a downstream region 168 is less than the pressure in an upstream region 170 which draws the ball 166 over the downstream region 168. The valving system 164 can optionally be provided with a spring 172 or other biasing mechanism to hold the ball 166 over the downstream region 168 during compression of the patient's chest until a threshold pressure is reached or exceeded in the downstream region 168 as previously described.

Figure 18:
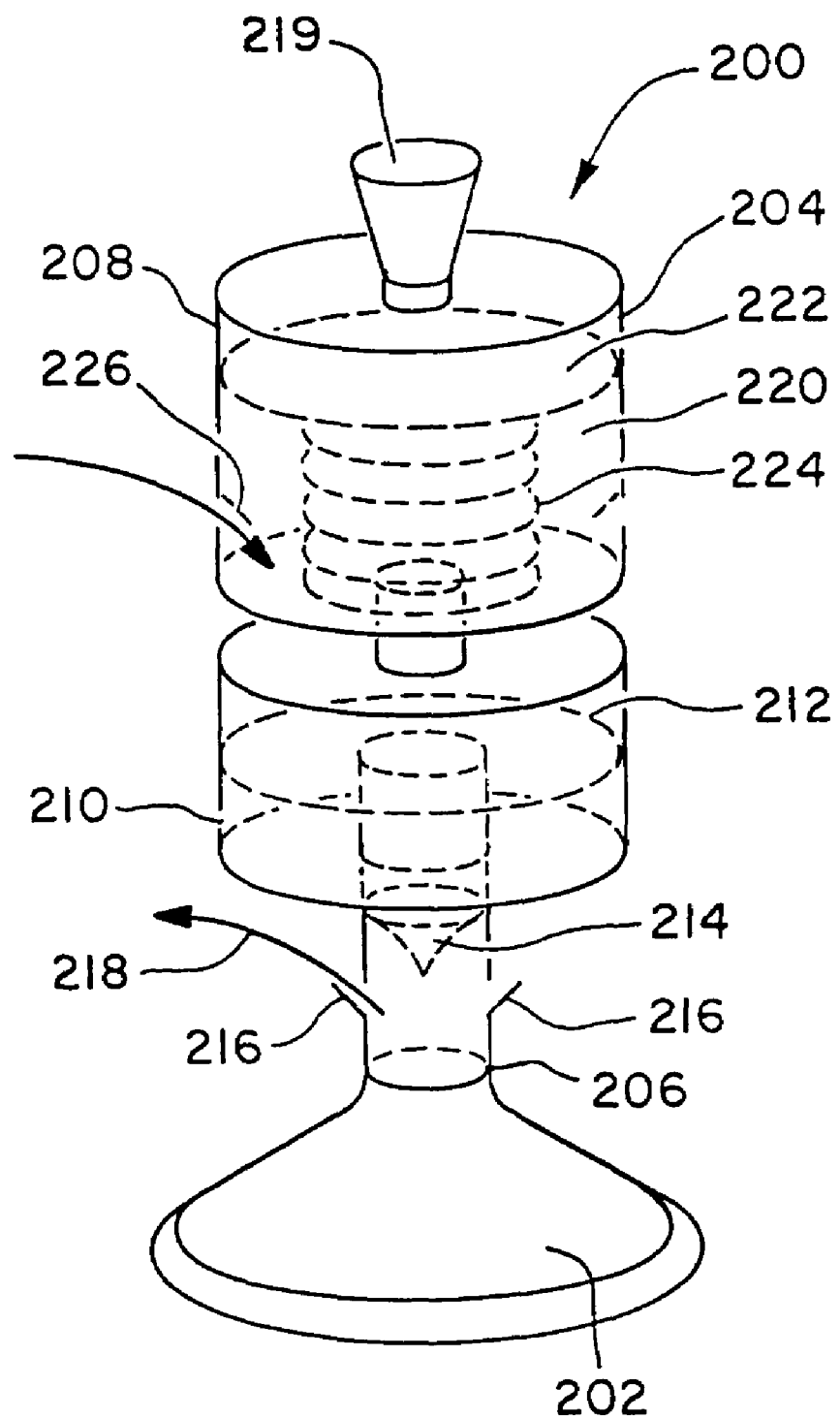
FIG. 18 is a schematic view of a device for impeding air flow into the patient's lungs and for providing air to the patient's lungs when needed for ventilation.

Referring now to FIG. 18, another exemplary device 200 which is useful when performing cardiopulmonary resuscitation will be described. As described in greater detail hereinafter, one important feature of device 200 is that it may be interfaced to the patient's airway to periodically supply air to the patient's lungs when performing cardiopulmonary resuscitation. In this way, the patient may be ventilated with air (or other desired gases, such as $O_2$) rather than with respiratory gases from the rescuer's lungs as is typically the case when performing mouth-to-mouth resuscitation.

Device 200 comprises a facial mask 202 and a housing 204 that is operably attached to facial mask 202 at an interface 206. Housing 204 includes an upper region 208 and a lower region 210. Lower region 210 includes a pressure responsive valving system 212 which operates in a manner similar to the embodiments previously described herein to prevent the flow of gases into the patient's lungs until a threshold negative intrathoracic pressure is exceeded. At this point, pressure responsive valving system 212 allows gases to flow into the patient's lungs in a manner similar to that previously described herein. Lower region 210 further includes a fish mouth valve 214 and one-way outflow valves 216. Valves 214 and 216 operate together to allow gases exhausted from the patient's lungs to exit device 200 as indicated by arrow 218. In particular, when gases are forced out of the patient's lungs, fish mouth valve 214 will be closed and the exhausted gases will escape from device 200 through valves 216.

Upper region 208 includes a mouth piece 219 to allow a rescuer to blow into device 200 when attempting to ventilate a patient (similar to conventional CPR). Upper region 208 defines an air chamber 220 for holding room air and has a volume of about 200 ml to about 800 ml. Chamber 200 may also be connected to an oxygen source. Disposed within upper region 208 is a diaphragm 222 and a spring 224. With this configuration, when a rescuer blows air into mouth piece 219, spring 224 will compress as diaphragm 222 moves downward. In turn, air or oxygen held within air chamber 220 will be compressed and hence forced through valving system 212 and into facial mask 202. In this way, air (rather than respiratory gases) from the rescuer will be supplied to the patient when the rescuer performs mouth-to-mouth resuscitation by blowing into mouth piece 219.

Upper region 208 further includes a one-way inflow valve 226 which allows air chamber 220 to be replenished with room air following ventilation. In particular, as spring 224 expands valve 226 will open to allow room air to fill chamber 230 due to the negative pressure created in chamber 230 by spring 224. Inflow valve 226 will also open when the threshold negative intrathoracic pressure is exceeded causing pressure responsive valving system 212 to open. In this way, inflow valve 226 also serves as a venting mechanism to vent air into housing 204 when the negative intrathoracic pressure limit is exceeded.

Hence, device 200 allows a rescuer to ventilate a patient with room air simply by blowing into mouth piece 219. Of course, it will appreciated that other desirable gases may be placed within air chamber 220 so that such gases may be supplied to the patient when the rescuer blows into mouth piece 219. For example, a volume of $O_2$ may be placed within chamber 220.

As previously described, one aspect of the invention is the ability to prevent respiratory gasses from entering the lungs until a certain negative intrathoracic pressure is met or exceeded. One aspect of the invention is the ability to vary the pressure at which respiratory gasses are permitted to flow to the lungs. In some cases, this may be accomplished by varying the actuating or cracking pressure of the pressure-responsive inflow valve. However, other mechanisms may be provided to vary the pressure at which respiratory gasses are permitted to flow to the lungs without modifying the cracking pressure of the pressure-responsive inflow valve. Hence, mechanisms for varying the pressure at which respiratory gasses are permitted to flow to the lungs may be incorporated in the pressure-responsive inflow valve, another valve in the valving system, or may be a separate part of the overall valving system.

Such a system may be configured so that the actuating pressure may vary between about 0 cm $H_2O$ to about −30 cm $H_2O$. Further, such a valving system may be used alone with a spontaneous breathing patient or with a patient receiving standard manual closed-chest CPR. Such a valving system may also be used in conjunction with other resuscitation techniques and/or devices, including, for example, ACD CPR, Vest CPR, or the like. In some cases, such a valving system may be used in connection with a diaphragmatic stimulator for purposes of resuscitation from cardiac arrest as well as for increasing blood pressure by advancing venous return. Exemplary systems and techniques for diaphragmatic stimulation for purposes of resuscitation are described in U.S. patent application Ser. No. 09/095,916, filed Jun. 11, 1998; Ser. No. 09/197,286, filed Nov. 20, 1998; Ser. No. 09/315,396, filed May 20, 1999; and Ser. No. 09/533,880, filed Mar. 22, 2000, incorporated herein by reference. As a further example, such a valving system may be used to improve central blood return to the heart in patients in cardiac arrest, patients with low blood pressure and patients in right heart failure and in shock.

A variety of mechanisms may be used to vary the degree at which respiratory gasses are permitted to flow to the lungs. For example, such a mechanism may be mechanical or electronic or may include various combinations of mechanical and electronic components, and may be regulated within a larger system by, for example, electronic communication between the device used for resuscitation and the pressure-responsive inflow valve. Such a mechanism may also be adjustable based upon the in-line measurement of gasses, such as the measurement of end-tidal $CO_2$, the average minute ventilations, peak negative inspiratory pressures, and the like.

Figure 19:
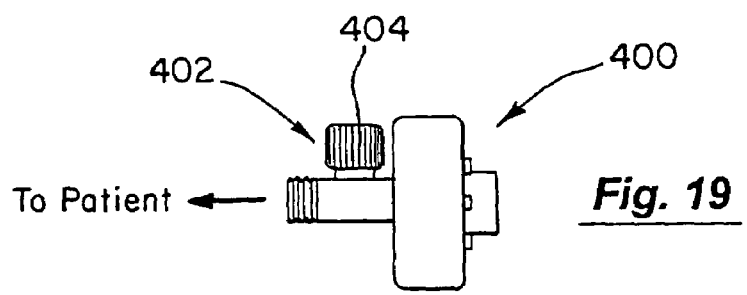
FIG. 19 is a side view of one embodiment of a valving system having an adjustable pressure responsive valve according to the invention.

Referring to FIG. 19, one embodiment of a valving system 400 having an adjustable pressure-responsive inflow valve 402 will be described. Valving system 400 is shown schematically and may be constructed similar to any of the embodiments described herein. As such, when valving system 400 is interfaced with a patient's airway, the patient may freely exhale through valving system 400. When attempting to inhale, or during a decompression step of CPR, respiratory gasses are prevented from entering the lungs until a threshold actuating pressure is reached. At such time, respiratory gasses are permitted to flow to the lungs through inflow valve 402 in a manner similar to that previously described with other embodiments.

Figure 20:
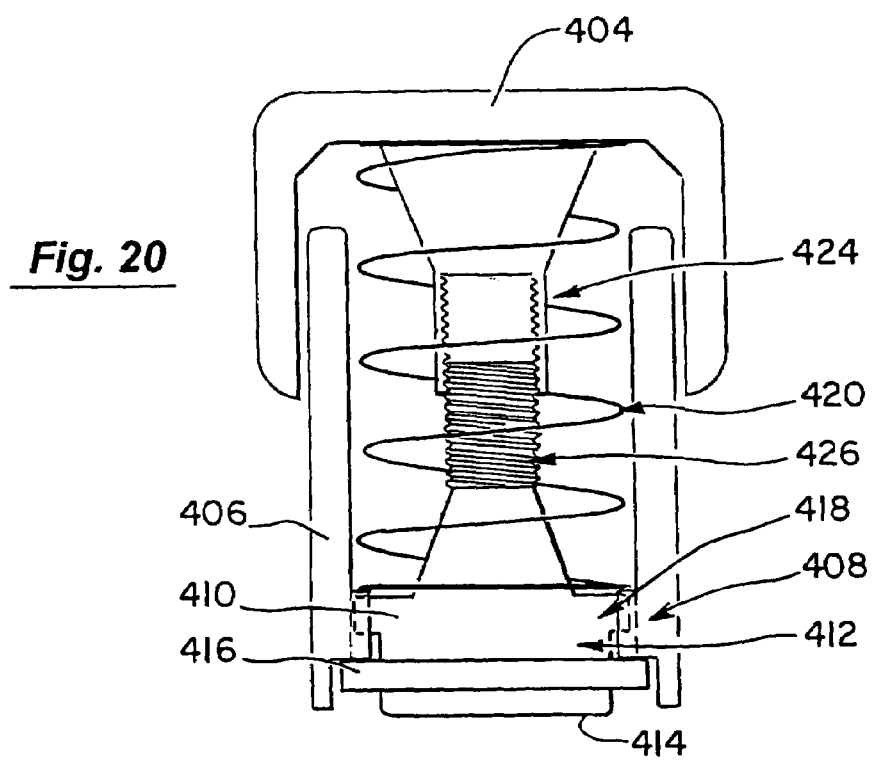
FIG. 20 is a cross sectional side view of the adjustable pressure responsive valve of FIG. 19.
Figure 21:
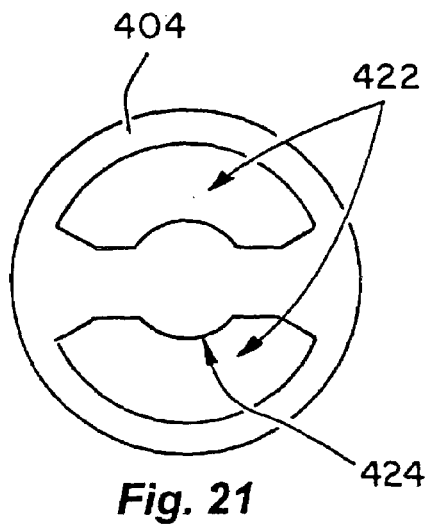
FIG. 21 is a top view of the valve of FIG. 20.
Figure 22:
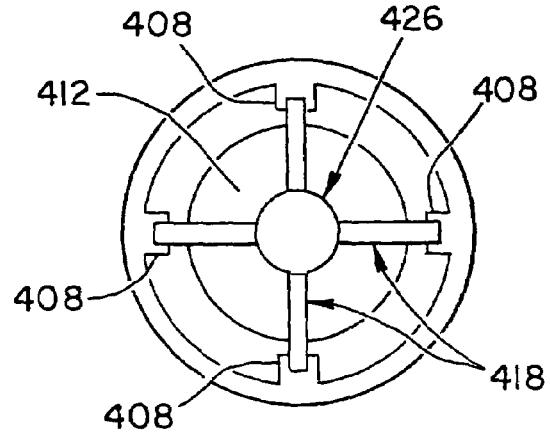
FIG. 22 illustrates the valve of FIG. 21 with a cap being removed.

Inflow valve 402 includes a tension adjust knob 404 that may be turned by the rescuer to adjust the threshold actuating pressure of inflow valve 402 and will be described in greater detail with reference to FIGS. 20–22. As best shown in FIG. 20, inflow valve 402 comprises an outer housing 406 having a set of tracking channels 408 (see FIG. 22). Outer housing 406 is configured to hold an O-ring housing 410 having a top segment 412 and a bottom segment 414. Disposed between top segment 412 and bottom segment 414 is an O-ring 416. Top segment 412 further includes a set of tracking rails 418 that slide within tracking channels 408. A tension spring 420 sits between tension adjust knob 404 and top segment 412 and biases O-ring 416 against outer housing 406. When O-ring 416 is biased against outer housing 406 the valve is in the closed position where respiratory gasses are prevented from passing through ventilation ports 422 and to the patient's lungs. When the negative intrathoracic pressure meets or exceeds the threshold actuating pressure of inflow valve 402, the tension in spring 420 is overcome, causing O-ring 416 to separate from outer housing 406. At this point, respiratory gasses are free to rush through ventilation ports 422 and to the patient's lungs.

To vary the actuating pressure of inflow valve 402, knob 404 is turned to advance or retract a threaded nut 424 along a threaded bolt 426 that in turn is coupled to top segment 412. In so doing, the tension of spring 420 is varied to vary the actuating pressure of inflow valve 402. Hence, knob 404 provides a convenient way for a rescuer to adjust the actuating pressure simply by turning knob 404. Although not shown, a pressure gauge may be disposed within valving system 400 and a display may be provided to display the negative intrathoracic pressure. In this way, the rescuer may readily visualize the pressures generated within valving system 400 and may adjust knob 404 to vary the pressure at which respiratory gasses are permitted to flow to the lungs.

Another feature of the invention is the use of a safety mechanism to permit respiratory gasses to freely flow to the patient through the valving system until the rescuer places the valving system in an operative mode. Once in the operative mode, the valving system will remain in that mode indefinitely or for a finite period of time, at which the safety mechanism would revert back to its initial state where respiratory gasses may freely flow to the lungs. In some embodiments, this may be accomplished by having the safety mechanism maintain the pressure responsive inflow valve in the open position (without any impedance to inspiratory air flow) until actuated by the rescuer. Actuation may be accomplished in a variety of ways, such as by injected respiratory gasses into the valving system (such as when ventilating the patient), by operating a button or switch on the valving system, or the like.

One advantage of such a safety mechanism is that it ensures that the patient can freely breathe through the valving system (assuming the patient is spontaneously breathing or begins to spontaneous breathe) without any resistance from the pressure-responsive inflow valve. Once the rescuer is ready to begin a procedure, such as performing CPR, the valving system is placed in the operative mode where respiratory gas flow to the lungs is prevented through the pressure-responsive inflow valve until the threshold negative intrathoracic pressure is met or exceeded. As with other embodiments described herein, respiratory gasses may also be injected into the patient's lungs through the valving system, thereby bypassing the pressure-responsive inflow valve.

The safety mechanism may operate as a purely mechanical device, a purely electronic device, or may include various combinations of mechanical and electronic components. One way for placing the valving system in the operative mode is by utilizing a sensor to detect when respiratory gasses are injected into the valving system through the ventilator port. The signal from the sensor may then be used to close a ventilation passage within the valving system. In some cases, the ventilation passage may extend through the pressure-responsive inflow valve. To close this passage, the inflow valve is simply closed. In some embodiments, if rescuer ventilation is not provided within a certain time, the safety mechanism may be used to take the valving system out of its operative mode so that respiratory gasses may freely flow to the patient's lungs.

Figure 23:
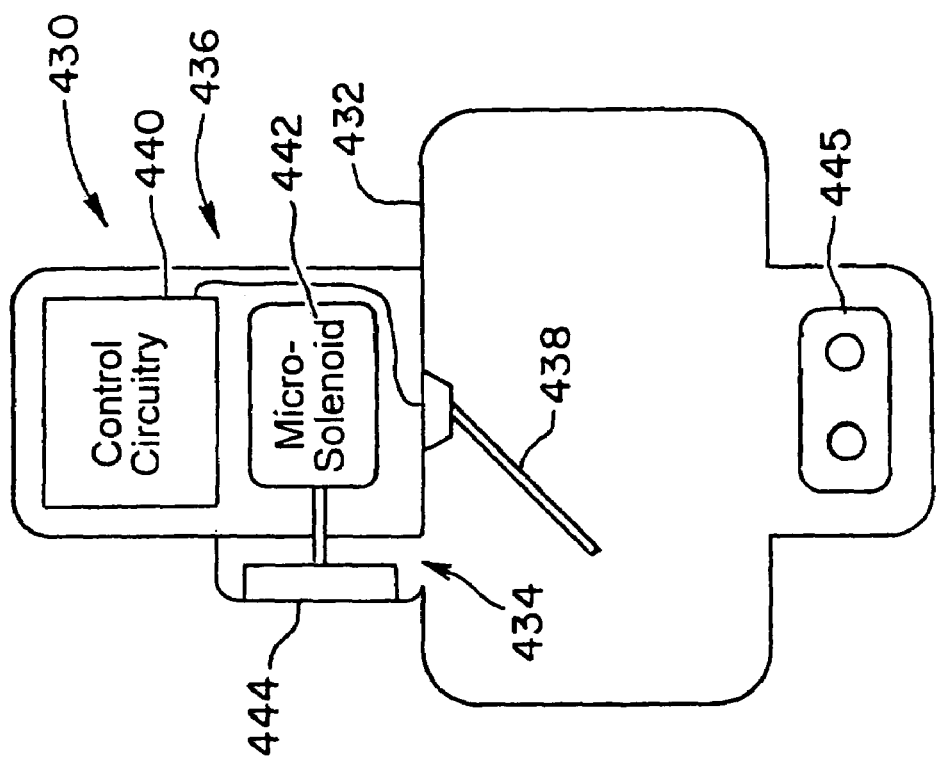
FIG. 23 is a schematic side view of a safety mechanism for a valving system that permits respiratory gases to freely flow to the patient's lungs through a ventilation passage according to the invention.
Figure 24:
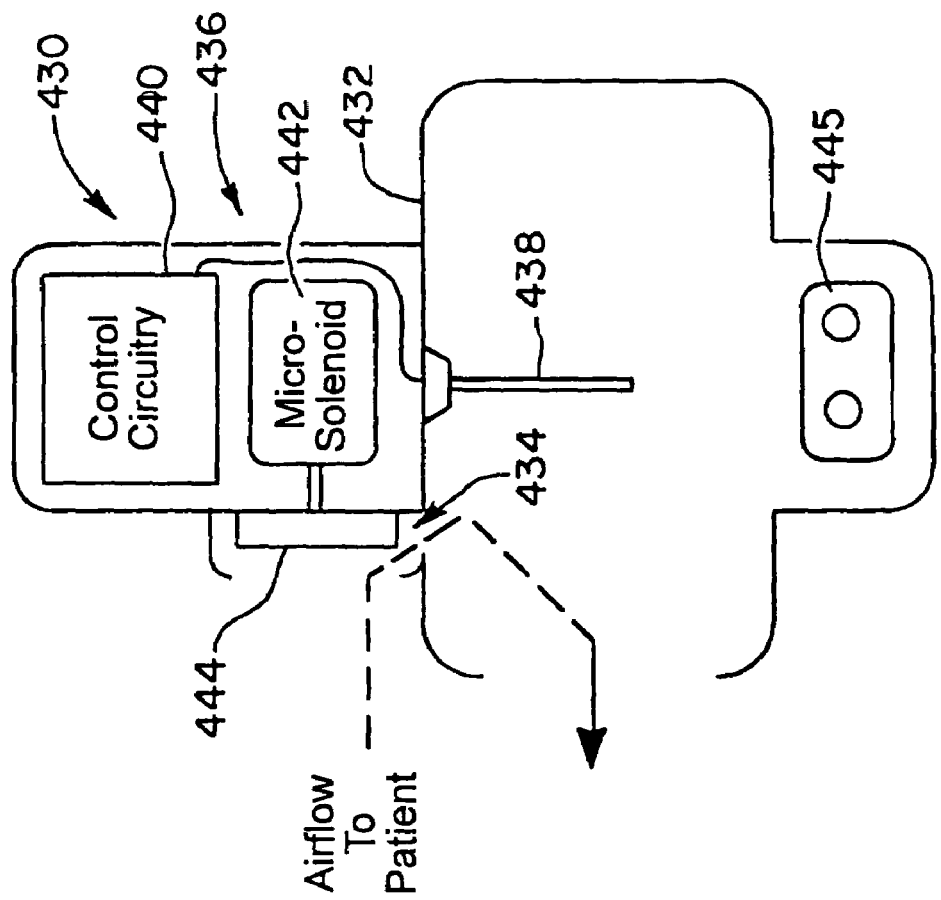
FIG. 24 illustrates the safety mechanism of FIG. 23 when actuated to prevent respiratory gases from flowing through the ventilation passage.

Referring now to FIGS. 23 and 24, one embodiment of a valving system 430 with such a safety feature will be described. This configuration may be used in series with any of the previously described valving systems so that it will have a means of impeding airflow to the patient's lungs.

Hence, it will be appreciated that valving system 430 may be constructed to have, or used in combination with, components similar to the other valving systems described herein and will not be illustrated to simplify discussion. Valving system 430 includes a housing 432 that may be similar to the housings of the other valving systems described herein except that housing 432 includes a safety ventilation port 434 that permits respiratory gasses to flow into and through housing 432 so that respiratory gasses may flow to the patient's lungs as shown by the dashed line in FIG. 23. Hence, as shown in FIG. 23, valving system 430 is in a passive mode where the patient may freely breathe through housing 432.

Valving system 430 further includes a safety mechanism 436 that is operative to maintain ventilation port 434 open until actuated by a rescuer. When actuated, safety mechanism 436 closes ventilation port 434 to place valving system 430 in the operative mode where respiratory gasses are prevented from reaching the lungs through a pressure-responsive inflow valve until a threshold negative intrathoracic pressure is met or exceeded in a manner similar to that described in other embodiments.

Safety mechanism 436 comprises an electronic air flow sensor 438 that is electrically connected to control circuitry 440. In turn, control circuitry 440 is electrically connected to a micro-solenoid 442 having a valve stop 444. A battery 445 is used to supply power to the electrical components. When a rescuer is ready to place valving system 430 in the operative mode, the rescuer injects respiratory gasses into housing 432 (such as by blowing air or injecting a pressurized gas into a ventilation port, not shown). As the respiratory gasses flow to the patient's lungs through housing 432, sensor 438 is moved to trigger a switch and to send an electrical signal to control circuitry 440. Control circuitry 440 then sends a signal to solenoid 442 to move stop 444 and thereby close the valve, thus preventing airflow to the patient through safety ventilation port 434. Such a state is illustrated in FIG. 24 where valving system 430 is in the operative mode. At this point, a spontaneously breathing patient will need to breathe through a pressure-responsive inflow valve. For a non-breathing patient, respiratory gasses will be prevented from reaching the lungs during the performance of CPR until a threshold negative intrathoracic pressure is overcome, at which point respiratory gasses may flow through the inflow valve and to the patient's lungs in a manner similar to that described with other embodiments. If, after a certain time, sensor 438 is not actuated by the rescuer, control circuitry 440 may be configured to operate solenoid 442 to take valving system 430 out of the operative mode where respiratory gasses may flow through safety ventilation port 434.

In some embodiments, the valving systems of the invention may incorporate a safety mechanism having essentially all mechanical elements. One such embodiment of a valving system 480 is illustrated in FIGS. 25 through 33 and 36 through 40. Valving system 480 comprises a housing 482 that houses various components that may be similar to the other embodiments described herein. As such, housing 482 includes a ventilation port 484 and an exit opening 486. Valving system 480 further includes a pressure-responsive inflow valve 488 that prevents respiratory gasses from flowing to the patient's lungs until a certain negative intrathoracic pressure level has been met or exceeded in a manner similar to that described with other embodiments. Valving system 480 further includes a safety mechanism 490 to permit respiratory gasses to freely flow to the patient's lungs until operated to place valving system 480 in an operative mode where pressure-responsive inflow valve 488 controls when respiratory gasses are permitted to flow to the lungs. As described in greater detail hereinafter, safety mechanism 490 also includes an inflow valve 492. In some embodiments, inflow valve 492 may be configured as a pressure-responsive inflow valve and thereby eliminate the need for inflow valve 488.

Figure 25:
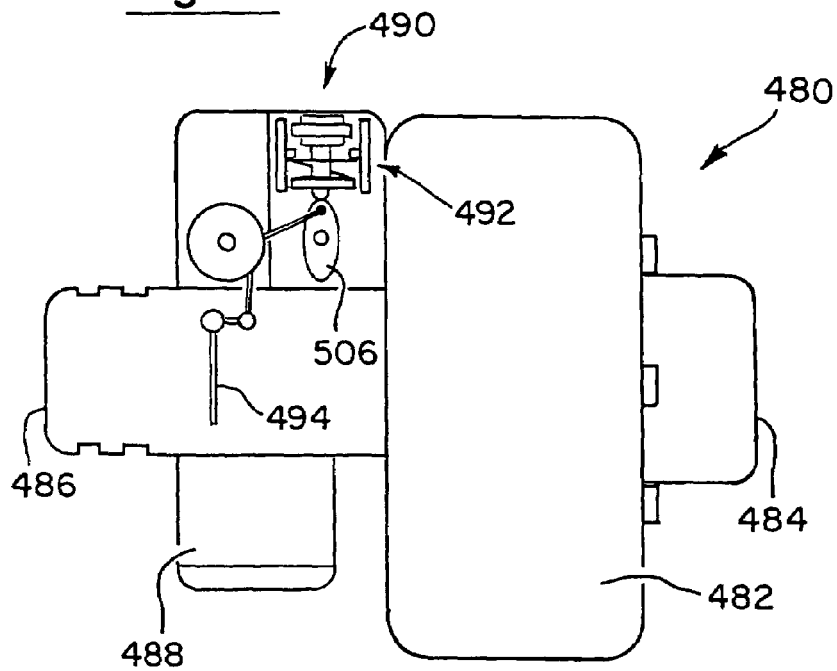
FIG. 25 is a schematic side view of a valving system having an integrated safety mechanism that permits respiratory gases to freely flow to the patient's lungs through an inflow valve according to the invention.
Figure 26:
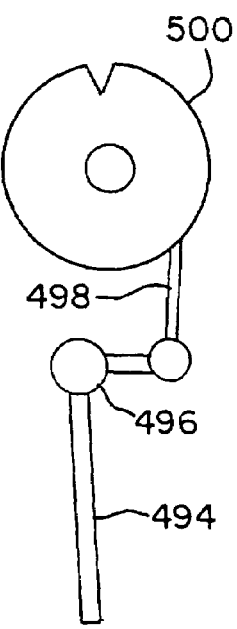
FIG. 26 illustrates a flow sensor and lever arm of the safety mechanism of FIG. 25 prior to actuation by the rescuer.
Figure 27:
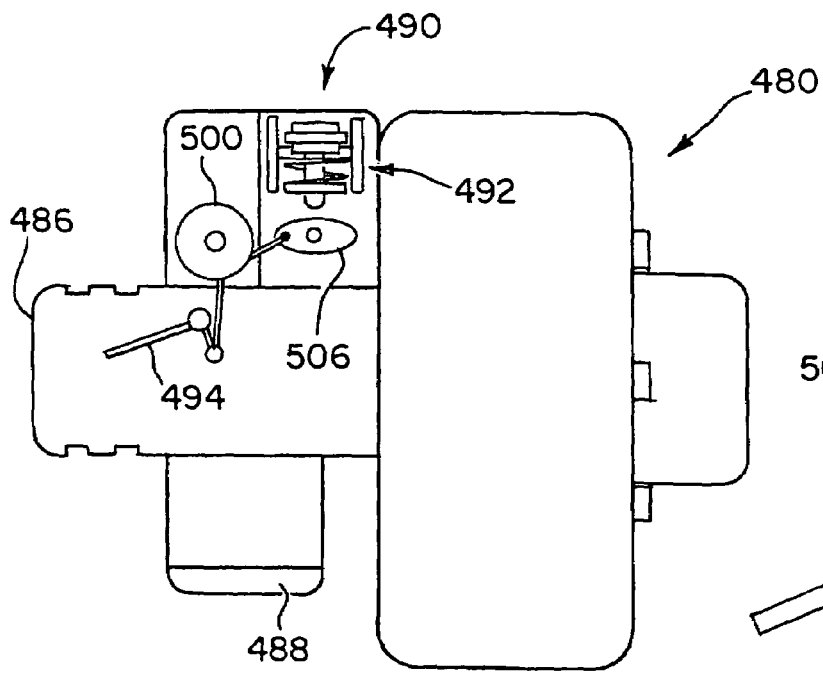
FIG. 27 illustrates the valving system of FIG. 25 when the safety mechanism is actuated by the rescuer to closed the inflow valve.
Figure 28:
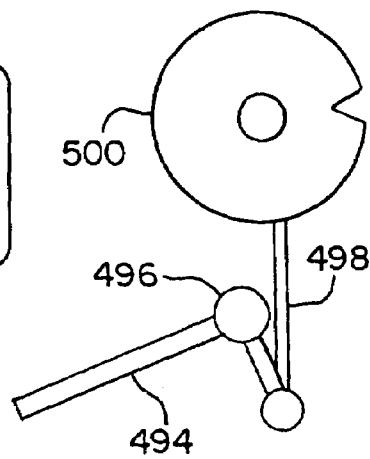
FIG. 28 illustrates the flow sensor and lever arm of FIG. 26 when actuated by the rescuer.

Safety mechanism 490 further comprises a flow sensor 494 that is in the form of a flap. Flow sensor 494 pivots about a pivot point 496 to move a cam mechanism 498, thereby rotating a wheel 500. In FIGS. 25 and 30, valving system 480 is in the inactive state where flow sensor 494 has not yet been activated. When respiratory gasses are directed through housing 482, flow sensor 494 pivots about pivot point 496 as previously described to rotate wheel 500 as illustrated in FIGS. 27, 28 and 30.

Figure 29:
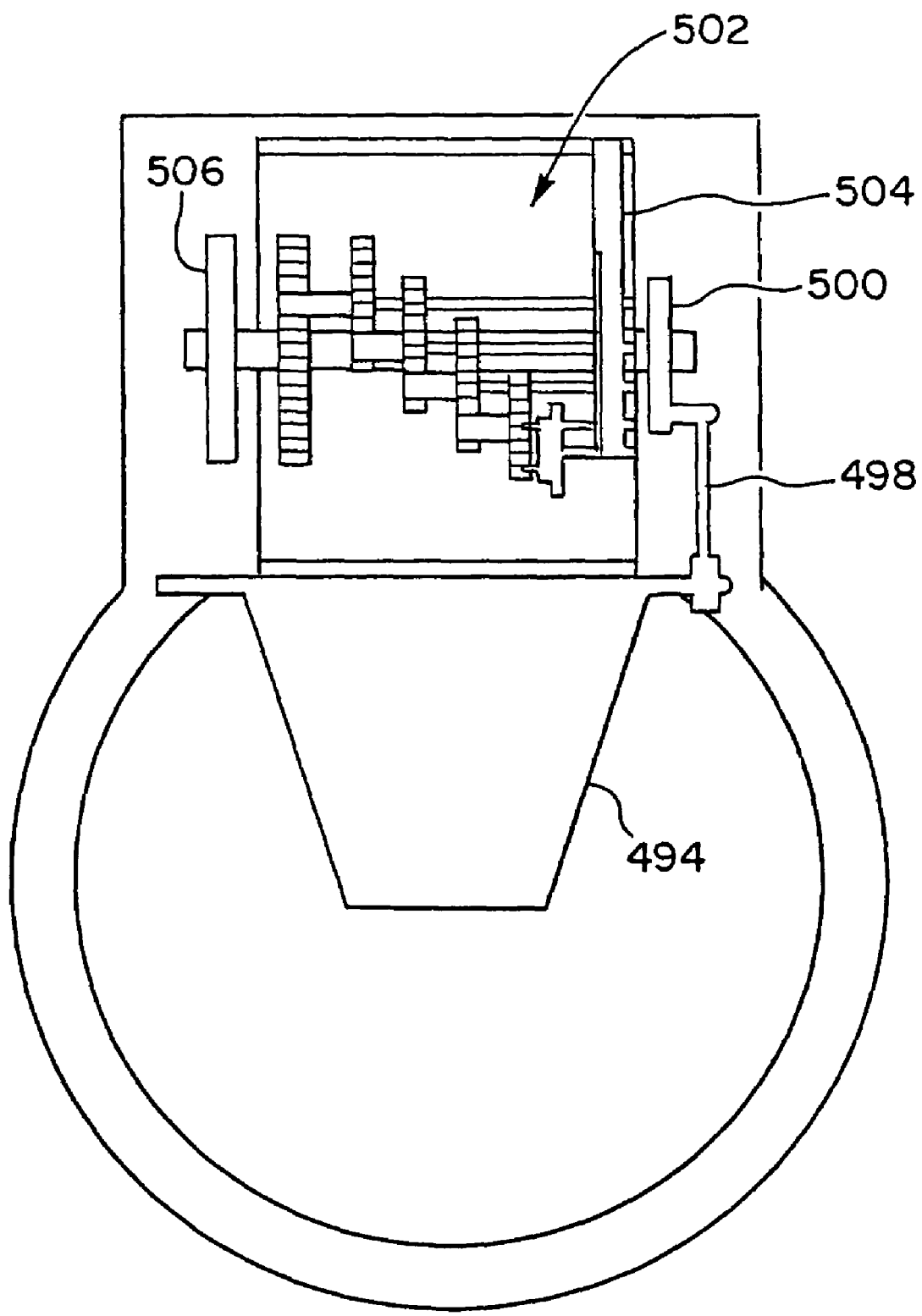
FIG. 29 is an end view of the valving system of FIG. 25.

As best shown in FIG. 29, wheel 500 is connected to a gear system 502 having a recoil spring 504 and a valve cam 506. Recoil spring 504 is employed to bias cam 506 in the position illustrated in FIGS. 25 and 30 where valve 492 is in the open position. When gasses flow through housing 482, flow sensor 494 is moved to cause wheel 500 to rotate and thereby operate gear system 502. In so doing, cam 506 is rotated to the position shown in FIGS. 27 and 31 where valve 492 moves to the closed position. Gear system 502 and recoil spring 504 operate to open valve 492 after a certain period of time has elapsed, such as about 10 to 20 seconds.

As best shown in FIGS. 30 and 31, valve 492 comprises a valve housing 508 in which is held a valve shaft 510 that holds an O-ring 512. A tension spring 514 is positioned between housing 508 and a projection 516 on shaft 510 to bias the valve 492 in the closed position as illustrated in FIG. 31. When a rescuer injects respiratory gasses into the housing of the valving system, cam 506 moves to the position shown in FIG. 30 where it engages shaft 510 and disengages O-ring 512 from housing 508 to place valve 492 in the open position. In the open position, respiratory gasses are free to flow through valve 492 and into housing 482 where they may flow to the patient's lungs through exit opening 486.

Figure 32:
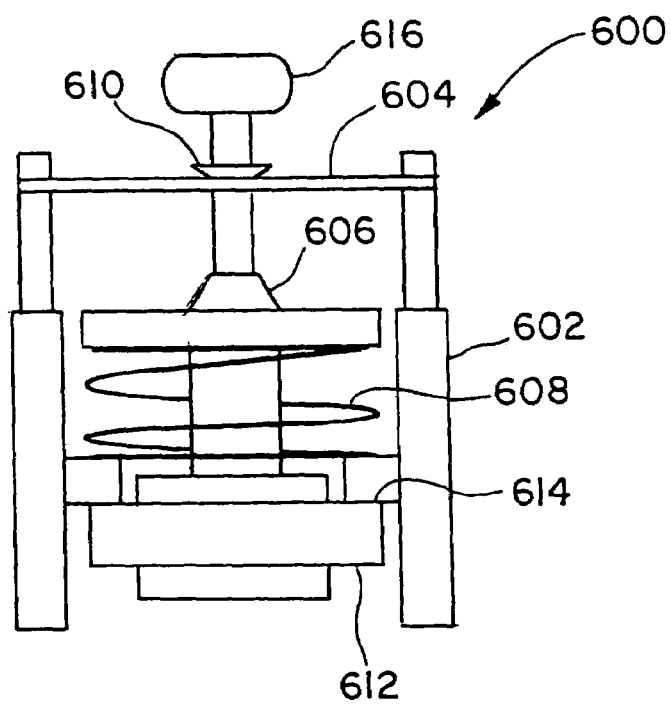
FIG. 32 is a side schematic view of one embodiment of a safety valve shown in a closed position according to the invention.
Figure 33:
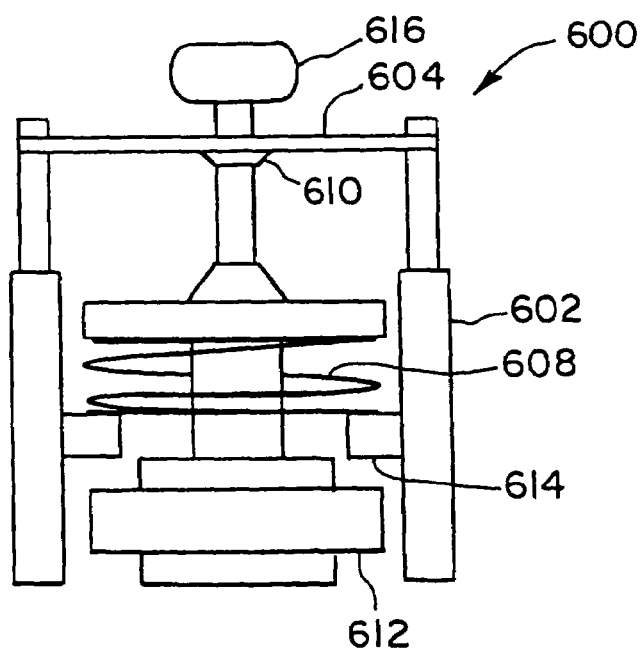
FIG. 33 illustrates the safety valve of FIG. 32 in an open position.

The invention further provides systems having safety features that allow for the patient to inhale to a given degree to release the mechanism that is used to impede or prevent respiratory gases from flowing to the lungs, thereby allowing for resistance free inspiration until a timer resets the systems or until the rescuer resets the system. One embodiment of a safety valve 600 that may be used with such systems is illustrated in FIGS. 32 and 33. Safety valve 600 may be used as a replacement for any of the pressure responsive valves described herein, such as, for example, valves 108, 160 and 111. Valve 600 comprises a housing 602 which is covered by a slit membrane 604. A valve member 606 is biased by a spring 608 into a closed position as shown in FIG. 32. In the closed position, a wedge 610, that may conveniently be colored for easy identification, extends above the slit in membrane 604. As such, wedge 610 serves as a visual indicator to the rescuer that valve 600 is in the closed position. When interfaced with a patient and in the closed position, respiratory gases may be prevented from flowing to the lungs until the negative intrathoracic pressure meets or exceeds a threshold value in a manner similar to that described with other embodiments. At such time, a seal 612 on valve member 606 moves away from a stop 614 on housing 602 to permit respiratory gases to flow to the lungs. Spring 608 then forces valve member 606 back to the closed position.

If the patient gasps and begins to breath, the amount of negative pressure created by the patient compresses spring 608 far enough so that wedge 610 is pulled through the slit in membrane 604 as shown in FIG. 33. Wedge 610 then holds valve 600 in the open position where gases may freely flow to the lungs. The rescuer may easily determine valve 600 is in the open position by noticing that wedge 610 is no longer visible. The rescuer may reset valve 600 at any time by simply pulling on a pull tab 616 to pull wedge 610 back through membrane 604.

Figure 34:
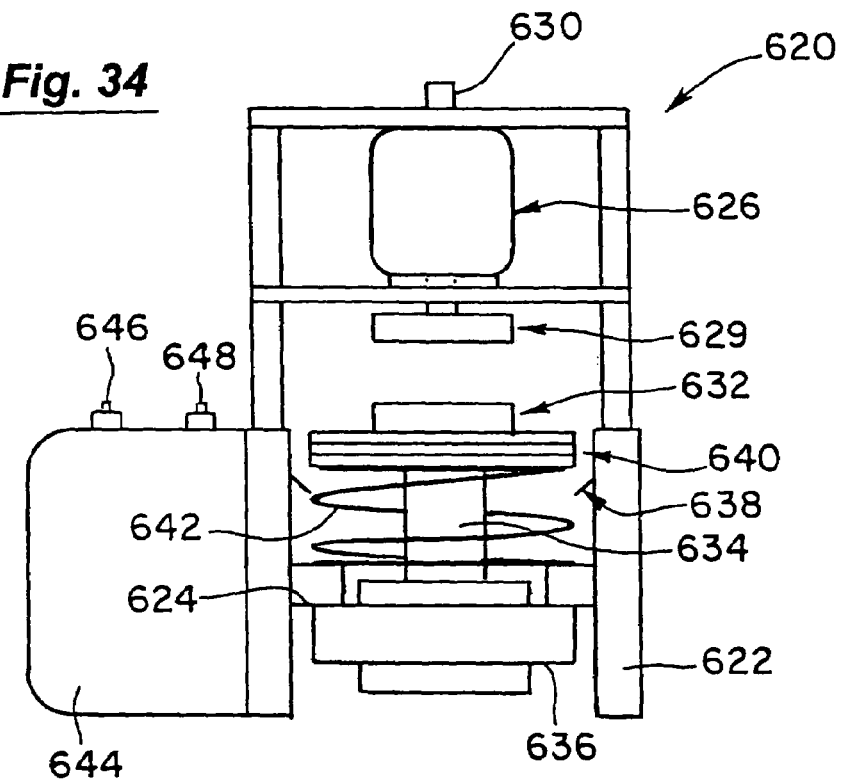
FIG. 34 is a side schematic view of another embodiment of a safety valve shown in a closed position according to the invention.
Figure 35:
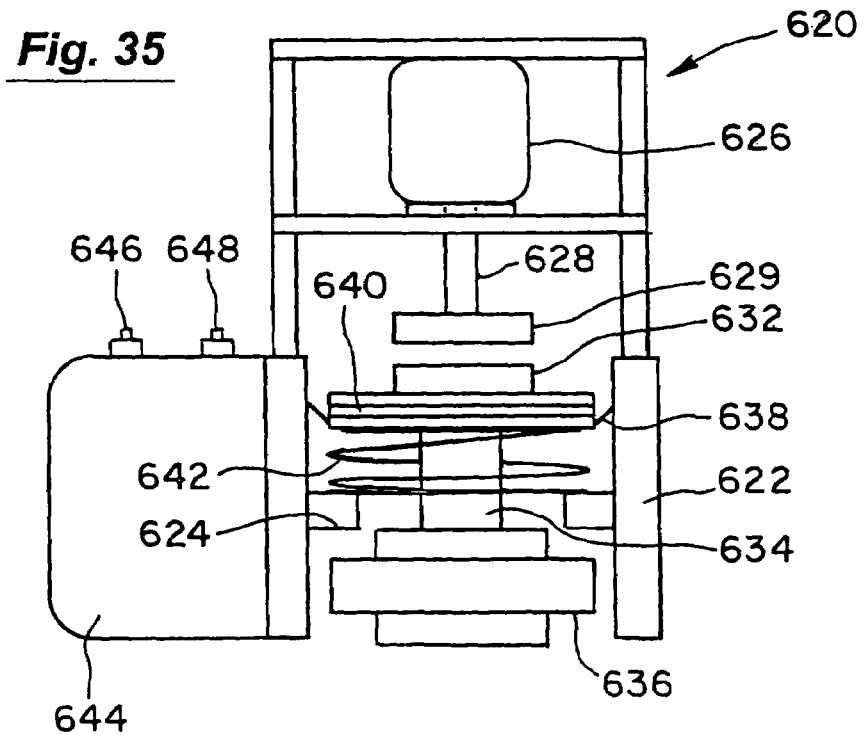
FIG. 35 illustrates the safety valve of FIG. 34 in an open position.

Another embodiment of a safety valve 620 that may be used in the systems described herein is illustrated in FIGS. 34 and 35. Valve 620 comprises a housing 622 having a stop 624. A micro-solenoid 626 is disposed within housing an includes an arm 628 having a pole magnet 629 and a visual indicator 630 at an opposite end. Spaced apart from pole magnet 629 is another pole magnet 632 of opposite polarity that is coupled to a valve member 634 having a seal 636. Coupled to housing 622 is a normally open contact strip switch 638, and valve member 634 includes a conductive strip 640. A spring 642 is disposed between strip 640 and stop 624.

FIG. 34 illustrates valve 620 in the closed or active position. During CPR, seal 636 will separate from stop 624 to permit respiratory gases to flow to the lungs when the negative intrathoracic pressure exceeds a threshold value. Valve 620 then returns back to the closed position. If the patient gasps, valve member 634 moves to the position shown in FIG. 35 where conductive strip 640 contacts switch 638. (During normal CPR, valve member 634 is not moved far enough for this contact to occur). This closes the open circuit and activates solenoid 626 to extend arm 628 and trigger a timing circuit within a control circuitry and battery compartment 644. Magnets 629 and 632 have opposite poles causing valve to remain in the open and inactive position as shown in FIG. 35 as long as solenoid 626 is actuated. In this way, the patient may continue to freely breath through valve 620. Although shown with opposing pole magnets, it will be appreciated that magnets may be substituted with a solenoid arm that may act as a plunger to make physical contact with valve member 634, and thus hold the valve open and inactive. The rescuer may note that valve 620 is in the open position by noting that indicator 630 has been retracted and is no longer visible.

Valve 620 may include an auto/manual switch 646 that may be set in automatic mode. In this mode, the timing circuit automatically deactivates solenoid 626 and returns valve 620 back to the closed and active position shown in FIG. 34 after a preset timing interval has expired. If switch 646 is set to manual, solenoid 626 remains active and valve 620 remains open and inactive as shown in FIG. 35 where respiratory gases may freely flow to the lungs. Valve 620 remains open until the rescuer manually resets solenoid 626 by pressuring a manual reset switch 648. The rescuer may note that valve 620 is closed and active by observing indicator 630 that is now extended.

Figure 36:
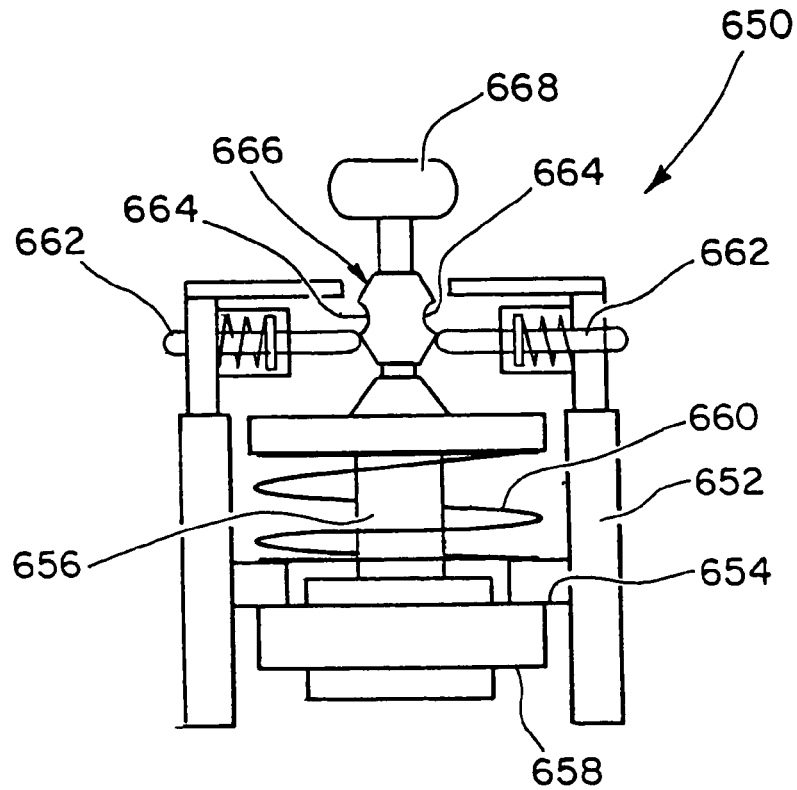
FIG. 36 is a side schematic view of yet another embodiment of a safety valve shown in a closed position according to the invention.
Figure 37:
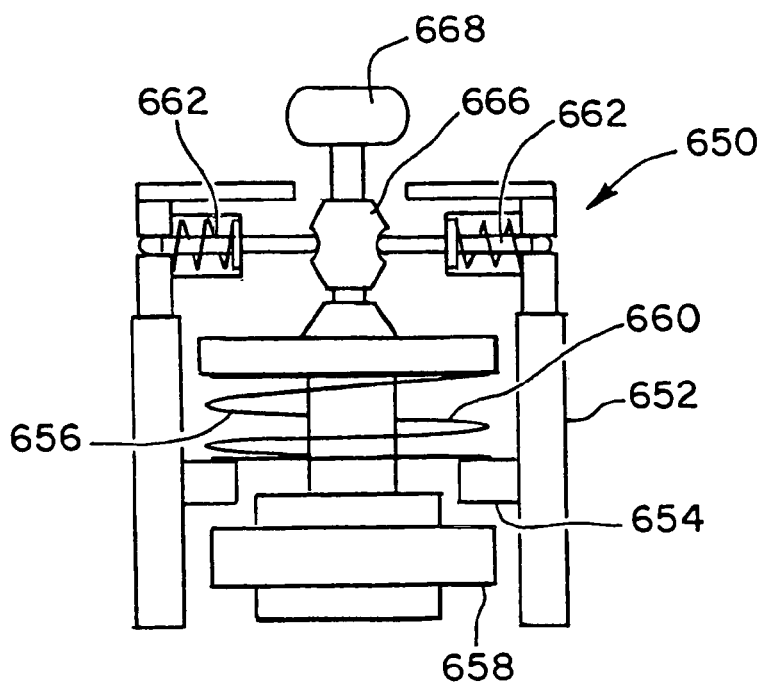
FIG. 37 illustrates the safety valve of FIG. 36 in an open position.

FIGS. 36 and 37 illustrate a further embodiment of a safety valve 650 that may be used with the systems described herein. Valve 650 comprises a housing 652 having a stop 654. Disposed within housing 652 is a valve member 656 having a seal 658 that contacts stop 654 to prevent gases from flowing through valve 650 when in the closed or active position shown in FIG. 36. In the closed position, a spring 660 biases seal 658 against stop 654 until the negative intrathoracic pressure exceeds a threshold value and seal 658 moves away from stop 654 to permit respiratory gases to flow to the lungs. Once the negative intrathoracic pressure falls below the threshold value, valve 650 moves back to the closed position.

When the patient gasps, the force created is great enough to move valve member 656 such that a pair of spring loaded pins 662 lodge within grooves 664 of a locking pin receptacle 666 on valve member 656 as shown in FIG. 37. In this way, valve 650 is locked into an open or inactive position that is created by the patient's gasp. As pins 662 move into grooves 664, the ends of pins 662 move into housing 652 to indicate to the rescuer that the valve is inactive. Conveniently, the ends of pins 662 may be colored to make them more visible to the rescuer. To reactivate valve 650, the rescuer may pull upward on a pull tab 668 on valve member 656. This releases pins 662 from grooves 664 and permit the valve to spring back to the closed position of FIG. 36.

Figure 38:
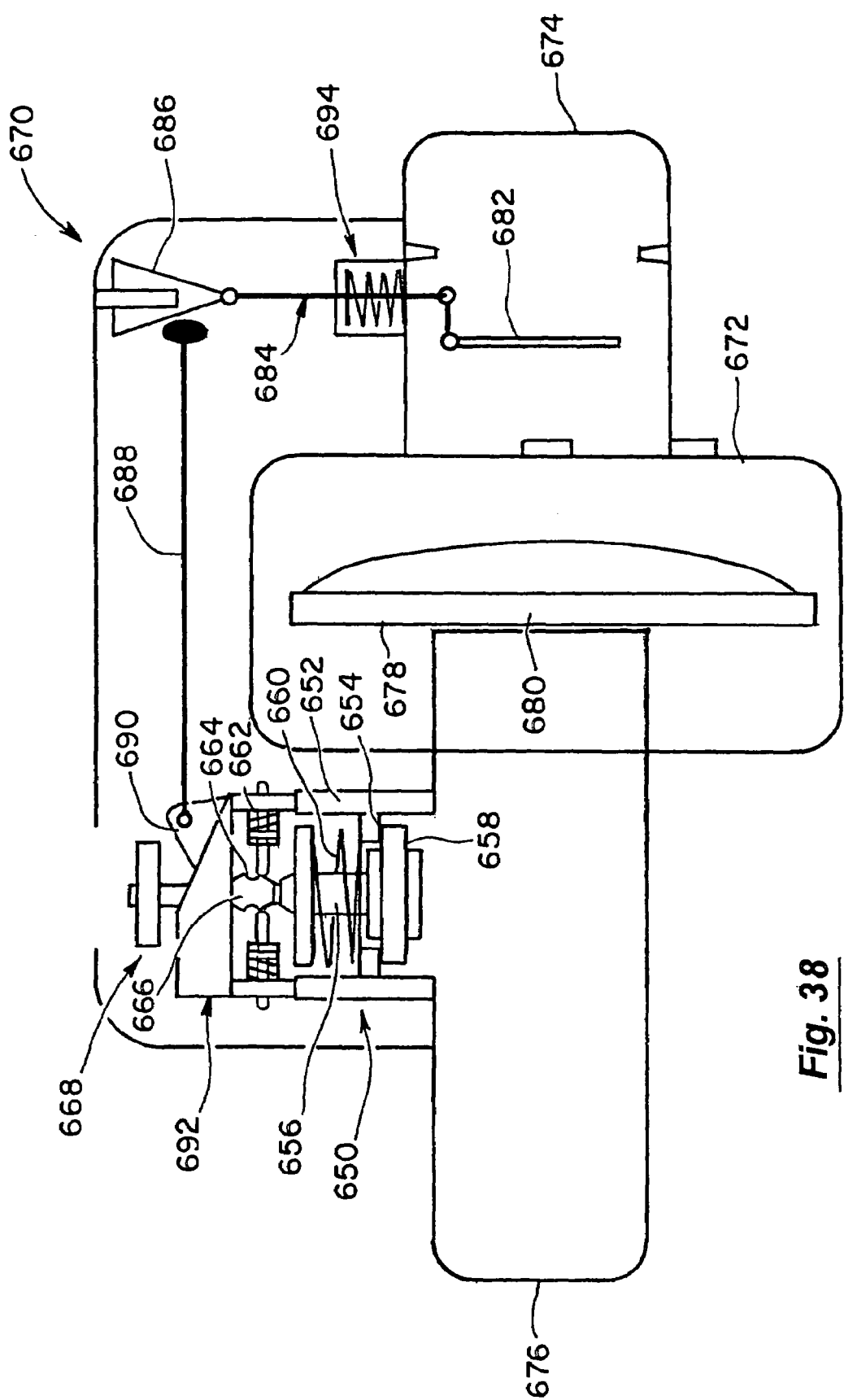
FIG. 38 is a schematic side view of an embodiment of a valving system having a safety valve that is in a closed position according to the invention.
Figure 39:
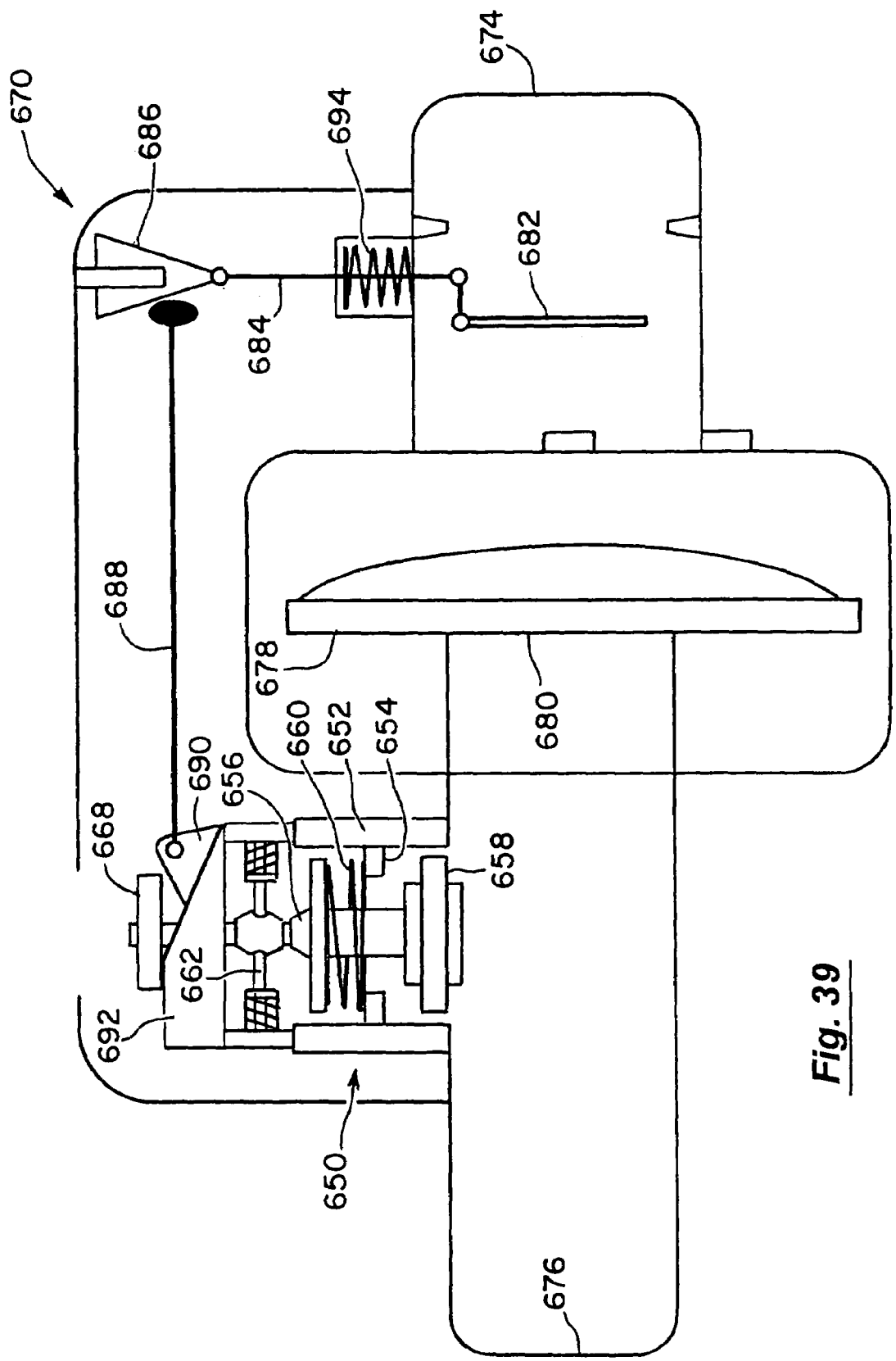
FIG. 39 illustrates the valving system of FIG. 38 when the safety valve is moved to the open position during a gasp by a patient.
Figure 40:
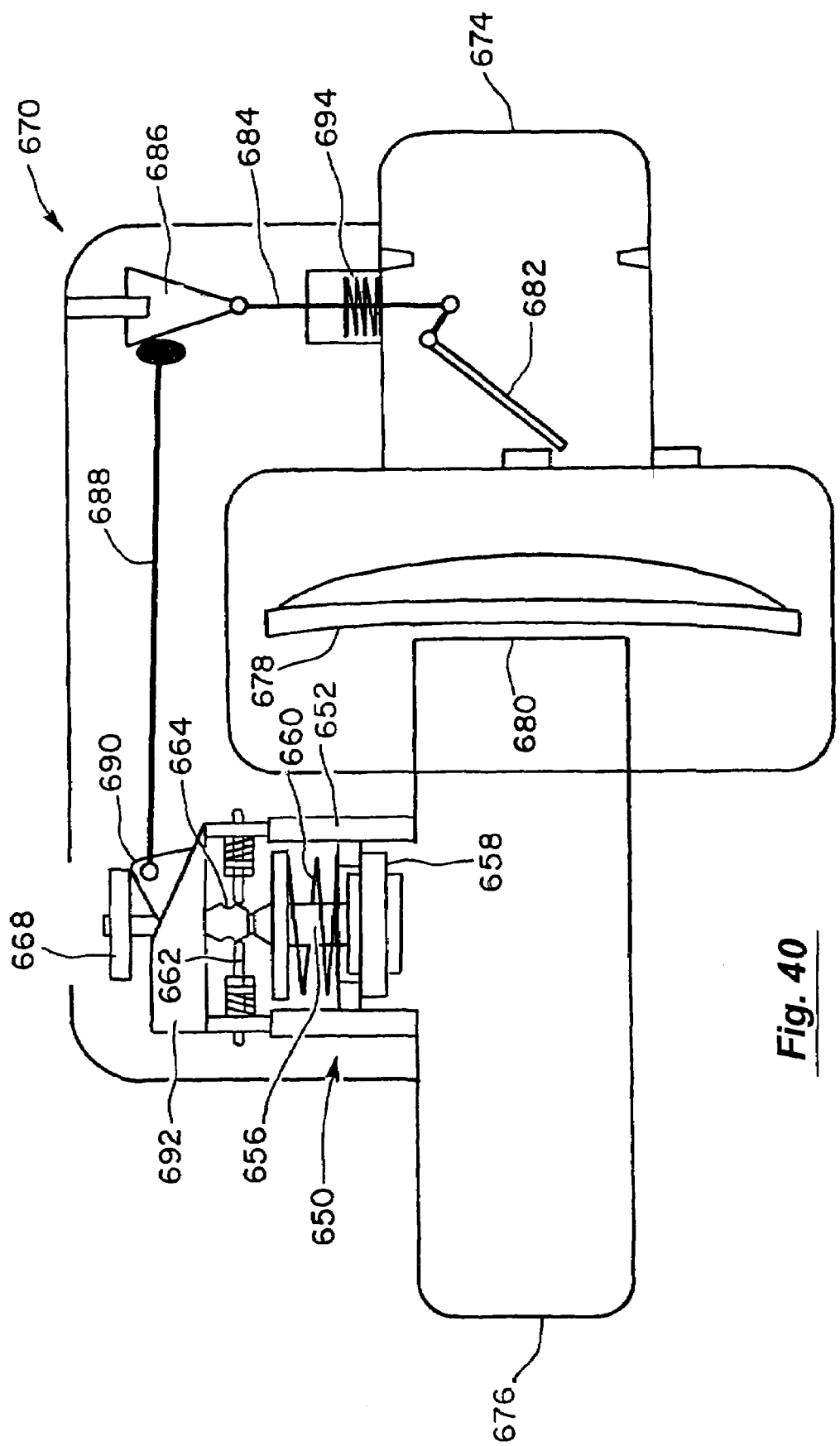
FIG. 40 illustrates the valving system of FIG. 38 during ventilation which causes the safety valve to move back to the closed position.

Referring now to FIGS. 38–40, a modified version valve 650 is shown incorporated into a valve system 670 that may be coupled to a patient's airway in a manner similar to the other valve system embodiments described herein to regulate the airflow to the patient's lungs during a CPR procedure. For convenience of discussion, identical elements of valve 650 will use the same reference numerals in describing FIGS. 38–40. The use of valve 650 allows the patient to gasp and breathe free of airway resistance after the initial gasp has occurred. Alternatively, valve 650 may be initially set in the inactive position and placed in the active state upon the initial ventilation through valve system 670, or upon subsequent ventilations if the patient gasps and locks valve 650 open and inactive.

Valve 650 is incorporated into a system housing 672 having an inlet end 674 and an outlet end 676. Conveniently, patient ventilation may occur through inlet end 674 using a ventilatory source similar to other embodiments. Outlet end 676 may be coupled to an interface that permits system 670 to be interfaced with the patient's airway. Disposed within housing 672 is a one way membrane valve 678 that is spaced apart from port 680. In FIG. 38, system 670 is in the resting state where no gasp or ventilation has occurred. When performing CPR, the chest is compressed and air forced from the patient is permitted to flow through port 680 and through valve 678. During decompression of the patient's chest, valve membrane 678 moves against port 680 to close the valve as the negative intrathoracic pressure is increased. If a threshold pressure is overcome, valve 650 opens to permit respiratory gases to flow through opening 676 after passing through valve 650. Valve 650 then moves back to the closed position and the cycle is repeated.

If valve system 670 is coupled to a patient's airway and the patient gasps or begins spontaneously breathing, valve system 670 automatically adjusts to the configuration shown in FIG. 39 so that the patient may breathe through a resistance fee airway path so that respiratory gas exchange may occur. When the patient gasps or begins to breathe, valve 678 closes and the negative pressure causes valve 650 to open and lock in place in a manner similar to that previously described in connection with FIG. 37. In this way, valve 650 remains open and inactive until reset by the rescuer by pulling on pull tab 668.

Another way to place valve 650 back into the closed or active position is by ventilating the patient through inlet 674 as shown in FIG. 40. When injecting a respiratory gas into inlet 674, the injected gases flow through valve 678 and through port 680 where the exit through outlet 676 and to the patient. In so doing, the flow of gases moves a ventilation flap 682 that in turn moves an arm 684 that is coupled to a wedge 686. Movement of wedge 686 causes lateral movement of an arm 688 that is connected to a reset wedge 690. Wedge 690 rests on top of an upward movement ramp 692. As arm 688 is laterally moved, wedge 690 moves up ramp 692 and contacts pull tab 668. In so doing, valve member 656 is pulled up until pins 662 are pulled from grooves 664 and valve 650 moves back to the closed and active position by force of spring 660. A reset spring 694 then resets ventilation flap 682 back to its home position and wedge 690 slides back down ramp 692 so that valve 650 may be reset back to the closed position if subsequently needed. Valve 650 remains in the closed and active position until another gasp or spontaneous breathing occurs.

Figure 41:
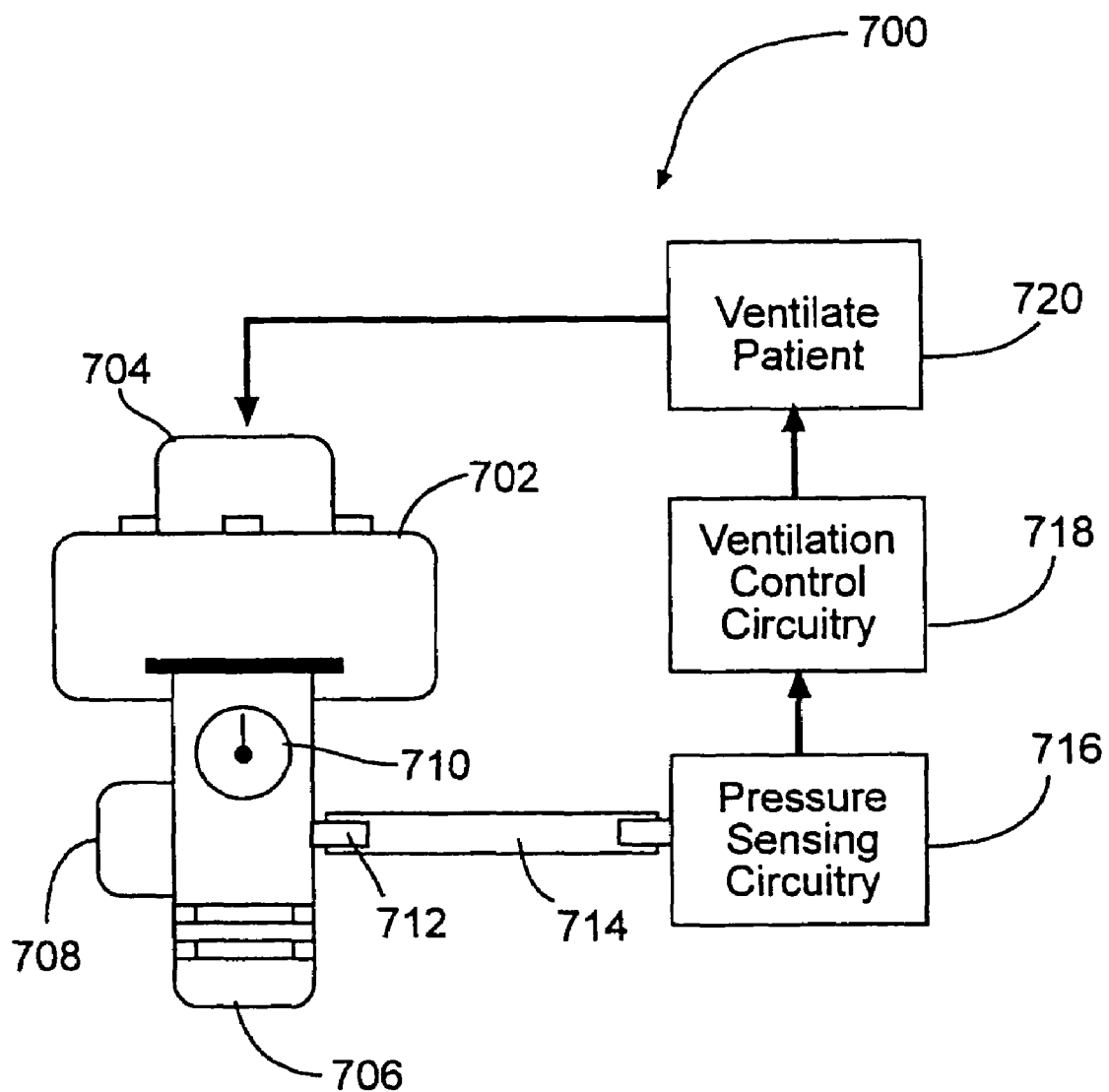
FIG. 41 is a schematic diagram of a valving system having a pressure gauge to measure pressures within the valving system according to the invention.

FIG. 41 schematically illustrates another embodiment of a valving system 700 that is configured to display the pressure within the patient's chest during CPR. Valving system 700 may be configured to be similar to any of the valving systems described herein. Hence, for convenience of discussion, valving system 700 will only be briefly described. Valving system 700 comprises a housing 702 having an inlet 704 and an outlet 706. A pressure responsive valve 708 is used to control the inflow of gases into housing 702 during decompression of the patient's chest in a manner similar to that described with other embodiments. A pressure gauge 710 is provided to measure and display the pressure within housing 702 which corresponds to the pressure within the patient's chest. In this way, pressure gauge 710 may be used to provide immediate feedback to the rescuer and may be used as a guide to determine if chest compressions and/or decompressions are being appropriately performed.

A pressure sensing port 712 is connected to a tube 714 that is connected to a pressure sensing control unit 716. In this manner, a change in pressure may be detected during either chest compressions or decompressions and act as a counting circuit to trigger ventilation control circuitry 718 to automatically ventilate the patient using a ventilator 720 after a certain number have been detected.

Alternatively, a digital control unit may be used that displays the pressure within the chest as well as the number of compressions between ventilations. With such a configuration, pressure sensing port 712 transmits pneumatically the pressure information. As such, a pressure gauge on housing 702 would not be required.

The valving systems of the invention may also be used to treat shock. Shock may conveniently be defined as a critically low blood pressure that, when untreated, may lead to death or disability. Types of shock that may be treated using techniques of the invention include, but are not limited to, low blood pressure secondary to blood loss, heat stroke, vasovagal syncope (the common faint), drowning, drug overdose, heart attack, right heart failure, return to earth after space flight, sepsis, pericardial effusion, tamponade, and the like. Further, the valve systems of the invention may be used to alter the carotid cardiopulmonary reflex sensitivity that controls blood pressure (by decreasing intra thoracic pressures with inspiration).

The valve system that are employed to treat shock are configured to completely prevent or provide resistance to the inflow of respiratory gases into the patient while the patient is breathing. For valve systems that completely prevent the flow of respiratory gases, such valves may be configured as pressure responsive valves that open after a threshold negative intra thoracic pressure has been reached. Valve systems that simply provide resistance to the inflow of respiratory gases may also be variable so that once a desired negative intra thoracic pressure is reached, the resistance to flow may be lessened. Further, the valves of the invention may be configured to be variable, either manually or automatically.

The extent to which the resistance to flow is varied may be based on physiological parameters measured by one or more sensors that are associated with the person being treated. As such, the resistance to flow may be varied so that the person's physiological parameters are brought within an acceptable range. Examples of physiological parameters that may be measured include, but are not limited to, negative intra thoracic pressure, respiratory rate, end tidal $CO_2$, positive end expiratory pressure, blood pressure, oxygen saturation, tissue $CO_2$ content, and the like. If an automated system is used, such sensors may be coupled to a controller which is employed to control one or more mechanisms that vary the resistance or actuating pressure of the inflow valve.

Figures 42, 43:
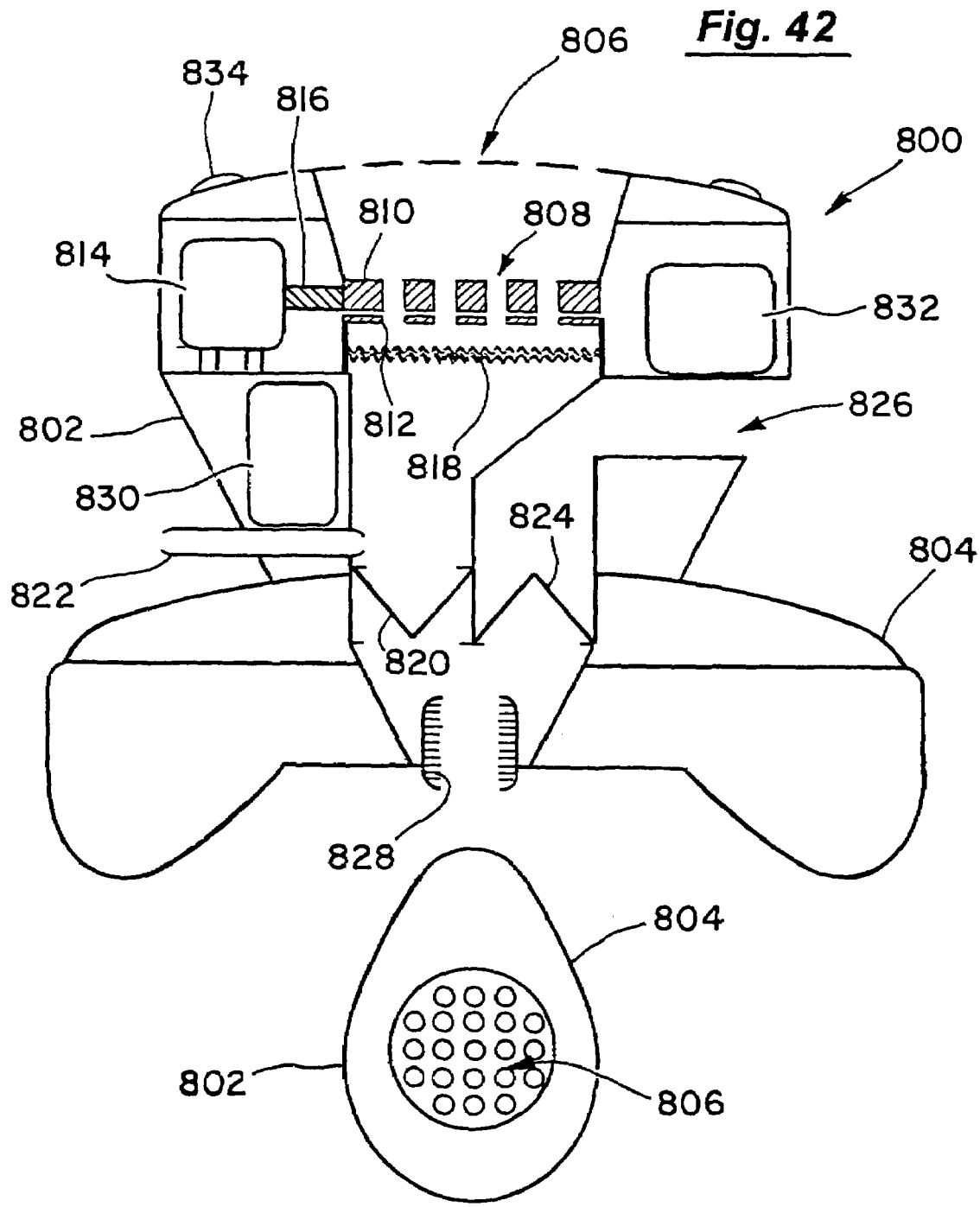
FIG. 42 is a cross-sectional schematic view of one embodiment of a system for treating a breathing person who is in shock according to the invention.
FIG. 43 is top schematic view of the system of FIG. 42.
Figure 46A:
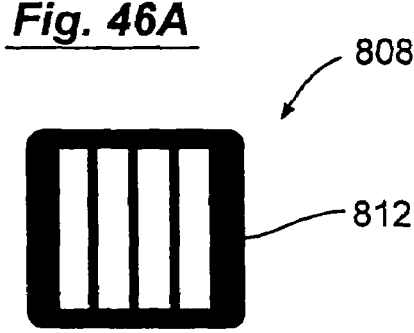
FIG. 46A illustrates one embodiment of an inflow valve according to the invention.
Figure 46B:
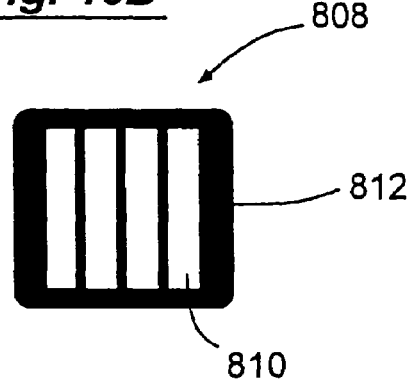
FIG. 46B illustrates the inflow valve of FIG. 46A when the resistance to flow has been increased.

Referring now to FIGS. 42 and 43, one embodiment of a system 800 that may be used to treat a person in shock will be described. System 800 comprises a housing 802 that is coupled to a facial mask 804. Housing 802 includes an inspiratory fenestrated port 806 where inspired gases are permitted to enter housing 802. Disposed below port 806 is a slotted airway resistance mechanism 808 that may be used to completely prevent or provide resistance to the respiratory gases flowing into housing 802 through port 806. Resistance mechanism 808 is also illustrated in FIGS. 46A and 46B and may be constructed of a slotted member 810 and a slotted plate 812. Slotted member 810 is movable relative to plate 812 to partially or fully cover the slots in plate 812 as illustrated in FIG. 46B. In this way, the resistance to the flow of inspired gases may be increased simply by moving slotted plate 812 relative to slotted member 810. As best shown in FIG. 42, a motor 814 that moves a shaft 816 may be employed to translate slotted member 810 over slotted plate 812 to vary the resistance to flow. Optionally, a filter 818 may be disposed below resistance mechanism 808.

System 800 further includes a one-way valve 820 that prevents expired gases from flowing back up through resistance mechanism 808. Disposed upstream of one-way valve 820 is an oxygen port 822 to permit oxygen to be supplied to the person during inspiration. System 800 further includes another one-way valve 824 that opens when the person expires to permit expired gases from exiting housing 802 through an expiratory port 826.

System 800 may also include one or more sensors 828 that measure various physiological parameters, such as flow rate, internal pressures within the patient, end tidal $CO_2$, and the like. These sensors may be coupled to a circuit board or controller 830 that may be programmed to vary operation of motor 814 based on the sensed parameters. In this way, the measured parameters may be kept within a desired range simply by controlling the resistance provided by resistance mechanism 808 in an automated manner. Although not shown, it will be appreciated that other sensors may also be coupled to circuit board 830 and may not necessarily be incorporated into housing 802 or mask 804. System 800 may also include a battery 832 to provide power to the various electrical components of system 800. A control button 834 may also be employed to actuate system 800.

Optionally, to ensure that the inspiratory lumen is never completely occluded by the airway resistance mechanisms, molded stops may be fabricated in a manner that the airway may always have a slight opening for inspiration to occur. As another option, the valve and sensing system may be attached to other airway devices, including an endotracheal tube, a laryngeal mask, or the like.

Figure 44:
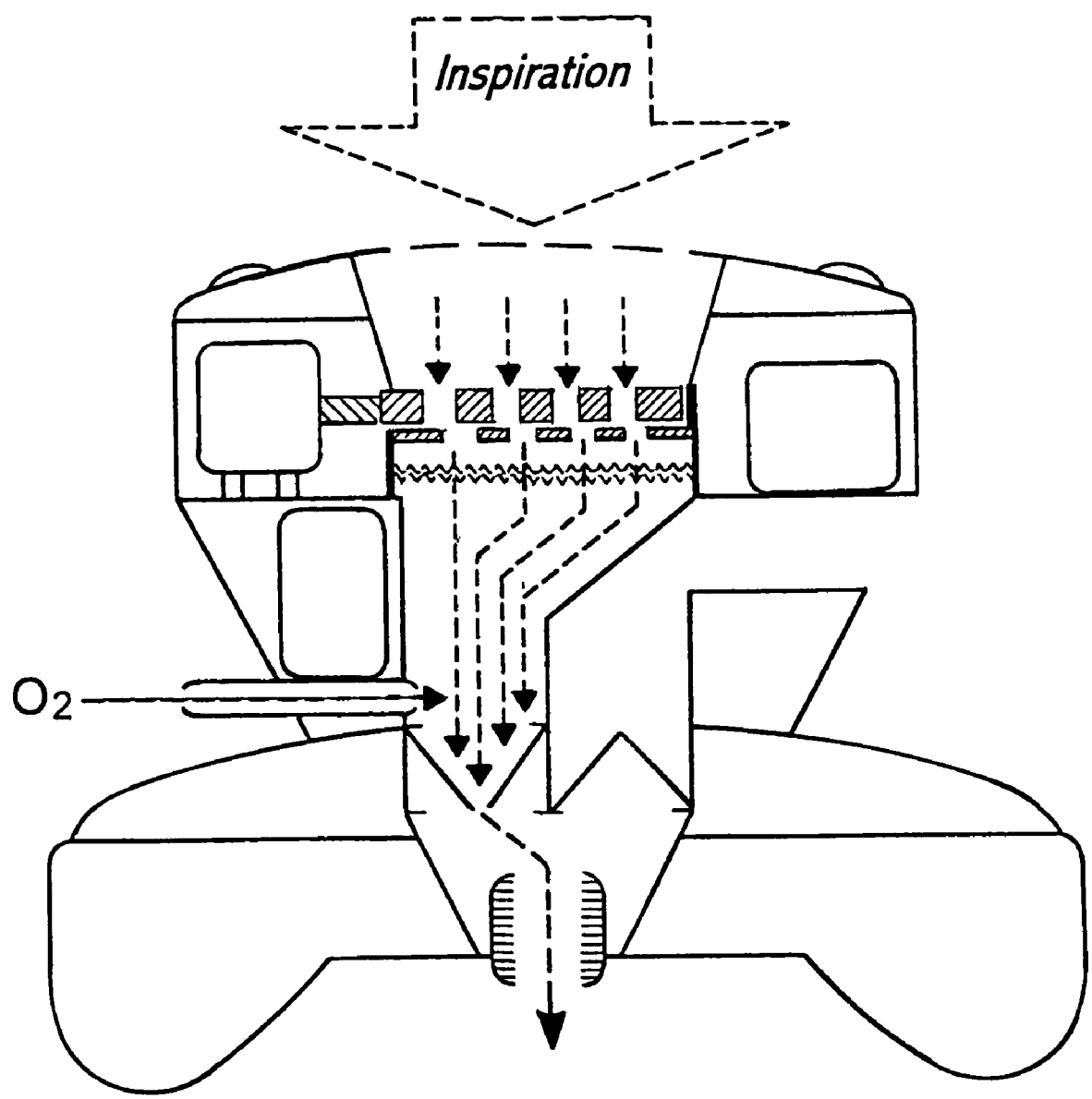
FIG. 44 illustrates the system of FIG. 42 when the person is inspiring.
Figure 45:
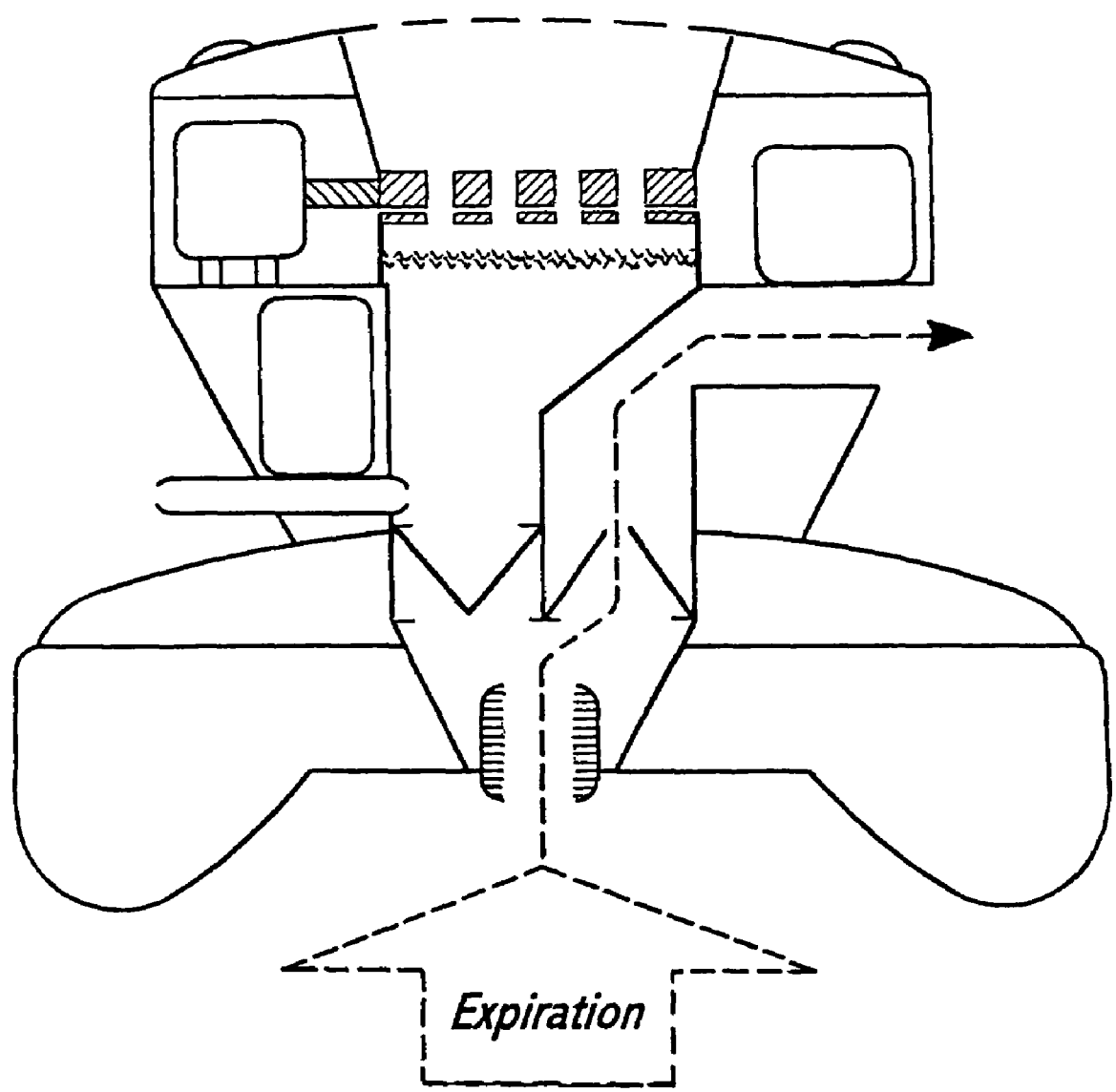
FIG. 45 illustrates the system of FIG. 42 when the person is exhaling.

FIG. 44 illustrates system 800 when mask 804 is coupled to a person and the person inhales. As shown, the inspired gases pass through resistance mechanism 808 which has been operated to increase the resistance to flow. Optionally oxygen may also be supplied to the person through oxygen port 822. FIG. 45 illustrates when the person exhales. As shown, the expired gases pass through one-way port 824 and through expiratory port 826.

Although system 800 has been shown with one particular type of valve, it will be appreciated that a variety of inflow valves may be used including any of those previously described. Further, FIGS. 47–53 illustrate other types of inflow valves that may be used to prevent or increase the resistance to flow during an inspiratory effort. Further, any of these inflow valves may be coupled to other mechanisms that may be used to operate the valve to vary the flow resistance. In this way, a controller may be used to automatically control the amount of resistance. Further, the controller may be coupled to one or more sensors so that various physiological parameters of the person may be kept within a desired range simply by measuring the parameters and using those parameters to vary the amount of resistance.

Figure 47A:
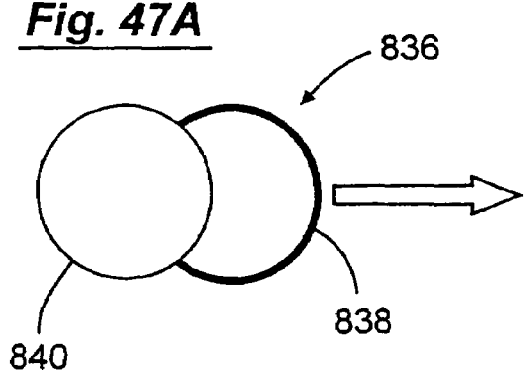
FIG. 47A illustrates another embodiment of an inflow valve according to the invention.
Figure 47B:
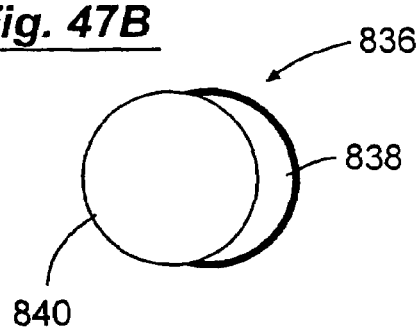
FIG. 47B illustrates the inflow valve of FIG. 47A when a disk has been moved to increase flow resistance according to the invention.

FIGS. 47A and 47B illustrate an inflow valve 836 that comprises an airway 838 and a movable disk 840. Disk 840 may be moved by any type of mechanical mechanism to occlude airway 838 as shown to increase flow resistance.

Figure 48A:
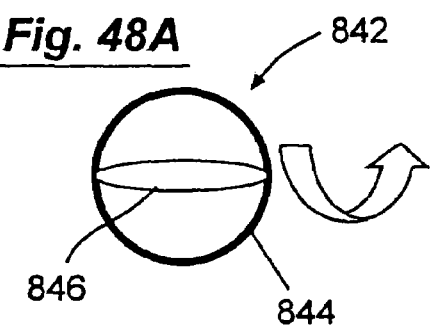
FIG. 48A illustrates yet another embodiment of an inflow valve according to the invention.
Figure 48B:
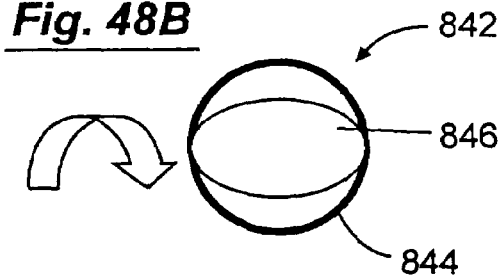
FIG. 48B illustrates the inflow valve of FIG. 48A when a disk has been rotated to increase resistance according to the invention.

FIG. 48A and FIG. 48B illustrate another embodiment of an inflow valve 842 that comprises an airway 844 and a rotatable disk 846. As shown in FIG. 48B, disk 846 may be rotated to increase the amount of flow resistance through airway 844.

Figure 49A:
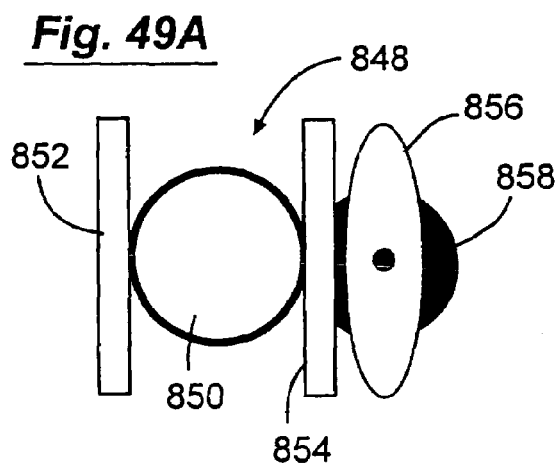
FIG. 49A illustrates a further embodiment of an inflow valve according to the invention.
Figure 49B:
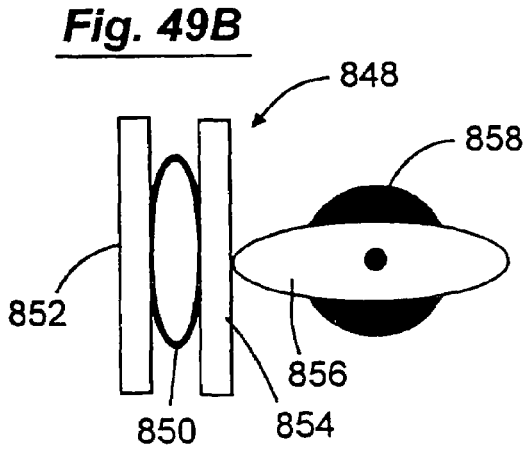
FIG. 49B illustrates the inflow valve of FIG. 49A when compressed to increase flow resistance.

FIGS. 49A and 49B illustrate an inflow valve 848 that comprises an airway 850 that is positioned between a pair of plates 852 and 854. As shown in FIG. 49B, a rotatable cam 856 may be employed to move plate 854 to compress airway 850 and thereby increase flow resistance. Conveniently, cam 856 may be rotated by a motor 858 that in turn may be controlled by a controller in a manner similar to that previously described.

Figure 50A:
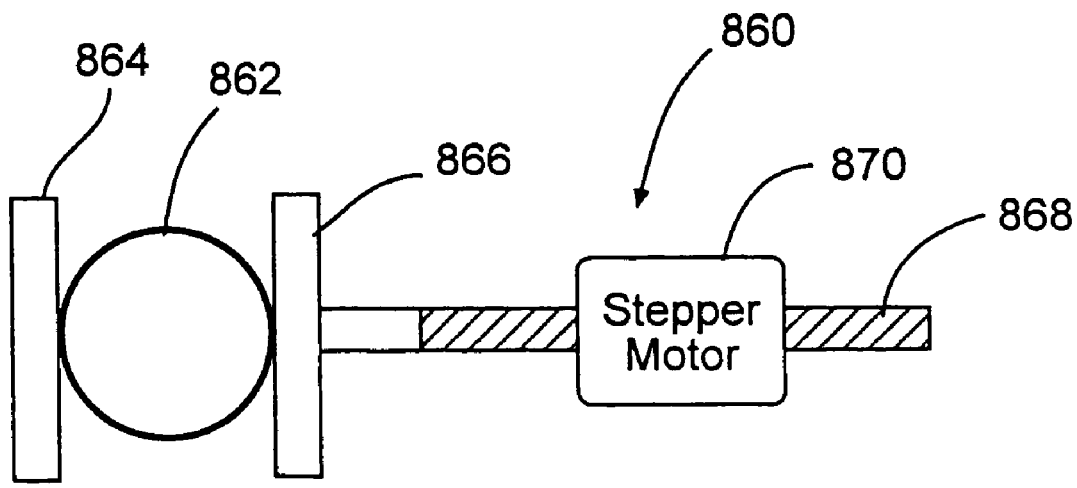
FIG. 50A illustrates yet another embodiment of an inflow valve according to the invention.
Figure 50B:
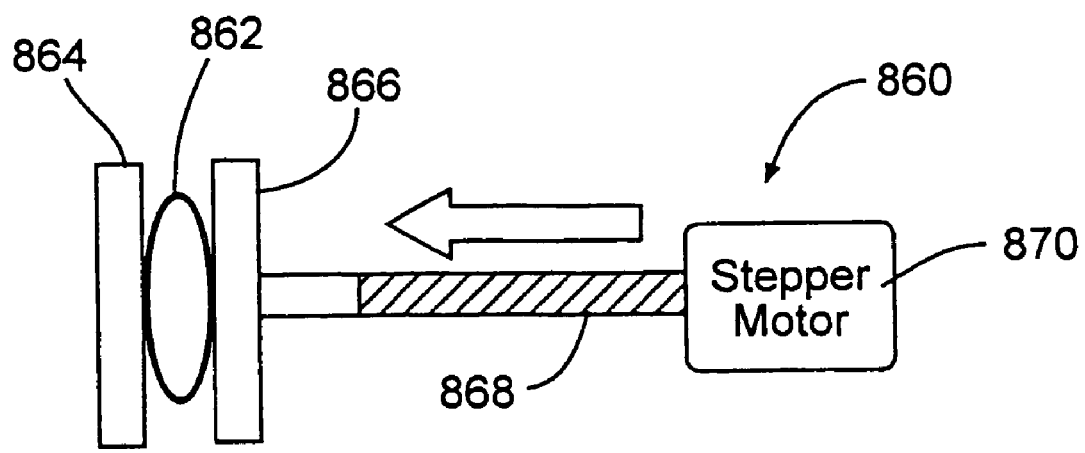
FIG. 50B illustrates the inflow valve of FIG. 50A when compressed to increase flow resistance.

FIGS. 50A and 50B illustrate a further embodiment of an inflow valve 860 that comprises an airway 862 that is positioned between two plates 864 and 866. In turn, plate 866 is coupled to a threaded shaft 868 that is movable back and forth by a stepper motor 870 that may also be coupled to a controller. In operation, stepper motor 870 is employed to move plate 866 against airway 862 as shown in FIG. 50B to increase the resistance to flow.

Figure 51A:
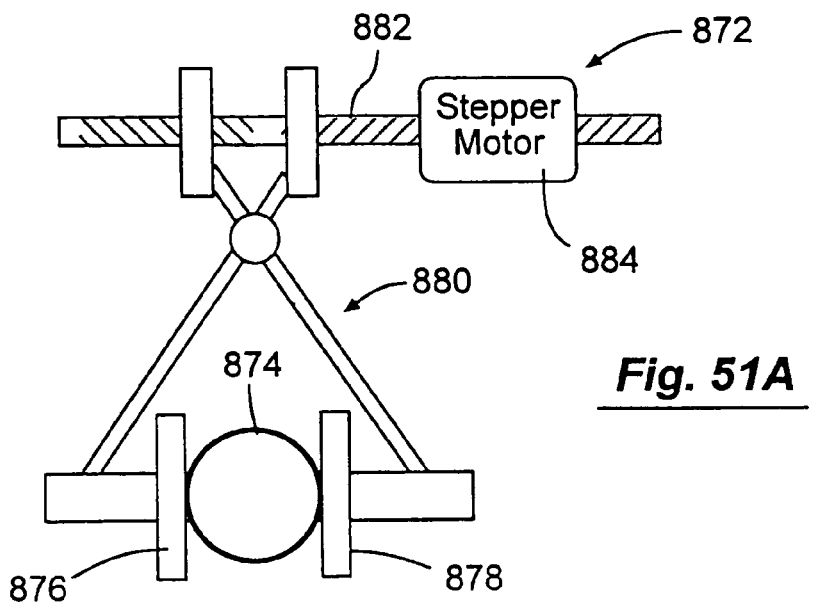
FIG. 51A illustrates a further embodiment of an inflow valve according to the invention.
Figure 51B:
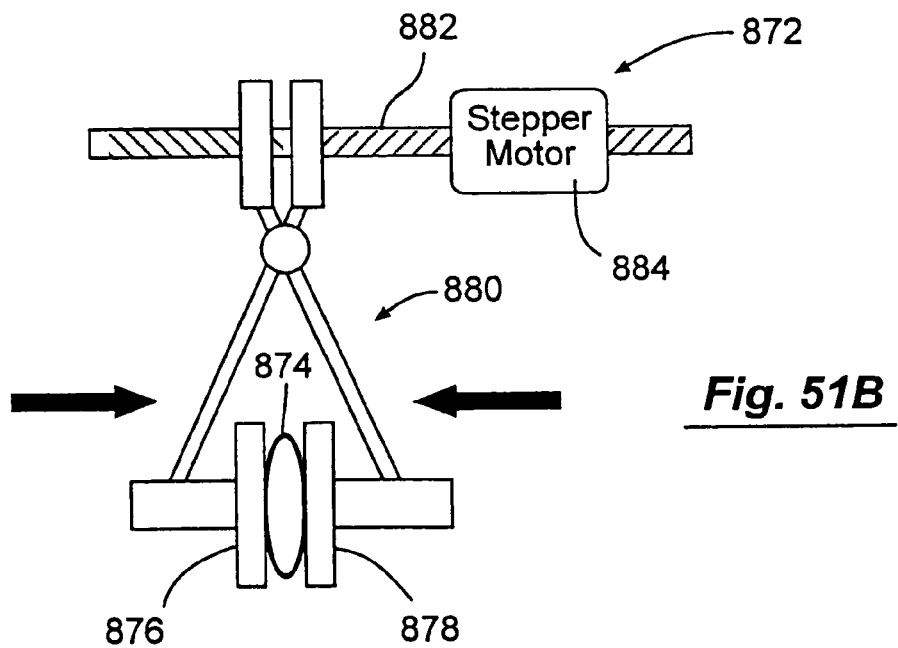
FIG. 51B illustrates the inflow value of FIG. 51A when compressed to increase flow resistance.

FIGS. 51A and 51B illustrate an inflow valve 872 that comprises an airway 874 that is positioned between a pair of plates 876 and 878. These plates are coupled to a caliper mechanism 880 that in turn is coupled to a lead screw 882 that is movable by a stepper motor 884. In this way, stepper motor 884 may be used to operate caliper mechanism 880 to in turn squeeze airway 874 as shown in FIG. 51B to increase flow resistance.

Figure 52A:
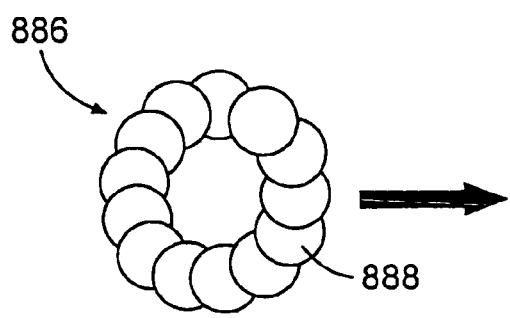
FIG. 52A illustrates still a further embodiment of an inflow valve according to the invention.
Figure 52B:
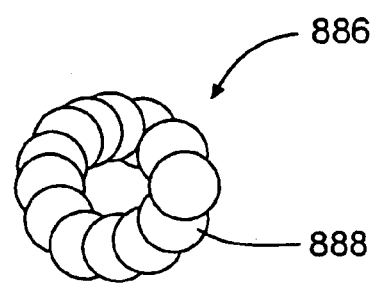
FIG. 52B illustrates iris mechanisms that have been operated to increase the resistance to flow of the inflow valve of FIG. 52A.

FIGS. 52A and 52B illustrate an inflow valve 886 that comprises an iris occluding mechanism 888. As shown in FIG. 52B, iris occluding mechanism 888 may be operated to decrease the size of the airway and thereby increase flow resistance.

Figure 53A:
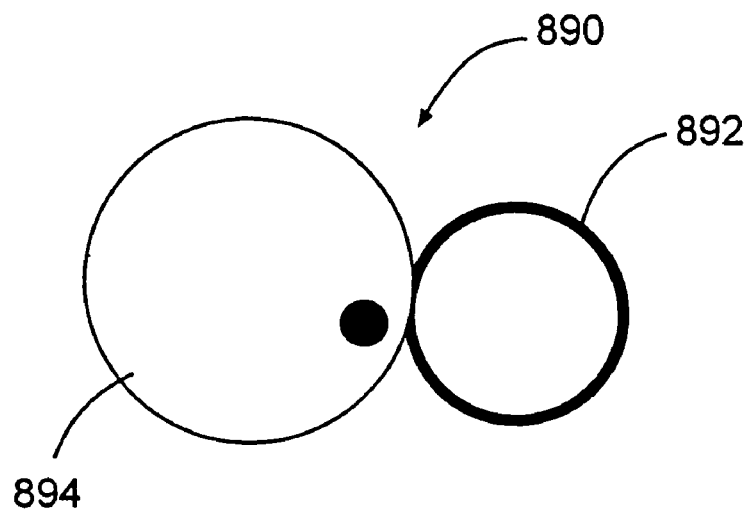
FIG. 53A illustrates still a further embodiment of an inflow valve according to the invention.
Figure 53B:
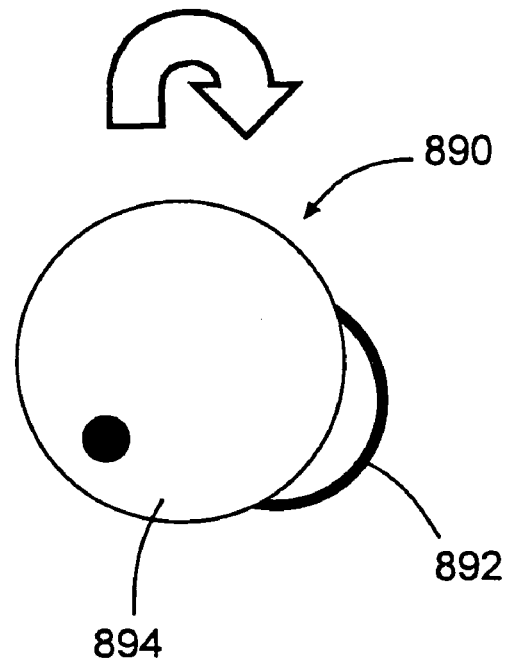
FIG. 53B illustrates the inflow valve of FIG. 53A when a disk has been pivoted to increase flow resistance.

FIGS. 53A and 53B illustrate another embodiment of an inflow valve 890 that comprises an airway 892 and a rotatable arm 894 that in turn may be coupled to a stepper motor. As shown in FIG. 53B, arm 894 is rotatable over airway 892 to increase resistance to flow.

Figure 54A:
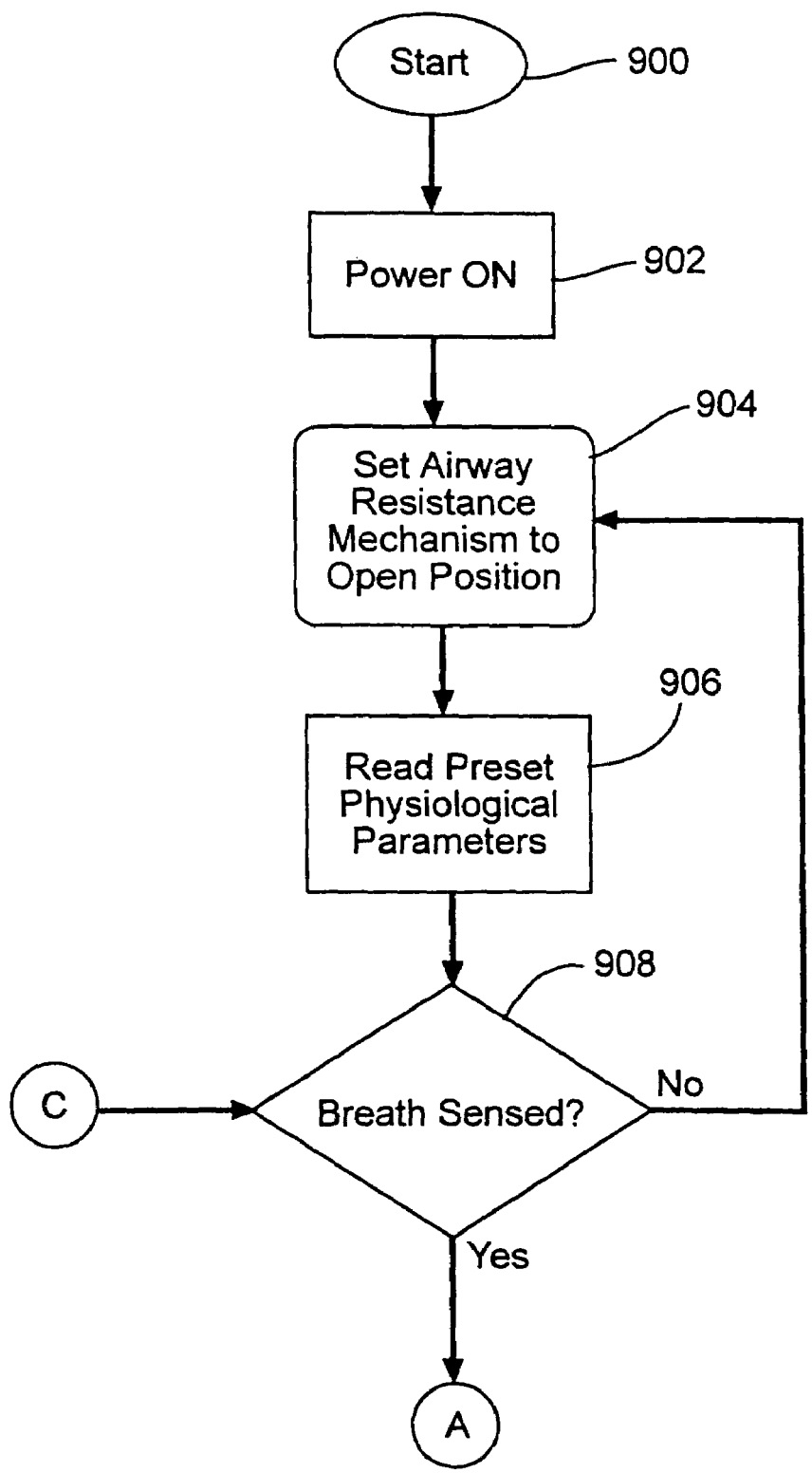
FIGS. 54A through 54C illustrate one embodiment of a method for treating shock according to the invention.
Figure 54B:
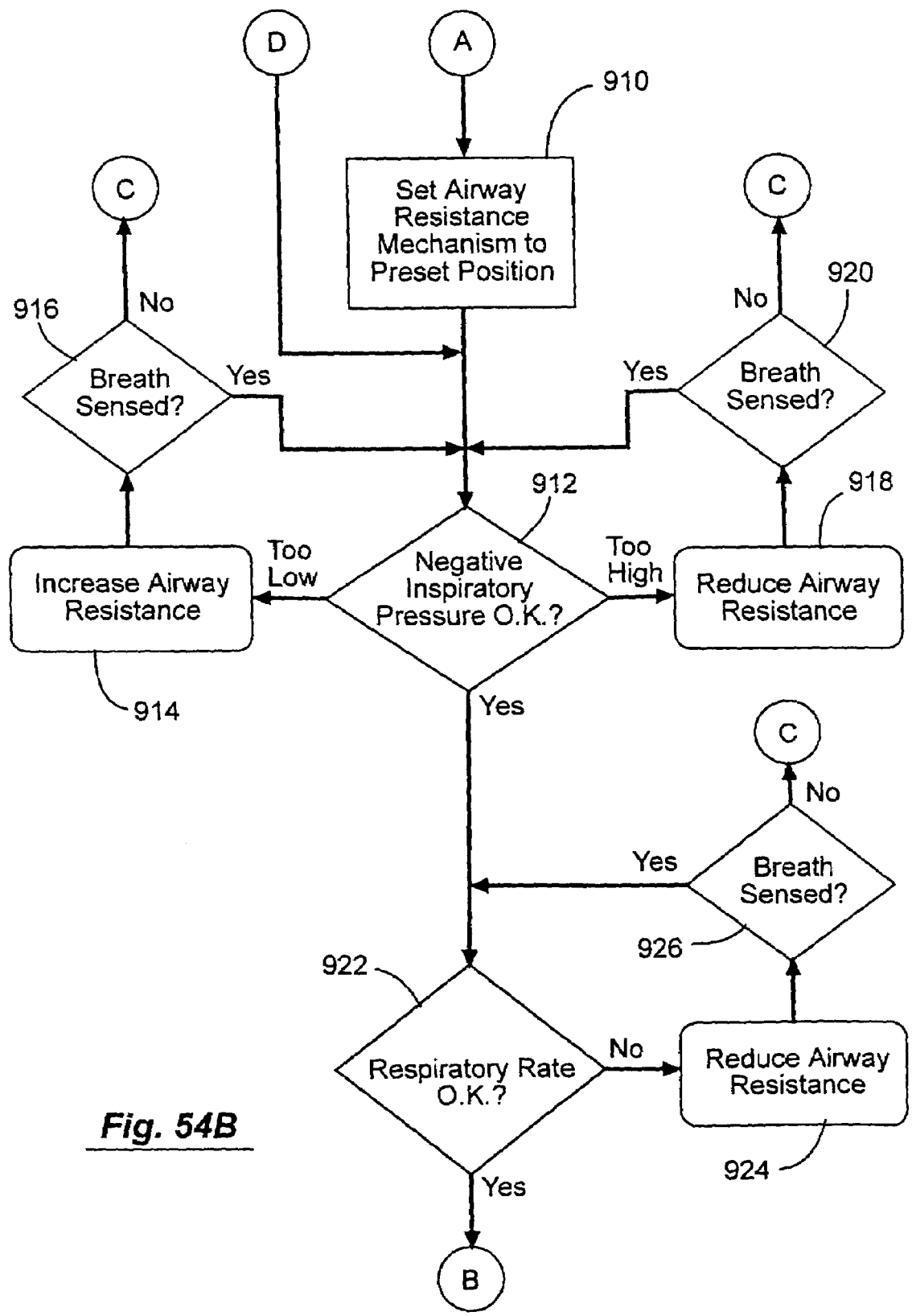
Figure 54C:
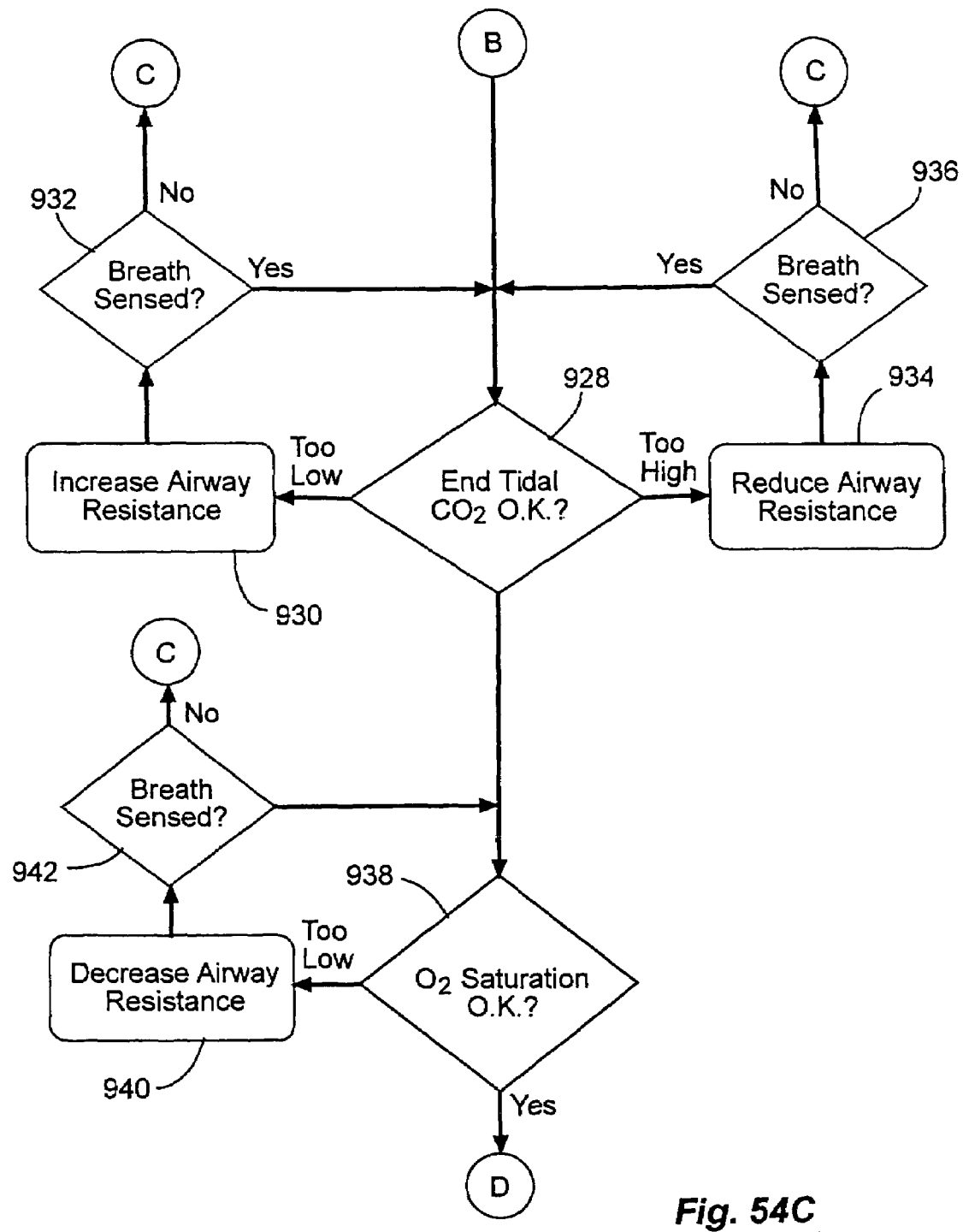

FIGS. 54A through 54C illustrate one exemplary method for treating a person in shock. The process begins at step 900 where the treatment system may be coupled to the patient's airway. For example, the system previously described in connection with FIG. 42 may be coupled to the patient's face. The power is turned on as shown in step 902 and the airway resistance mechanism may be set to an open position as shown in step 904. The treatment mechanism may include various preset physiological parameters that may initially be read to determine the person's condition. At step 908, a determination is made as to whether a breath has been sensed based on the physiological parameters previously read in step 906. If no breath has been sensed, the process is reversed back to step 904 to ensure that the airway resistance mechanism is in the open position.

If a breath has been sensed, the process proceeds to step 910 where the airway resistance mechanism is set to a preset position. This position may be based on the initial physiological parameters that were sensed in step 906. Further, the airway resistance may be set manually or may be done automatically using a controller that is programmed with various preset positions based on measured physiological parameters. The process then proceeds to step 912 where the physiological parameters are evaluated to determine whether the negative inspiratory pressure is acceptable as the patient inhales. If the negative inspiratory pressure is too low, the process proceeds to step 914 where the airway resistance is increased. This may be done in an automated manner using the controller which operates the airway resistance mechanism to increase the airway resistance. After the resistance has been increased, the process proceeds to step 916 where sensors are employed to determine whether a breath is sensed. If not, the process reverts back to step 904 where the airway resistance is moved back to its original position or to a fully open position and the process continues.

If the negative inspiratory pressure is too high, the process may proceed to step 918 where airway resistance is reduced. A breath measurement is then taken in step 920 to determine whether a breath is sensed. If not, the process proceeds back to step 904 where the airway resistance mechanism may be opened. If a breath is sensed in either step 920 or step 916, the process goes back to step 912 where another check on the negative inspiratory pressure is made. Once the negative inspiratory pressure is acceptable, the process proceeds to step 922 where the respiratory rate is evaluated. If the respiratory rate is unacceptable, the process proceeds to step 924 where the airway resistance is reduced. An evaluation as to whether a breath is sensed is made in step 926. If no breath is sensed, the process reverts back to step 904 where the airway resistance mechanism may be open. If a breath is sensed, the process proceeds back to step 922 where another evaluation of the respiratory rate is made. If the respiratory rate is acceptable, the process proceeds to step 928 and an evaluation as to the end tidal $CO_2$ is made. If too low, airway resistance is increased as shown in step 930 and another evaluation is made as to whether the patient is breathing in step 932. If not, the process proceeds back to step 904 where the airway resistance mechanism is opened. If the end tidal $CO_2$ is too high, the process proceeds to step 934 where the airway resistance is reduced and the patient's breathing is again sensed at step 936. If no breath is sensed, the process proceeds back to step 904 where the airway resistance mechanism is opened. If a breath is sensed in either steps 932 or 936, the process proceeds back to step 928 where the end tidal $CO_2$ is re-evaluated. Once acceptable, the process proceeds to step 938 where the oxygen saturation is evaluated. If too low, the airway resistance may be decreased as shown in step 940 and an evaluation is made as to whether the person is breathing as shown in step 942. If not, the process proceeds back to step 904 and the airway resistance mechanism is opened. If the oxygen saturation is acceptable, the process proceeds to step 912 so that the negative inspiratory pressure, respiratory rate, end tidal $CO_2$, and oxygen saturation may be continuously monitored and the airway resistance may be modified based on the parameters.

Hence, the method set forth in FIGS. 54A through 54C permits various physiological parameters to be continuously monitored and to permit the resistance to inspiratory flow to be modified so that these parameters remain within an acceptable range when treating a patient suffering from shock. Further, as previously described, the augmentation of negative inspiratory pressure permits increased blood flow back to the right heart to increase the patient's blood pressure. Although shown monitoring the various physiological parameters in a certain order, it will be appreciated that the parameters may be monitored in other orders as well. Further, other physiological parameters may be measured to ensure that the patient remains in a stable condition when treating the patient for shock. Optionally, the method of FIGS. 54A through 54C may also be used to evaluate the patient's positive end expiratory pressure. Further, similar airway resistance mechanisms may be applied to the expiratory port and the airway resistance of the expiratory port may be varied based on the sensed parameters. For example, the expiratory pressure may be varied to aid in the prevention of alveoli collapse (atelectasis) which may occur when the negative intrathoracic pressure is too low for a prolonged period of time.

It is estimated by the American Diabetes association that approximately 17 million Americans have diabetes. Diabetes is a disease where the body does not produce or properly use insulin. Insulin is a hormone that is used to covert sugar, starches and other food into energy that is used by the body. There are two major types of diabetes, Type 1 and Type 2.

Type 1 diabetes results from the body's failure to produce insulin. Type II diabetes results from insulin resistance where the body fails to properly use insulin. With Type I diabetes, the function of pancreatic beta cells is lowered. This may result from hereditary cause, viral infection, and the like, where insulin is generally not secreted. This usually attacks people in their twenties to thirties. Type II diabetes mainly attacks in those in their forties and may result from a family history of diabetes, obesity, stress, and the like. In the case of Type II diabetes, since insulin is sufficiently secreted from the pancreas but insulin resistance and glucose utilization are different from those of normal person, blood sugar is not returned to normal levels in spite of hyperinsulinemia.

Diabetes is also accompanied with various symptoms. Typical examples of such symptoms include polyuria, excessive drinking and polyphagia. For instance, diabetic patients may exhibit polyuria which is caused by excretion of glucose and excessive water through urine by the action of osmotic pressure originating from high blood glucose levels. As such, such patients may complain of thirst caused by dehydration, which induces excessive drinking. This in turn may lead to excessive intake of food. As another example, diabetic patients cannot efficiently utilize glucose as an energy source. As such they often utilize protein and fat that are preserved in the body, and this can lead to obesity.

Moreover, if diabetes becomes chronic due to lack of adequate treatment, chronic vascular diseases (CVD) may arise. Thus, diabetic complications such as diabetic retinopathy (visual disturbance, blindness, retinal hemorrhage), diabetic nephropathy, diabetic ulcers, diabetic peripheral neuropathy, orthostatic intolerance (low blood pressure when standing or sitting), and the like may be experienced. Such complications may reduce general metabolic and sensory functions of the human body.

Hence, many people with diabetes are especially susceptible to heart and blood vessel disease. More specifically, diabetes carries an increased risk for heart attack, stroke, and complications related to poor circulation. For example, people with Type 1 diabetes are unlikely to get heart disease when they are young. However, as they get older, their risks become greater than those without diabetes. Further, men with diabetes have a greater risk of cardio vascular disease than women.

Traditional treatments for those suffering from diabetes include suggestions to maintain proper blood glucose levels, abstain from smoking, maintain a proper blood pressure, maintain proper blood fat levels, eat a healthy diet and exercise. The valve systems of the invention may be used alone or in combination with such treatments to help reduce the ailments that may accompany diabetes, and especially those ailments that arise from poor cardio vascular circulation and improper blood pressures.

More specifically, by coupling any of the valve systems of the invention to a person's airway, negative and/or positive intrathoracic pressures may be manipulated while the person is breathing. In so doing, more blood is brought back into the chest when inhaling and more blood may be forced out of the heart when exhaling, thereby increasing circulation. Hence, use of the valve systems increases blood flow to the heart, brain, pancreas, kidneys and peripheral vasculature beds in spontaneously breathing individuals. This results in better vital organ perfusion and function. In turn, this may lead to better control of hyperglycemia and improved vital organ function to improve the condition of those suffering from diabetes, ranging from improved wound healing to improved renal function, cardiac function, and brain function. Moreover, by requiring effort on behalf of the person in order to breath through the valve system, the person's body is exercised, both subtly and chronically, without ill effects. Hence, the valve systems of the invention may be used to treat those with Type I and Type II diabetes.

By using the valve systems, patients suffering from low blood pressure or orthostatic hypotension will benefit acutely and chronically from the invention.

Any of the valve systems described herein may be used to treat those suffering from diabetes. The valve systems may be attached to any of the interfacing mechanisms described herein, including facemasks, mouthpieces and the like. Further, the valve systems may be used over prolonged periods of time, such as while the person sleeps at night.

The valve systems when used to treat diabetes may also be used in combination with one or more physiological sensors to help insure that patients do not over exert themselves. Any of the physiological sensors described herein may be used to monitor the patient's wellbeing. In some cases, the amount of resistance supplied by the valve systems may be automatically varied based on the sensed parameters. Some examples would be sensors for inspiratory rate, end tidal $CO_2$, and work of breathing.

When treating those suffering from diabetes, the valve systems may comprise an inflow valve that opens when a certain negative intrathoracic pressure is reached. The cracking pressure of the valve may be in the range from about −3 cm $H_2O$ to about −10 cm $H_2O$. This pressure is sufficient to induce enough blood flow back into the chest to treat the ailments associated with diabetes without overexerting the patient.

In some cases, resistance to expired respiratory gases may also be provided. This may be either PEEP or a continuous positive airway pressure. For example, an outflow valve may be configured to open when a positive intrathoracic pressure is in the range from about 0 cm $H_2O$ to about 5 cm $H_2O$. Such a pressure helps to increase blood circulation throughout the body without over exerting the patient.

EXAMPLE

A valve system similar to the one illustrated in FIGS. 11–15 was manufactured with −7 cm $H_2O$ cracking pressure (active valve), or as a sham valve. Fourteen human subjects (7 males, 7 females), ranging in age from 20 to 55, were studied in a prospective blinded trial. The valve order was randomized, and each study was separated by >24 hours. Subjects lay supine and breathed through the valve system attached to a facemask. Blood pressure, cardiac output, measured by chest wall bioelectrical impedance, and heart rate were monitored before, during, and after subjects breathed through the valve system for a 14 minute interval.

When comparing the sham versus the active valve system, the systolic and diastolic blood pressure (mmHg), stroke volume (L/min), cardiac output (L/min), total peripheral resistance (pru) and the heart rate (bpm) were 115±2 vs 122±2 ($p=0.005$), 73±1 vs 74±1 ($p=n.s.$), 124±3 vs 137±3 ($p=0.013$), 7.7±0.3 vs 9.3±0.3 ($p=0.001$), 11.8±0.4 vs 10.0±0.4 ($p=0.003$), 63±3 vs 68±3 ($p=0.049$), respectively. All subjects tolerated the increased inspiratory resistance without difficulty.

Use of the valve system with an opening pressure −7 cm $H_2O$ was well tolerated and resulted in a significant increase in stroke volume and cardiac output and a decrease in total peripheral resistance in human volunteers. As such, the valve system may be useful in treating patient's suffering from diabetes.

The following example demonstrates the increased circulation that was achieved using a threshold impedance valve with spontaneously breathing individuals.

Although the foregoing invention has been described in some detail by way of illustration and example, for purposes of clarity of understanding, it will be obvious that certain changes and modifications may be practiced within the scope of the appended claims.

What is claimed is:

1. A device for facilitating the treatment of a person suffering from diabetes, the device comprising:
   a housing having an opening that is adapted to be interfaced with the person's airway; and
   a valve system that is operable to regulate respiratory gas inflow through the housing and into the person's lungs due to spontaneous inhalation, the valve system assisting in manipulating intrathoracic pressures to increase blood flow back to the person's chest and thereby enhance vital organ perfusion and function;
   wherein the valve system is configured to permit respiratory gases to flow to the person's lungs due to spontaneous inhalation when the negative intrathoracic pressure reaches a pressure in the range from about −3 cm $H_2O$ to about −10 cm $H_2O$ in order to treat the person suffering from diabetes.

2. A device as in claim 1, wherein the valve system is further configured to regulate respiratory gas flow from the person's lungs during spontaneous exhalation to further assist in manipulating intrathoracic pressures to enhance vital organ perfusion and function.

3. A device as in claim 2, wherein the valve system is configured to permit respiratory gases to flow from the person's lungs due to spontaneous exhalation when the intrathoracic pressure is in the range from about 0 cm $H_2O$ to about 7.5 cm $H_2O$.

4. A device as in claim 1, wherein valve system comprises an inflow valve that is selected from a group of valves consisting of a fish mouth valve, a spring-poppet valve, a ball valve, a flexible plug valve, a slotted airway resistance valve, a movable disk valve, a compressible airway valve, an iris valve and a sequential series of adjusting valves.

5. A device as in claim 1, further comprising at least one physiological sensor that is attachable to the patient to monitor at least one physiological parameter of the person while spontaneously breathing through the valve system.

6. A device as in claim 1, further comprising a facial mask coupled to the housing.

7. A device as in claim 1, further comprising a mouthpiece coupled to the housing.

8. A device for facilitating the treatment of a person suffering from diabetes, the device comprising:
   a housing having an opening that is adapted to be interfaced with the person's airway; and
   a valve system that is operable to regulate respiratory gas inflow through the housing and into the person's lungs due to spontaneous inhalation, the valve system assisting in manipulating intrathoracic pressures to increase blood flow back to the person's chest and thereby enhance vital organ perfusion and function; and
   at least one physiological sensor that is attachable to the patient to monitor at least one physiological parameter of the person while spontaneously breathing through the valve system;
   wherein the valve system is configured to permit respiratory gases to flow to the person's lungs due to spontaneous inhalation when the negative intrathoracic pressure reaches a pressure in the range from about −3 cm $H_2O$ to about −10 cm $H_2O$ in order to treat the person suffering from diabetes.

* * * * *